(12) United States Patent
Larrieu et al.

(10) Patent No.: US 9,809,562 B2
(45) Date of Patent: Nov. 7, 2017

(54) NAT10 MODULATORS FOR TREATING OR PREVENTING LAMINOPATHIES, AGING AND CANCER

(71) Applicants: CAMBRIDGE ENTERPRISE LIMITED, Cambridge (GB); THE CENTRE NATIONAL DE LA RECHERCHE SCIENTIFIQUE, Paris (FR)

(72) Inventors: Delphine Laurence Daniele Larrieu, Cambridge (GB); Raphaël Joël Rodriguez, Vers-Pont-du-Gard (FR); Sébastien Frédéric Stéphane Britton, Ramonville-Saint-Agne (FR); Stephen Philip Jackson, Cambridge (GB)

(73) Assignees: CAMBRIDGE ENTERPRISE LIMITED, Cambridge (GB); THE CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/301,485

(22) PCT Filed: Apr. 2, 2015

(86) PCT No.: PCT/GB2015/051040
§ 371 (c)(1),
(2) Date: Oct. 3, 2016

(87) PCT Pub. No.: WO2015/150824
PCT Pub. Date: Oct. 8, 2015

(65) Prior Publication Data
US 2017/0174644 A1    Jun. 22, 2017

(30) Foreign Application Priority Data

Apr. 3, 2014   (GB) .................... 1405991.9

(51) Int. Cl.
*C07D 277/50* (2006.01)
*A61K 31/426* (2006.01)
*C07D 285/16* (2006.01)
*A61K 31/549* (2006.01)

(52) U.S. Cl.
CPC .......... *C07D 285/16* (2013.01); *A61K 31/426* (2013.01); *A61K 31/549* (2013.01); *C07D 277/50* (2013.01)

(58) Field of Classification Search
None
See application file for complete search history.

(56) References Cited

U.S. PATENT DOCUMENTS

| 2009/0203747 A1 | 8/2009  | Chaimbault et al. |
| 2009/0280111 A1 | 11/2009 | Zheng et al. |
| 2010/0144805 A1 | 6/2010  | Wagner et al. |
| 2013/0178505 A1 | 7/2013  | Chorev et al. |
| 2013/0203799 A1 | 8/2013  | Gordon et al. |

FOREIGN PATENT DOCUMENTS

| CN | 103006653 A    | 4/2013 |
| EP | 1191024 A1     | 3/2002 |
| WO | 2013123403 A1  | 8/2013 |
| WO | 2013158046 A1  | 10/2013 |

OTHER PUBLICATIONS

Chimenti et al.Bioorganic & Medicinal Chemistry Letters 17 (2007) 4635-4640.*
International Search Report issued in PCT/GB2015/051040, dated Jul. 1, 2015.
H. Xu et al., "N-α-Acetyltransferase 10 protein inhibits apoptosis through RelA/p65-regulated MCL1 expression," Carcinogenesis 33(6):1193-1202 (2012).
Chung-Fan Lee et al., "hNaa10p contributes to tumorigenesis by facilitating DNMT1-mediated tumor suppressor gene silencing," Journal of Clinical Investigation, 120(8):2920-2930 (2010).
D. Larrieu et al., "Chemical Inhibition of NAT10 Corrects Defects of Laminopathic Cells," SCIENCE, 344(6183):527-532 (2014).
M. Singh et al., "Lamin A/C Depletion Enhances DNA Damage-Induced Stalled Replication Fork Arrest," Molecular and Cellular Biology, 33(6)1210-1222 (2013).

* cited by examiner

*Primary Examiner* — Emily Bernhardt
(74) *Attorney, Agent, or Firm* — Heslin Rothenberg Farley & Mesiti P.C.

(57) ABSTRACT

The invention relates to compounds in the treatment or prevention of disorders associated with Lamin A and/or Lamin C depletion or LMNA mutations, such as laminopathy, premature ageing disorders, normal ageing and cancer (such as a cancer characterized by low levels of LMNA expression).

20 Claims, 29 Drawing Sheets

A

B

PK Parameters and Plasma Concentration(ng/mL) for Remodelin

| | |
|---|---|
| $T_{1/2}$ (hr) | 1.81 |
| $T_{max}$ (hr) | 0.250 |
| $C_{max}$ (ng/mL) | 409 |
| $AUC_{0-t}$ (ng·hr/mL) | 235 |
| $AUC_{0-\infty}$ (ng·hr/mL) | 259 |
| MRT_last(hr) | 0.844 |
| Bioavailability(%) | 43.5% |

Study Details

| | |
|---|---|
| Compound ID | Remodelin |
| Strain/Species/Sex | ICR mouse/ male |
| Nominal Dose | 1  mg/kg IV |
| | 5  mg/kg PO |
| Formulation | 10% DMSO+ 90% (40% HP-β-CD) |
| Matrix | Plasma (EDTA-$K_2$) |

SEQUENCE LISTING

```
<160> NUMBER OF SEQ ID NOS: 11

<210> SEQ ID NO 1
<211> LENGTH: 25
<212> TYPE: RNA
<213> ORGANISM: Artificial
<220> FEATURE:
<223> OTHER INFORMATION: Synthetic RNAi

<400> SEQUENCE: 1
ccaugaagga ggaacuggac uucca                                             25

<210> SEQ ID NO 2
<211> LENGTH: 25
<212> TYPE: RNA
<213> ORGANISM: Artificial
<220> FEATURE:
<223> OTHER INFORMATION: Synthetic RNAi
```

<400> SEQUENCE: 2
gcgugaggag uuuaaggagc ugaaa                                    25

<210> SEQ ID NO 3
<211> LENGTH: 25
<212> TYPE: RNA
<213> ORGANISM: Artificial
<220> FEATURE:
<223> OTHER INFORMATION: Synthetic RNAi

<400> SEQUENCE: 3
gagcauggac cucucugaau acaua                                    25

<210> SEQ ID NO 4
<211> LENGTH: 48
<212> TYPE: DNA
<213> ORGANISM: Artificial
<220> FEATURE:
<223> OTHER INFORMATION: Synthetic Oligo

<400> SEQUENCE: 4
agcttgcggc cgccgccacc atggattaca aggatgacga cgataagg           48

<210> SEQ ID NO 5
<211> LENGTH: 48
<212> TYPE: DNA
<213> ORGANISM: Artificial
<220> FEATURE:
<223> OTHER INFORMATION: Synthetic Oligo

<400> SEQUENCE: 5
gatcccttat cgtcgtcatc cttgtaatcc atggtggcgg cggccgca           48

<210> SEQ ID NO 6
<211> LENGTH: 35
<212> TYPE: DNA
<213> ORGANISM: Artificial
<220> FEATURE:
<223> OTHER INFORMATION: Synthetic Oligo

<400> SEQUENCE: 6
gccggatcca tgcatcggaa aaaggtggat aaccg                         35

<210> SEQ ID NO 7
<211> LENGTH: 36
<212> TYPE: DNA
<213> ORGANISM: Artificial
<220> FEATURE:
<223> OTHER INFORMATION: Synthetic Oligo

<400> SEQUENCE: 7
cggacgcgtc tatttcttcc gcttcagttt catatc                        36

<210> SEQ ID NO 8
<211> LENGTH: 54
<212> TYPE: DNA
<213> ORGANISM: Artificial
<220> FEATURE:
<223> OTHER INFORMATION: Synthetic Oligo

<400> SEQUENCE: 8
ctgaaatcaa tggatttgag tgaatatatt atccgtgggg acgatgaaga gtgg    54

<210> SEQ ID NO 9

```
<211> LENGTH: 55
<212> TYPE: DNA
<213> ORGANISM: Artificial
<220> FEATURE:
<223> OTHER INFORMATION: Synthetic Oligo

<400> SEQUENCE: 9
ggataatata ttcactcaaa tccattgatt tcagcttccc tacttccttc ttgtg       55

<210> SEQ ID NO 10
<211> LENGTH: 33
<212> TYPE: DNA
<213> ORGANISM: Artificial
<220> FEATURE:
<223> OTHER INFORMATION: Synthetic Oligo

<400> SEQUENCE: 10
caagggatgg gctatgagag ccgtgctctg cag                               33

<210> SEQ ID NO 11
<211> LENGTH: 33
<212> TYPE: DNA
<213> ORGANISM: Artificial
<220> FEATURE:
<223> OTHER INFORMATION: Synthetic Oligo

<400> SEQUENCE: 11
ctgcagagca cggctctcat agcccatccc ttg                               33
```

NAT10 MODULATORS FOR TREATING OR PREVENTING LAMINOPATHIES, AGING AND CANCER

CROSS REFERENCE TO RELATED APPLICATIONS

This application is a national stage filing under section 371 of International Application No. PCT/GB2015/051040, filed on Apr. 2, 2015, and published on Oct. 8, 2015 as WO2015/150824, and claims priority to British Application No. 1405991.9, filed on Apr. 3, 2014. The entire disclosures of each of the prior applications are hereby incorporated herein by reference.

FIELD OF THE INVENTION

The invention relates to compounds in the treatment or prevention of disorders associated with Lamin A and/or Lamin C depletion or LMNA mutations, such as laminopathy, premature ageing disorders, normal ageing and cancer.

BACKGROUND OF THE INVENTION

The nuclear lamina, composed of A and B-type lamins, maintains nuclear morphology and functions as an anchoring platform for tethering chromatin T. Dechat et al. (2008) *Genes Dev.* 22, 832). Lamins interact with numerous chromatin-bound proteins and are also indirectly linked to the cytoskeleton, via transmembrane proteins including Nesprins and SUN proteins (M. Crisp et al. (2006) *J. Cell Bio.* 172, 41). Mutations in LMNA, which encodes Lamin A and C, cause a wide spectrum of human diseases known as laminopathies (H. J. Worman, G. Bonne (2007) *Exp. Cell Res.* 313, 2121). These include Emery-Dreifuss muscular dystrophy (AD-EDMD) (G. Bonne et al. (1999) *Nat. Genet.* 21, 285) and the severe accelerated-ageing disease Hutchinson Gilford Progeria Syndrome (HGPS) (A. De Sandre-Giovannoli et al. (2003) *Science* 300, 2055; M. Eriksson et al. (2003) *Nature* 423, 293). Deregulation of A-type lamins has also been observed in various human cancers, where they are aberrantly expressed or localized (J. L. Broers et al. (1993) *Am. J. Pathol.* 143, 211; S. F. Moss et al. (1999) *Gut* 45, 723; R. S. Venables et al. (2001) *Br. J. Cancer* 84, 512).

Lamin A/C depletion or LMNA mutations cause enlarged, misshapen nuclei associated with loss of global chromatin organization (G. Galiova et al. (2008) *Eur. J. Cell Biol.* 87, 291). The exact molecular causes for the broad range of clinical phenotypes associated with laminopathies, however, remain to be defined. While some of these pathologies might reflect the primary molecular defect in lamin disorganization causing cellular fragility (the "structural hypothesis"), many seem likely to result from downstream effects on chromatin structure, gene expression or additional nuclear processes such as replication, transcription and DNA repair (K. L. Wilson et al. (2001) *Cell* 104, 647). Interestingly, recent studies suggest that improving nuclear architecture of laminopathic cells can also ameliorate certain downstream defects in chromatin structure and other cellular processes, thus improving some disease-associated phenotypes (C. Y. Chen et al. (2012) *Cell* 149, 565; J. I. Toth et al. (2005) *PNAS* 102, 12873; M. Columbaro et al. (2005) *Cell Mol. Life Sci.* 62, 2669).

There is therefore a need to provide treatments which correct nuclear architecture defects and improve cellular fitness of laminopathic human cells, thereby treating laminopathies and premature ageing disorders.

SUMMARY OF THE INVENTION

According to a first aspect of the invention, there is provided a compound of formula (I):

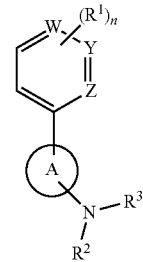

wherein:
each of W, Y and Z represent CH or one of W, Y and Z represents nitrogen and the other two groups represent CH;
Ring A represents:

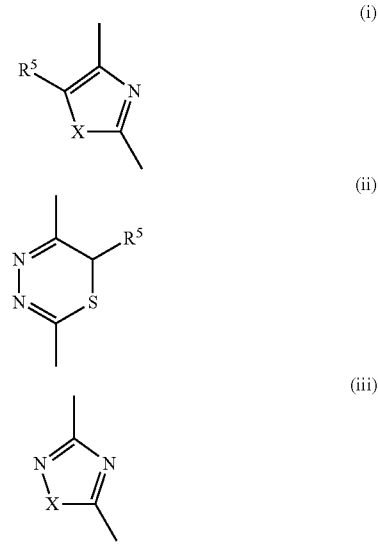

X represents S, O or $NR^a$;
$R^a$ represents hydrogen, hydroxyl, =O, $C_{1-6}$ alkyl, $C_{2-6}$ alkenyl, $C_{2-6}$ alkynyl, halogen, halo$C_{1-6}$alkyl, $C_{1-6}$ alkoxy or halo$C_{1-6}$ alkoxy;
$R^5$ represents hydrogen, hydroxyl, $C_{1-6}$ alkyl, $C_{2-6}$ alkenyl, $C_{2-6}$ alkynyl, halogen, halo$C_{1-6}$alkyl, $C_{1-6}$ alkoxy, halo$C_{1-6}$ alkoxy, COH, COOH, COOC$_{1-6}$alkyl, cyano, $NH_2$ or $NO_2$;
n represents an integer selected from 0 to 5;
each $R^1$ independently represents $C_{1-6}$ alkyl, $C_{2-6}$ alkenyl, $C_{2-6}$ alkynyl, halogen, halo$C_{1-6}$alkyl, $C_{1-6}$ alkoxy, halo$C_{1-6}$ alkoxy, cyano, hydroxyl, COH, COOH, COOC$_{1-6}$alkyl, $NH_2$ or $NO_2$;
$R^2$ represents hydrogen, $C_{1-6}$ alkyl, $C_{2-6}$ alkenyl or $C_{2-6}$ alkynyl;
$R^3$ is selected from either hydrogen or an —N=$R^4$ group, such that when Ring A represents formula (i) or (iii), $R^3$ represents —N=$R^4$, and when Ring A represents formula (ii), $R^3$ represents hydrogen;

R⁴ represents —C(R⁴ᵃ)(R⁴ᵇ), $C_{3-8}$ cycloalkyl, $C_{3-8}$ cycloalkenyl or benzyl wherein said cycloalkyl or benzyl is optionally substituted by $C_{1-6}$ alkyl, $C_{2-6}$ alkenyl, $C_{2-6}$ alkynyl, halogen, halo$C_{1-6}$alkyl, $C_{1-6}$ alkoxy, halo$C_{1-6}$ alkoxy, cyano, hydroxyl, COH, COOH, COO$C_{1-6}$alkyl, $NH_2$ or $NO_2$;

$R^{4a}$ and $R^{4b}$ are independently selected from hydrogen, $C_{1-6}$ alkyl, $C_{2-6}$ alkenyl, $C_{2-6}$ alkynyl, halogen, halo$C_{1-6}$alkyl, $C_{1-6}$ alkoxy, halo$C_{1-6}$ alkoxy, cyano, hydroxyl, COH, COOH, COO$C_{1-6}$alkyl, $NH_2$, $NO_2$, $C_{3-8}$ cycloalkyl or benzyl wherein said cycloalkyl or benzyl is optionally substituted by $C_{1-6}$ alkyl, $C_{2-6}$ alkenyl, $C_{2-6}$ alkynyl, halogen, halo$C_{1-6}$alkyl, $C_{1-6}$ alkoxy, halo$C_{1-6}$ alkoxy, cyano, hydroxyl, COH, COOH, COO$C_{1-6}$alkyl, $NH_2$ or $NO_2$;

or a pharmaceutically acceptable salt or solvate thereof, for use in the treatment or prevention of laminopathy, premature ageing disorders, normal ageing or cancer.

DETAILED DESCRIPTION OF THE INVENTION

Figure 1:
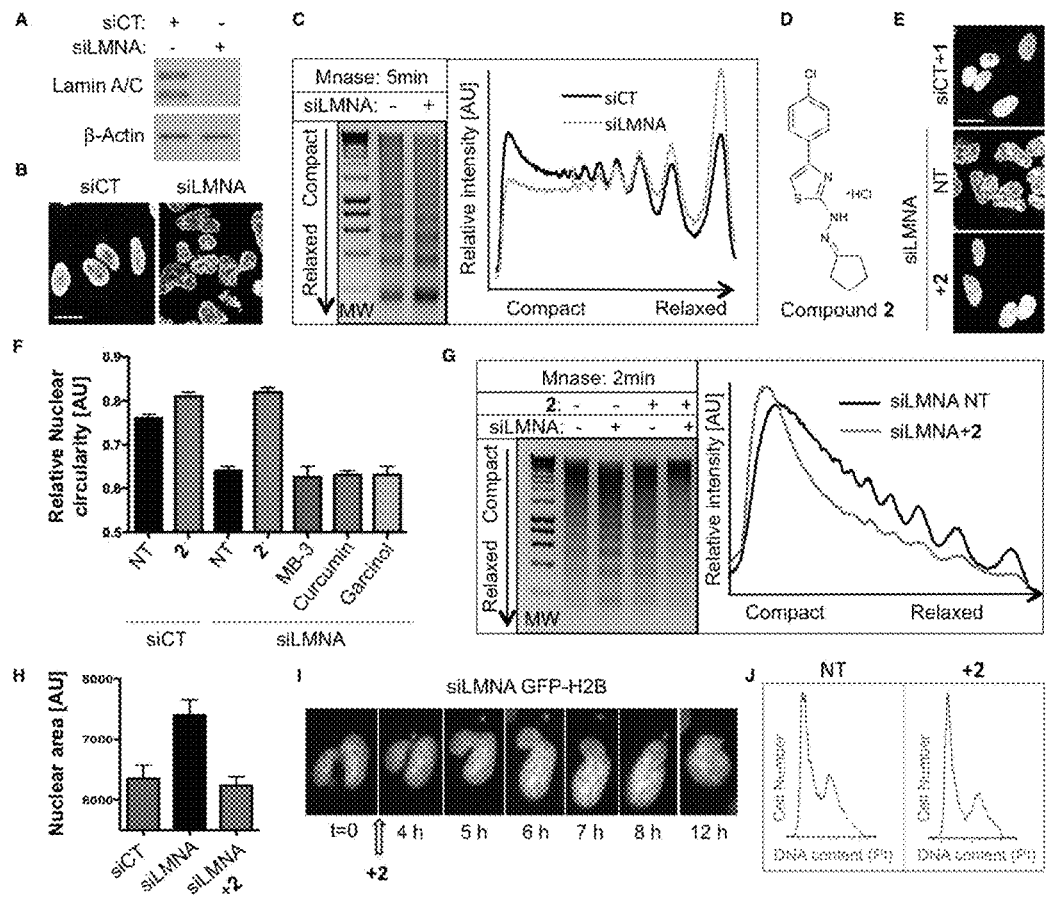
FIG. 1: Identification of a KAT inhibitor restoring nuclear shape and chromatin compaction in Lamin A/C depleted cells. A) Analysis of Lamin A/C depletion (siLMNA) in U2OS cells compared to negative control (siCT). B) Nuclear shape observed by DAPI staining. C) Representative MNase digestion profile (left) from three independent experiments and corresponding quantification (right). D) Molecular structure of cyclopentylidene-[4-(4'-chlorophenyl)thiazol-2-yl)hydrazone (Compound 2). E) Nuclear shape rescue observed by DAPI staining after treatment with Compound 2. F) Quantification of nuclear circularity in non-treated (NT) cells or cells treated with the indicated compounds (means of three independent experiments with n>212±s.d.). G) Representative MNase digestion profile (left) from three independent experiments and corresponding quantification of siLMNA cells (right). H) Quantification of nuclear area (means of three independent experiments with n>198±s.d.). I) Live imaging pictures of nuclear shape rescue in GFP-H2B expressing U2OS cells transfected with siLMNA and treated with Compound 2. J) Cell cycle profile analysed by flow cytometry. PI: propidium iodide. Scale bars: 20 μm.

According to one particular aspect of the invention which may be mentioned, there is provided a compound of formula (I):

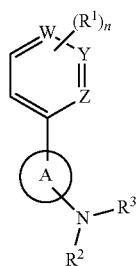

wherein:
each of W, Y and Z represent CH or one of W, Y and Z represents nitrogen and the other two groups represent CH;
Ring A represents:

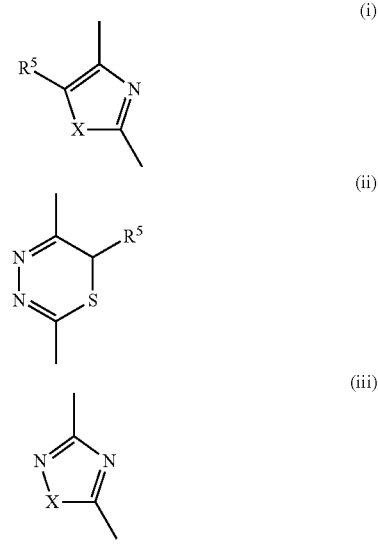

X represents S, O or $NR^a$;
$R^a$ represents hydrogen, hydroxyl, =O, $C_{1-6}$ alkyl, $C_{2-6}$ alkenyl, $C_{2-6}$ alkynyl, halogen, $haloC_{1-6}$alkyl, $C_{1-6}$ alkoxy or $haloC_{1-6}$ alkoxy;
$R^5$ represents hydrogen, hydroxyl, $C_{1-6}$ alkyl, $C_{2-6}$ alkenyl, $C_{2-6}$ alkynyl, halogen, $haloC_{1-6}$alkyl, $C_{1-6}$ alkoxy, $haloC_{1-6}$ alkoxy, COH, COOH, $COOC_{1-6}$alkyl, cyano, $NH_2$ or $NO_2$;
n represents an integer selected from 0 to 5;
each $R^1$ independently represents $C_{1-6}$ alkyl, $C_{2-6}$ alkenyl, $C_{2-6}$ alkynyl, halogen, $haloC_{1-6}$alkyl, $C_{1-6}$ alkoxy, $haloC_{1-6}$ alkoxy, cyano, hydroxyl, COH, COOH, $COOC_{1-6}$alkyl, $NH_2$ or $NO_2$;
$R^2$ represents hydrogen, $C_{1-6}$ alkyl, $C_{2-6}$ alkenyl or $C_{2-6}$ alkynyl;
$R^3$ is selected from either hydrogen or an —N=$R^4$ group, such that when Ring A represents formula (i) or (iii), $R^3$ represents —N=$R^4$, and when Ring A represents formula (ii), $R^3$ represents hydrogen;
$R^4$ represents —C($R^{4a}$)($R^{4b}$), $C_{3-8}$ cycloalkyl or benzyl wherein said cycloalkyl or benzyl is optionally substituted by $C_{1-6}$ alkyl, $C_{2-6}$ alkenyl, $C_{2-6}$ alkynyl, halogen, $haloC_{1-6}$alkyl, $C_{1-6}$ alkoxy, $haloC_{1-6}$ alkoxy, cyano, hydroxyl, COH, COOH, $COOC_{1-6}$alkyl, $NH_2$ or $NO_2$;
$R^{4a}$ and $R^{4b}$ are independently selected from hydrogen, $C_{1-6}$ alkyl, $C_{2-6}$ alkenyl, $C_{2-6}$ alkynyl, halogen, $haloC_{1-6}$alkyl, $C_{1-6}$ alkoxy, $haloC_{1-6}$ alkoxy, cyano, hydroxyl, COH, COOH, $COOC_{1-6}$alkyl, $NH_2$, $NO_2$, $C_{3-8}$ cycloalkyl or benzyl wherein said cycloalkyl or benzyl is optionally substituted by $C_{1-6}$ alkyl, $C_{2-6}$ alkenyl, $C_{2-6}$ alkynyl, halogen, $haloC_{1-6}$alkyl, $C_{1-6}$ alkoxy, $haloC_{1-6}$ alkoxy, cyano, hydroxyl, COH, COOH, $COOC_{1-6}$alkyl, $NH_2$ or $NO_2$;
or a pharmaceutically acceptable salt or solvate thereof, for use in the treatment or prevention of laminopathy, premature ageing disorders, normal ageing or cancer.

The term 'halo' or 'halogen' as used herein refers to fluorine, chlorine, bromine or iodine.

The term 'cyano' as used herein refers to a group where a carbon atom is triple-bonded to a nitrogen atom (i.e. —C≡N).

The term 'hydroxyl' as used herein refers to a group where an oxygen atom is bonded to a hydrogen atom.

The term '$C_{1-6}$alkyl' as used herein as a group or part of a group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term '$C_{2-6}$alkenyl' as used herein as a group or part of a group refers to a linear or branched hydrocarbon group containing from 2 to 6 carbon atoms and containing a carbon carbon double bond.

The term '$C_{2-6}$alkynyl' as used herein as a group or part of a group refers to a linear or branched hydrocarbon group having from 2 to 6 carbon atoms and containing a carbon carbon triple bond.

The term '$C_{1-6}$alkoxy' as used herein as a group or part of a group refers to an —O—$C_{1-6}$alkyl group wherein $C_{1-6}$alkyl is as defined herein. Examples of such groups include methoxy, ethoxy, propoxy, butoxy, and the like.

The term 'halo$C_{1-6}$alkyl' as used herein as a group or part of a group refers to a $C_{1-6}$ alkyl group as defined herein wherein one or more than one hydrogen atom is replaced with a halogen. The term 'halo$C_{1-6}$alkyl' therefore includes monohalo$C_{1-6}$alkyl and also polyhalo$C_{1-6}$alkyl. There may be one, two, three or more hydrogen atoms replaced with a halogen, so the halo$C_{1-6}$alkyl may have one, two, three or more halogens. Examples of such groups include fluoroethyl, fluoromethyl, trifluoromethyl or trifluoroethyl and the like.

The term 'halo$C_{1-6}$alkoxy' as used herein as a group or part of a group refers to a —O—$C_{1-6}$alkyl group as defined herein wherein one or more than one hydrogen atom is replaced with a halogen. The term 'halo$C_{1-6}$alkoxy' therefore includes monohalo$C_{1-6}$alkoxy, and also polyhalo$C_{1-6}$alkoxy. There may be one, two, three or more hydrogen atoms replaced with a halogen, so the halo$C_{1-6}$alkoxy may have one, two, three or more halogens. Examples of such groups include fluoroethyloxy, difluoromethoxy or trifluoromethoxy and the like.

The term '$C_{3-8}$ cycloalkyl' as used herein as a group or part of a group refers to a saturated hydrocarbon ring containing from 3 to 8 carbon atoms. Examples of such groups include cyclopropyl, cyclobutyl, cyclopentyl, cyclohexyl, cycloheptyl, cyclooctyl and the like.

The term 'benzyl' as used herein as a group or part of a group refers to a benzene ring attached to a $CH_2$ group.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

In one embodiment, each of W, Y and Z represent CH.

In one embodiment, Ring A represents formula (i) or (ii). In a further embodiment, Ring A represents formula (i). In an alternative embodiment, Ring A represents formula (ii). In a yet further alternative embodiment, Ring A represents formula (iii).

In one embodiment, X represents S or O. In a further embodiment, X represents S (i.e. a thiazole ring). In an alternative embodiment, X represents O (i.e. an oxazole ring).

In one embodiment, $R^5$ represents hydrogen or halogen (such as bromo). In a further embodiment, $R^5$ represents hydrogen.

In one embodiment, n represents an integer from 0 to 3. In one embodiment, n represents an integer from 1 to 2. In a further embodiment, n represents 1. In an alternative embodiment, n represents 2.

In one embodiment, $R^1$ represents cyano, hydroxyl, halogen (such as chloro or bromo), $C_{1-6}$alkoxy (such as methoxy), COOH, $NO_2$, halo$C_{1-6}$alkyl (such as trifluoromethyl) or halo$C_{1-6}$alkoxy (such as trifluoromethoxy). In a further embodiment, $R^1$ represents cyano, hydroxyl, halogen (such as chloro or bromo), $C_{1-6}$alkoxy (such as methoxy), COOH or $NO_2$. In a yet further embodiment, $R^1$ represents cyano, halogen (such as chloro or bromo) or $NO_2$, such as cyano or halogen. In a yet further embodiment, $R^1$ represents cyano. In a yet further alternative embodiment, $R^1$ represents halogen, such as chloro. In a yet further alternative embodiment, $R^1$ represents halo$C_{1-6}$alkyl, such as trifluoromethyl.

It will be understood by persons skilled in the art that the $R^1$ group may be attached in the para, ortho or meta positions on the phenyl ring of formula (I). In one embodiment, $R^1$ is in the 2, 3, or 4 position (i.e. ortho, meta or para position), in particular the meta (3) and/or para (4) position. In a further embodiment, $R^1$ is in the meta (3) position, for example when $R^1$ is halogen or cyano, in particular halogen. In an alternative embodiment, $R^1$ is in the para (4) position, for example when $R^1$ is cyano, chloro or trifluoromethyl.

In one embodiment, n represents 1 and said $R^1$ group is present on the 3 or 4 position on the phenyl ring of formula (I).

In one embodiment, n represents 1 and $R^1$ represents cyano, hydroxyl, halogen (such as chloro or bromo), $C_{1-6}$alkoxy (such as methoxy), COOH, $NO_2$ or halo$C_{1-6}$alkyl (such as trifluoromethyl). In a further embodiment, n represents 1 and $R^1$ represents cyano, hydroxyl, halogen (such as chloro or bromo), $C_{1-6}$alkoxy (such as methoxy), COOH or $NO_2$.

In one embodiment, n represents 2 and said $R^1$ group is present on the 2 and 4 or 3 and 4 or 2 and 3 positions on the phenyl ring of formula (I), such as the 2 and 4 or 3 and 4 positions.

In one embodiment, n represents 2 and both $R^1$ groups represent chloro (i.e. 3,4-dichloro) or $R^1$ represents $C_{1-6}$alkoxy (e.g. methoxy) and hydroxyl (i.e. 2-hydroxy-4-methoxy).

In an alternative embodiment, n represents 2 and both $R^1$ groups represent hydroxy (i.e. 3,4-dihydroxy).

In one embodiment, $R^2$ represents hydrogen or $C_{2-6}$alkynyl (such as ethynyl). In a further embodiment, $R^2$ represents hydrogen. In a further alternative embodiment, $R^2$ represents ethynyl.

In one embodiment, $R^3$ represents —N=$R^4$.

In one embodiment, $R^4$ represents —C($R^{4a}$)($R^{4b}$) (such as —C(Me)$_2$), unsubstituted $C_{3-8}$ cycloalkyl, unsubstituted $C_{3-8}$ cycloalkenyl or unsubstituted benzyl. In a further embodiment, $R^4$ represents unsubstituted $C_{3-8}$ cycloalkyl or unsubstituted benzyl.

In one embodiment, $R^4$ represents $C_{3-8}$ cycloalkyl, such as cyclopentyl or cyclohexyl (such as unsubstituted cyclopentyl or unsubstituted cyclohexyl). In a further embodiment, $R^4$ represents $C_{3-8}$ cycloalkyl, such as cyclopentyl (such as unsubstituted cyclopentyl).

In an alternative embodiment, R⁴ represents $C_{3-8}$ cycloalkenyl, such as cyclopentenyl or cyclohexenyl (such as unsubstituted cyclopentenyl or unsubstituted cyclohexenyl).

In one embodiment, R⁴ is optionally substituted by 1 or 2 groups, selected from $C_{1-6}$ alkyl, $C_{2-6}$ alkenyl, $C_{2-6}$ alkynyl, halogen, halo$C_{1-6}$alkyl, $C_{1-6}$ alkoxy, halo$C_{1-6}$ alkoxy or hydroxyl.

In one embodiment, the compound of formula (I) is selected from Compounds 1 to 21 or an alternative pharmaceutically acceptable salt, solvate, free acid preparation or free base preparation thereof. In a further embodiment, the compound of formula (I) is selected from Compounds 1 to 12 or an alternative pharmaceutically acceptable salt, solvate, free acid preparation or free base preparation thereof. In a yet further embodiment, the compound of formula (I) is selected from Compounds 1 to 11, such as Compounds 1 to 8, or an alternative pharmaceutically acceptable salt, solvate, free acid preparation or free base preparation thereof. In a yet further embodiment, the compound of formula (I) is selected from Compounds 1 to 3 or an alternative pharmaceutically acceptable salt, solvate, free acid preparation or free base preparation thereof.

In an alternative embodiment, the compound of formula (I) is a compound selected from: Compounds 1, 3, 4, 5, 6, 7 and 8, such as Compound 3 or 8 or an alternative pharmaceutically acceptable salt, solvate, free acid preparation or free base preparation thereof.

In one embodiment, the compound of formula (I) is 4-(4-cyanophenyl)-2-(2-cyclopentylidenehydrazinyl)thiazole (Compound 1) or a pharmaceutically acceptable salt, solvate, free acid preparation or free base preparation thereof.

In an alternative embodiment, the compound of formula (I) is 4-(4-chlorophenyl)-2-(2-cyclopentylidenehydrazinyl)thiazole or a pharmaceutically acceptable salt, solvate, free acid preparation or free base preparation thereof, such as the hydrochloride salt.

In an alternative embodiment, the compound of formula (I) is 4-(4-chlorophenyl)-2-(2-cyclopentylidene-1-(prop-2-yn-1-yl)hydrazinyl)thiazole (Compound 3) or a pharmaceutically acceptable salt, solvate, free acid preparation or free base preparation thereof.

In an alternative embodiment, the compound of formula (I) is 4-(4-trifluoromethylphenyl)-2-(2-cyclopentylidenehydrazinyl)thiazole (Compound 13) or a pharmaceutically acceptable salt, solvate, free acid preparation or free base preparation thereof, such as the hydrobromide salt.

According to a further aspect of the invention, there is provided a compound of formula (I)ᵃ:

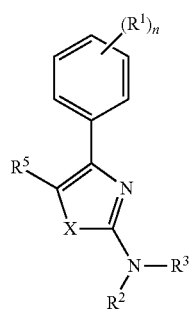

wherein $R^1$, $R^2$, $R^3$, $R^5$, X and n are as defined hereinbefore, for use in the treatment or prevention of laminopathy, premature ageing disorders, normal ageing or cancer.

According to a further aspect of the invention, there is provided a compound of formula (I)ᵇ:

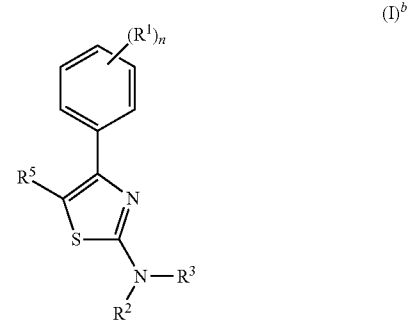

wherein $R^1$, $R^2$, $R^3$, $R^5$ and n are as defined hereinbefore, for use in the treatment or prevention of laminopathy, premature ageing disorders, normal ageing or cancer.

According to a further aspect of the invention, there is provided a compound of formula (I)ᶜ:

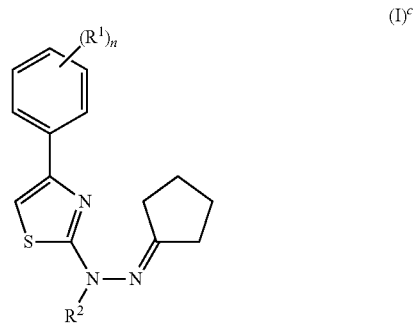

wherein $R^1$, $R^2$ and n are as defined hereinbefore, for use in the treatment or prevention of laminopathy, premature ageing disorders, normal ageing or cancer.

According to a further aspect of the invention, there is provided a compound of formula (I)ᵈ:

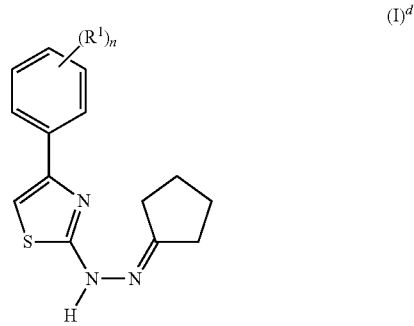

wherein $R^1$ and n are as defined hereinbefore, for use in the treatment or prevention of laminopathy, premature ageing disorders, normal ageing or cancer.

Certain compounds of formula (I) are novel, thus according to a further aspect of the invention, there is provided a compound of formula (I) selected from:

Compound 3, Compound 8, Compound 11, Compounds 13-17 and Compounds 19-21; and salts and solvates of any one thereof.

In one embodiment, the compound is selected from Compound 3 or 8.

NAT10 Inhibition

More generally, it will be understood that the inventors have discovered a novel link between NAT10 inhibition and improving nuclear architecture and chromatin organisation in Lamin A/C depleted cells or cells with LMNA mutations. Therefore, in a further aspect of the invention, there is provided a NAT10 inhibitor for use in the treatment or prevention of laminopathy, premature ageing disorders, normal ageing and cancer (such as a cancer characterised by low levels of LMNA expression), in particular, laminopathy and premature ageing disorders.

Figure 8:
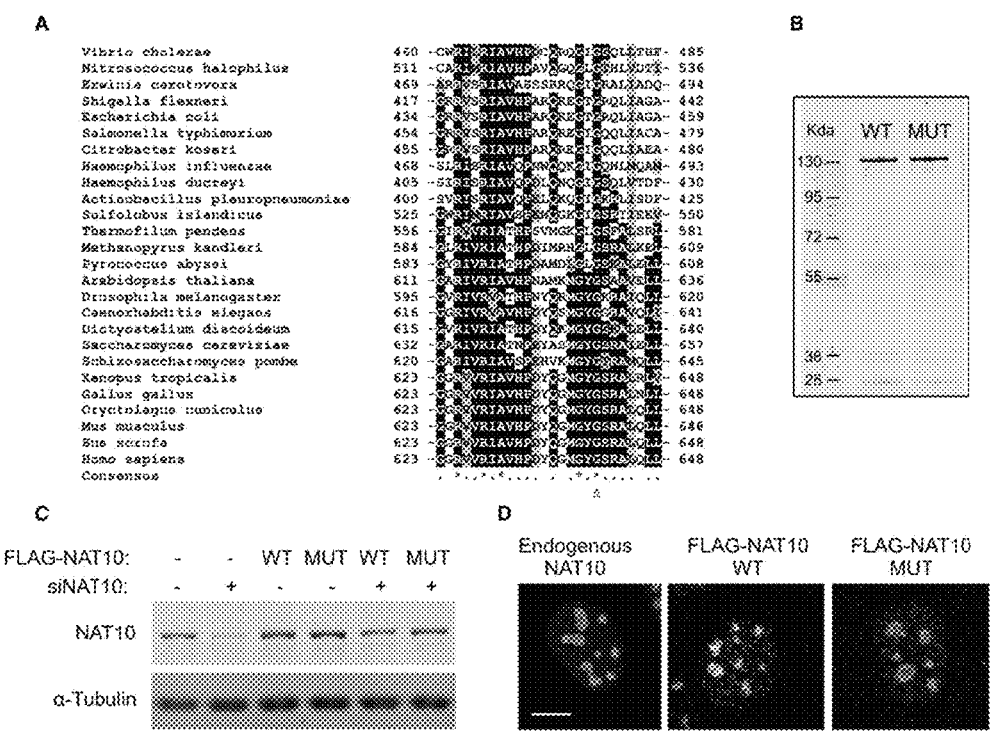
FIG. 8: NAT10 mutation G641E (MUT) does not affect its localization. A) Alignment of NAT10 GNAT (Gcn5-related N-acetyltransferase) domain showing the conservation of the G641 residue. B) Silver staining of purified FLAG-NAT10 WT or G641E mutant (MUT) from Human HEK293 cells. These proteins were used for the acetyl-transferase activity assay. C) Characterization of U2OS cells stably expressing siRNA resistant constructs of FLAG-NAT10 WT and MUT. The expression of the constructs and the resistance to siRNA was observed by western blotting and D) the correct localization of both constructs was verified by IF staining using anti-NAT10 antibody or anti-FLAG antibody. Scale bars: 10 μm.

N-acetyltransferase 10, also referred to as 'NAT10' (or initially as hALP), is a N-acetyltransferase enzyme that is highly conserved from bacteria to human (see FIG. 8). Mammalian NAT10 has been proposed to be a lysine acetyltransferase (KAT), while its bacterial homolog, TmcA, is a known RNA cytosine acetyltransferase (Chimnaronk et al. (2009) *Embo. J.* 28, 1362). KAT enzymes have the ability to modulate the acetylation status of histones and other proteins, thus affecting global chromatin organization. Therefore, references herein to the term 'NAT10 inhibitor' refer to molecules which are able to inhibit the acetyltransferase activity of NAT10. Known substrates of mammalian NAT10 are histones and tubulin (Shen et al. (2009) *Exp. Cell Res.* 315, 1653).

The inventors have identified small molecule inhibitors of NAT10 which result in nuclear morphology rescue via reorganization of the microtubule network. Thus, the identified small molecule inhibitors of NAT10 disclosed herein provide new opportunities to study laminopathy-associated processes with valuable spatial and temporal resolution, and can be used to alleviate laminopathies or diseases which cause premature ageing.

It will be apparent to persons skilled in the art that inhibition may occur either by binding to NAT10 directly or indirectly.

Methods of Screening

According to a further aspect of the invention, a method of screening for substances capable of inhibiting NAT10 activity is provided, as are NAT10 inhibitors and their use in therapy.

In light of the fact that the inventors have described a link between NAT10 inhibition and the treatment or prevention of laminopathy, premature ageing disorders, normal ageing or cancer, there is also provided a method of screening for a candidate drug substance intended to prevent or treat or prevent laminopathy, premature ageing disorders, normal ageing or cancer in a subject which comprises identifying a test substance capable of inhibiting NAT10 activity by measuring the effects of said test substance on NAT10 activity.

In one embodiment, the method of screening comprises:
a. contacting Lamin A and/or Lamin C depleted cells with a test substance;
b. measuring the level of NAT10 activity after a set period; and
c. comparing the level of NAT10 activity measured to that observed when no test substance is added.

In one embodiment, the method of screening is performed in vitro.

In one embodiment, the Lamin A and/or Lamin C depleted cells are obtained by using small interfering RNA (siRNA) to interfere with the expression of the LMNA gene. In a further embodiment, the Lamin A and/or Lamin C depleted cells are obtained by using siRNA duplexes of SEQ ID NOs: 1 and 2.

It will be appreciated by the person skilled in the art that the methods of screening provide concrete guidance for the identification of compounds capable of inhibiting NAT10 activity and rescuing nuclear shape defects.

Preparation of Compounds

In the present context, the term "pharmaceutically acceptable salt" is intended to indicate salts which are not harmful to the patient. Such salts include pharmaceutically acceptable acid addition salts, pharmaceutically acceptable metal salts and pharmaceutically acceptable alkaline addition salts. Acid addition salts include salts of inorganic acids as well as organic acids.

A reference to a compound of formula (I) and sub-groups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, prodrugs, isotopes and protected forms thereof as defined in any aspect of the invention (except intermediate compounds in chemical processes) are referred to as "compounds of the invention".

The compounds described herein include their use in the form of any and all stereoisomers (e.g. diastereoisomers and enantiomers as appropriate). For example, chiral compounds are claimed or claimed to be used as single enantiomers or mixtures of enantiomers (e.g. a racemic mixture).

Many compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt Where the compounds of formula (I) contain an amine function, these may form quaternary ammonium salts, for example by reaction with an alkylating agent according to methods well known to the skilled person. Such quaternary ammonium compounds are within the scope of formula (I).

It will be understood that the compounds of the invention may exist as mono- or di-salts.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci., Vol.* 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include hydrates thereof.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms.

The present invention includes all pharmaceutically acceptable isotopically-labelled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Processes for Preparing Compounds

According to a further aspect of the invention there is provided a process for preparing a compound of formula (I) as herein defined which comprises:

(a) when A represents (i), reacting a compound of formula (II)

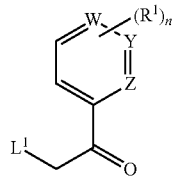

wherein W, Y, Z, $R^1$ and n are as defined hereinbefore and $L^1$ represents a suitable leaving group, such as chlorine or bromine; with a compound of formula (III):

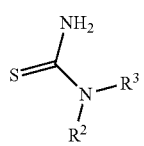

wherein $R^2$ and $R^3$ are as defined hereinbefore;

(b) deprotection of a protected derivative of a compound of formula (I); and/or (c) interconversion of a compound of formula (I) or protected derivative thereof to a further compound of formula (I) or protected derivative thereof; and (d) optional formation of a pharmaceutically acceptable salt of a compound of formula (I).

Process (a) typically comprises reacting a compound of formula (II) with a compound of formula (III) in the presence of a suitable solvent, such as isopropanol at a suitable temperature, such as room temperature for between 6 and 24 hours. It will be appreciated by the skilled person that preparation of compounds of formula (I) wherein A represents (ii) and (iii) may be made in an analogous manner to the procedure described in process (a).

It will be appreciated by those skilled in organic synthesis that two or more chemical steps in the schemes above may be run sequentially without isolation of intermediate materials.

Process (b) typically comprises any suitable deprotection reaction, the conditions of which will depend upon the nature of the protecting group. When the protecting group represents tBoc, such a deprotection reaction will typically comprise the use of a suitable acid in a suitable solvent. For example, the acid may suitably comprise trifluoroacetic acid or hydrogen chloride and the solvent may suitably comprise dichloromethane ethyl acetate, 1,4-dioxane, methanol or water. Optionally a mixture of solvents may be used, for example aqueous methanol or ethyl acetate/1,4-dioxane.

It will be appreciated that, when the protecting group represents tBoc, deprotection using a suitable acid as described above may generate a compound of formula (I) as a pharmaceutically acceptable salt, which may be isolated directly. Alternatively, the compound of formula (I) may be isolated as the free base using methods well known in the art and thereafter optionally converted to a pharmaceutically acceptable salt according to process (d).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)$CH_3$).

An aldehyde or ketone group may be protected, for example, as an acetal (R—CH$(OR)_2$) or ketal ($R_2$C$(OR)_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—$CH_3$); a benzyl carbamate (—NHCO—O$CH_2C_6H_5$, —NH-Cbz or NH—Z); as a t-butyl carbamate (—NHCO—OC$(CH_3)_3$, —NH-Boc); a 2-biphenyl-2-propyl carbamate (—NHCO—OC$(CH_3)_2$ $C_6H_4C_6H_5$, —NH-Boc), as a 9-fluorenylmethyl carbamate (—NH—Fmoc), as a 6-nitroveratryl carbamate (—NH—Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulphonyl)ethyl carbamate (—NH—Psec).

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

Process (c) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor compound to a compound of formula I and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

Process (d) may be carried out by treatment of a compound of formula (I) in the free base form, dissolved in a suitable solvent, with a stoichiometric amount or an excess of a pharmaceutically acceptable organic or inorganic acid, then isolation of the resulting salt by methods well known in the art, e.g. evaporation of solvent or crystallisation.

If appropriate, the reactions previously described in processes (a), (b) and (c) are followed or preceded by one or more reactions known to the skilled of the art and are performed in an appropriate order to achieve the requisite substitutions on $R^1$, $R^2$, $R^3$, $R^4$ and $R^5$ defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes, transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

Compounds of formula (II) may be prepared from compounds of formula (IV) in accordance with the following Scheme 1:

Scheme 1

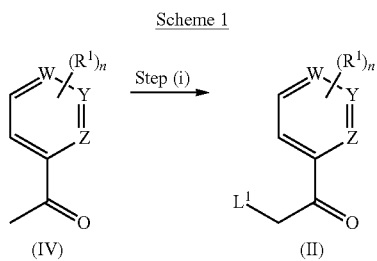

wherein W, Y, Z, $R^1$, n and $L^1$ are as defined hereinbefore.

Step (i) typically comprises the use of suitable reagents, such as 1.1 eq NXS, 1.5 eq pTSA and MeCN followed by heating to reflux for 2 to 24 hours.

It will be appreciated by the skilled person that compounds of formula (III) are either known or may be prepared from known materials in accordance with known procedures. For example, compounds of formula (V) where $R^2$ represents hydrogen and $R^3$ represents —N=cyclopropyl may be prepared in accordance with the following Scheme 2:

Scheme 2

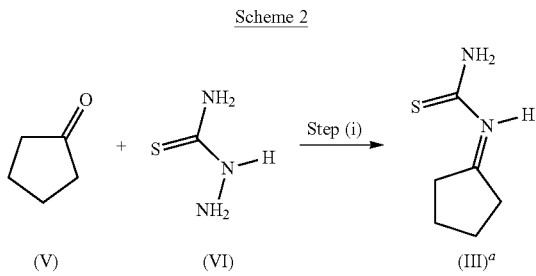

Step (i) typically comprises reacting compounds of formula (V) and (VI) in a suitable solvent such as isopropanol followed by heating to reflux for 16 hours.

The required intermediates, for example compounds of formula (IV), (V) and (VI) are either commercially available, known in the literature, prepared by methods analogous to those in the literature or prepared by methods analogous to those described in the example experimental procedures below.

Methods of Treatment

As discussed hereinabove, it is believed that compounds of the invention may be useful in the treatment or prevention of disorders associated with Lamin A and/or Lamin C depletion or LMNA mutations, such as laminopathy, premature ageing disorders, normal ageing and cancer, in particular, laminopathy and premature ageing disorders.

Therefore, according to a further aspect of the invention, there is provided compounds of the invention for use as a medicament, preferably a human medicament.

According to a further aspect the invention provides the use of compounds of the invention in the manufacture of a medicament for treating or preventing laminopathy, premature ageing disorders, normal ageing or cancer, in particular laminopathy or premature ageing.

According to a further aspect of the invention there is provided a method of treating or preventing laminopathy, premature ageing disorders, normal ageing or cancer in a human in need thereof comprising administering to said human a therapeutically effective amount of a compound as defined herein.

References herein to "laminopathy" refer to a group of genetic disorders which are caused by mutations in genes encoding proteins of the nuclear lamina, e.g. Lamin A/C depletion and/or defects in the LMNA gene. Laminopathies comprise dystrophic and progeric (i.e. premature ageing) diseases.

Examples of laminopathies include, but are not limited to: Atypical Werner syndrome; Barraquer-Simons syndrome; Buschke-Ollendorff syndrome; Cardiomyopathy; Charcot-Marie-Tooth disease; Emery-Dreifuss muscular dystrophy (X-linked (EDMD), autosomal dominant (EDMD2) or autosomal recessive (EDMD3)); Familial partial lipodystrophy of the Dunnigan type (FPLD); Greenberg dysplasia; Hutchinson-Gilford progeria syndrome (HGPS); Leukodystrophy, demyelinating, adult-onset, autosomal dominant (ADLD); Limb-girdle muscular dystrophy type 1B (LGMD1B); Lipoatrophy with diabetes, hepatic steatosis, hypertrophic cardiomyopathy, and leukomelanodermic papules (LDHCP); Mandibuloacral dysplasia with type A lipodystrophy (MADA); Mandibuloacral dysplasia with type B lipodystrophy (MADB); Pelger-Huet anomaly (PHA); Pelizaeus-Merzbacher disease; or Restrictive Dermopathy (RD).

References herein to "premature ageing" refer to a disorder that causes accelerated ageing in an individual. Such disorders may be referred to as "progeric disorders" and include: Hutchinson-Gilford progeria syndrome (HGPS); Werner syndrome; Bloom syndrome; Rothmund-Thomson syndrome; Cockayne syndrome; or Xeroderma pigmentosum.

LMNA down-regulation has also been reported in several types of cancer (see Zink et al. (2004) Nat. Rev.; Wu et al. (2009) J. Exp. Clin. Cancer Res.). The complete loss of Lamin A expression that is observed in some cancers suggests that lamins may act as tumour suppressors (J. L. Broers, et al., Am J Pathol 1993, S. F. Moss, et al., Gut 1999, R. S. Venables, et al., Br J Cancer 2001). Importantly, downregulation of Lamin A/C expression is correlated with cancer aggressiveness and poor prognosis (E. J. Belt, et al., European journal of cancer 2011, N. D. Willis, et al., PLoS One 2008, N. D. Willis, et al., Biochem Soc Trans 2008). Loss of a functional lamina at the inner nuclear membrane seems to contribute to misshapen nuclei of cancer cells. Moreover, decreased Lamin A/C expression is associated with softer nuclei that can squeeze more easily into small blood vessels, that could contribute to increase the invasive potential of these cancer cells. Therefore, since the compounds of the invention are able to improve nuclear shape of Lamin A/C depleted cells, it will be understood that the compounds of the invention may also be used to treat these cancers. Indeed, higher doses of the compounds reduce cancer cells invasion and migration as well as cell proliferation, in particular in cancer cells expressing low levels of Lamin A/C.

Examples of types of cancer which may be treated by the compounds described herein include, but are not limited to, breast, bowel, bladder, bone, brain, cervical, colon, endometrial, oesophageal, kidney, liver, lung, ovarian, pancreatic, prostate, skin, stomach, testicular, thyroid or uterine cancer, leukemia, lymphoma, myeloma or melanoma. Cancer stem cells might also be targeted by the compounds.

The term 'medicament' as used herein refers to a pharmaceutical formulation that is of use in treating, curing or improving a disease or in treating, ameliorating or alleviating the symptoms of a disease. A pharmaceutical formulation comprises a pharmacologically active ingredient in a form not harmful to the subject it is being administered to and additional constituents designed to stabilise the active ingredient and affect its absorption into the circulation or target tissue. In one embodiment, the medicament described herein is a human medicament.

It will be appreciated that references herein to "treatment" extend to prophylaxis, prevention of recurrence and suppression or amelioration of symptoms (whether mild, moderate or severe) as well as the treatment of established conditions.

Pharmaceutical Compositions

According to a further aspect, the invention provides a pharmaceutical composition comprising a compound of the invention, in association with one or more pharmaceutically acceptable carrier(s), diluents(s) and/or excipient(s) for use in the treatment or prevention of laminopathy, premature ageing disorders, normal ageing or cancer. The carrier, diluent and/or excipient must be "acceptable" in the sense of being compatible with the other ingredients of the composition and not deleterious to the recipient thereof.

The compounds of the invention may also be used in combination with one or more further active ingredients. The invention thus provides, in a further aspect, a combination comprising a compound of the invention or a pharmaceutically acceptable derivative thereof together with one or more further active ingredients.

When a compound of the invention or a pharmaceutically acceptable derivative thereof is used in combination with one or more further active ingredients against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The one or more further active ingredients can be active ingredients for the treatment or prevention of laminopathy, premature ageing disorders, normal ageing or cancer. Suitable non limiting examples of such active ingredients include: pravastatin, zoledronic acid, rapamycin, farnesyltransferase inhibitors such as lonafarnib, etc.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the one or more further active ingredients may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

Administration

The compound of the invention may be administered as the raw chemical but the active ingredient is preferably presented as a pharmaceutical formulation.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 1000 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

EXAMPLES

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

All solvents and reagents were purified using standard techniques or used as supplied from commercial sources (Sigma-Aldrich). NMR spectra were acquired on a Bruker 500 MHz instrument using deuterated solvents at 300 K. Notation for the $^1$H NMR spectral splitting patterns includes: singlet (s), doublet (d), triplet (t), broad (br) and multiplet/overlapping peaks (m). Signals are quoted as δ values in ppm and coupling constants (J) are quoted in Hertz. Mass spectra were recorded on a Micromass® Q-Tof (ESI) spectrometer.

General Procedure

The appropriate ketone or aldehyde was dissolved in isopropanol at a final concentration of 0.5 M and refluxed for 24 hours in the presence of an equimolar amount of thiosemicarbazide. The corresponding thiosemicarbazones were isolated by filtration and recrystallized from hot ethanol. Equimolar amounts of thiosemicarbazones and the desired haloketones were stirred at room temperature in isopropanol overnight at a final concentration of 0.2 M. The resulting products were recrystallized from hot ethanol several times to yield pure products and were used without further purification.

Compound 1

4-(4-Cyanophenyl)-2-(2-cyclopentylidenehydrazinyl)thiazole (Remodelin)

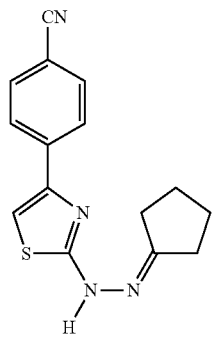 [SMILES: N#Cc1ccc(-c2csc(NN=C3CCCC3)n2)cc1]

2-Cyclopentylidenehydrazine-1-carbothioamide (which may be prepared as described in Scheme 2 hereinbefore) (1 g, 4.46 mmol) and 2-bromo-4'-cyanoacetophenone (which may be prepared as described in Scheme 1 hereinbefore) (700 mg, 4.45 mmol) were stirred overnight in 12 ml of isopropanol at room temperature. The precipitate was filtered and recrystallized from hot ethanol to yield the hydrobromide salt of the desired compound (559 mg, 1.98 mmol, 45%) as light yellow needles. This was resuspended in DMSO at a concentration of 10 mg/mL for use in cellular assays. $^1$H NMR (500 MHz, CDCl$_3$): δ 12.11 (br s), 7.84 (d, J=9.0 Hz, 2H), 7.81 (d, J=9.0 Hz, 2H), 6.84 (s, 1H), 2.61 (t, J=9.0 Hz, 2H), 2.51 (t, J=9.0 Hz, 2H), 1.94-1.80 (m, 4H); $^{13}$C NMR (125 MHz, CDCl$_3$): δ 173.8, 169.5, 138.8, 133.5, 131.3, 126.3, 118.0, 114.1, 103.8, 33.7, 31.2, 25.2, 25.0; HRMS (m/z): [M]$^+$ calcd. for C$_{15}$H$_{15}$N$_4$S, 283.1009; found, 283.1017.

Compound 2

4-(4-Chlorophenyl)-2-(2-cyclopentylidenehydrazinyl)thiazole Hydrochloride Salt

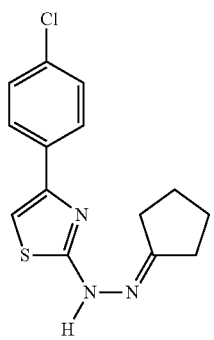

Thiosemicarbazide (20 g, 220 mmol) and cyclopentanone (19.43 ml, 220 mmol) were refluxed in 500 ml of isopropanol for 24 hours. The precipitate was filtered and recrystallized from hot ethanol to provide the corresponding thiosemicarbazone (2-cyclopentylidenehydrazine-1-carbothioamide) as pale yellow crystals. 2-cyclopentylidenehydrazine-1-carbothioamide (10 g, 63 mmol) and 2,4'-dichloroacetophenone (12 g, 63 mmol) were stirred overnight in 300 ml of isopropanol at room temperature. The precipitate was filtered and recrystallized from hot ethanol to yield the hydrochloride salt of the desired compound (16 g, 48 mmol, 77%) as light yellow needles. This was resuspended in DMSO at a concentration of 10 mg/mL for use in cellular assays. Spectral data were in agreement with those previously described in the literature (F. Chimenti et al., (2009) *J. Med. Chem.* 52, 530).

Compound 3

4-(4-Chlorophenyl)-2-(2-cyclopentylidene-1-(prop-2-yn-1-yl)hydrazinyl)thiazole

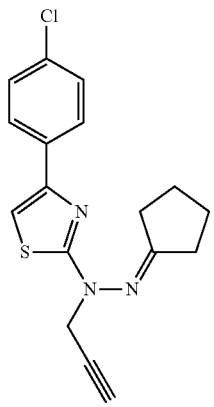 [SMILES: C#CCN(N=C1CCCC1)c1nc(-c2ccc(Cl)cc2)cs1]

To a solution of Compound 2 (1 g, 3 mmol) in freshly distilled DMF (75 ml) was added $K_2CO_3$ (1.375 g, 10 mmol), triethylamine (1.4 ml, 10 mmol) and propargyl bromide (1.2 ml, 5 mmol, 80 wt. % in toluene). The solution turned purple after 12 hours at room temperature. Propargyl bromide (1.2 ml) was added and the reaction mixture was stirred for another 12 hours. The solvent was then evaporated under reduced pressure and the crude residue dissolved in $CH_2Cl_2$, washed several times with saturated solutions of $NH_4Cl$ and NaCl and dried over $MgSO_4$. The solvent was evaporated under reduced pressure and the desired product (0.35 g, 1 mmol, 34%) was obtained as a brown oil after regular column chromatography. TLC (Hexane:$CH_2Cl_2$, 80:20): $R_f$=0.25; $^1$H NMR (500 MHz, CDCl$_3$): δ 7.78 (d, J=8.0 Hz, 2H), 7.32 (d, J=8.0 Hz, 2H), 6.86 (s, 1H), 4.65 (s, 2H), 2.64-2.55 (m, 4H), 2.22 (s, 1H), 1.86-1.82 (m, 4H); $^{13}$C NMR (125 MHz, CDCl$_3$): δ 184.9, 171.8, 150.6, 133.4, 133.3, 128.6 (2C), 127.3 (2C), 105.2, 78.3, 72.5, 42.7, 33.8, 31.5, 24.9, 24.4; HRMS (m/z): [M]$^+$ calcd. for $C_{17}H_{16}ClN_3S$, 329.0758; found, 329.0747.

It will be understood that Compounds 4-12 may be made in an analogous manner to Compounds 1 to 3, as described above:

| Compound | Structure |
|---|---|
| 2-(2-Cyclopentylidenehydrazinyl)-4-(3,4-dichlorophenyl)thiazole (Compound 4) | 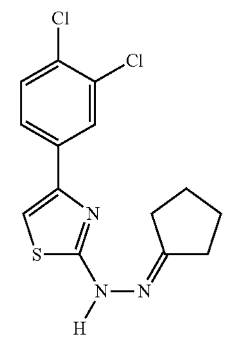 [SMILES: Clc1ccc(-c2csc(NN=C3CCCC3)n2)cc1Cl] |
| 2-(2-Cyclopentylidenehydrazinyl)-4-(3-nitrophenyl)thiazole (Compound 5) | 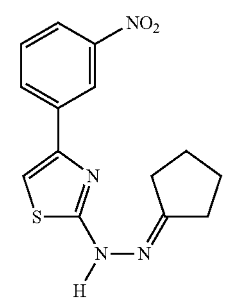 [SMILES: O=[N+]([O-])c1cccc(-c2csc(NN=C3CCCC3)n2)c1] |
| 4-(3-Chlorophenyl)-2-(2-cyclopentylidenehydrazinyl)thiazole (Compound 6) | 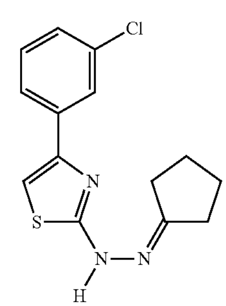 [SMILES: Clc1cccc(-c2csc(NN=C3CCCC3)n2)c1] |

| Compound | Structure |
|---|---|
| 4-(4-Bromophenyl)-2-(2-cyclopentylidenehydrazinyl)thiazole (Compound 7) | 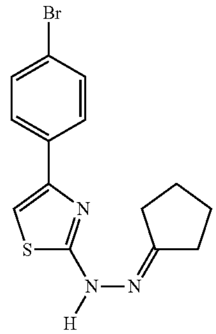 [SMILES: Brc1ccc(-c2csc(NN=C3CCCC3)n2)cc1] |
| 3-(2-(2-Cyclopentylidenehydrazinyl)thiazol-4-yl)benzonitrile (Compound 8) | 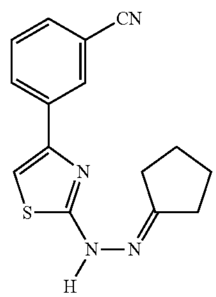 [SMILES: N#Cc1cccc(-c2csc(NN=C3CCCC3)n2)c1] |
| (Z)-2-(2-Benzylidenehydrazinyl)-4-(4-chlorophenyl)thiazole (Compound 9) | 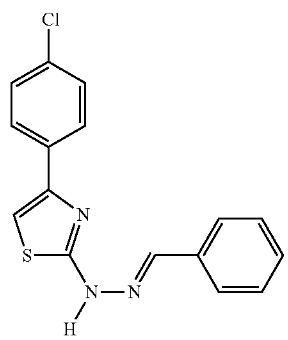 [SMILES: Clc1ccc(-c2csc(N/N=C/c3ccccc3)n2)cc1] |
| 2-(2-(2-Cyclopentylidenehydrazinyl)thiazol-4-yl)-5-methoxyphenol (Compound 10) | 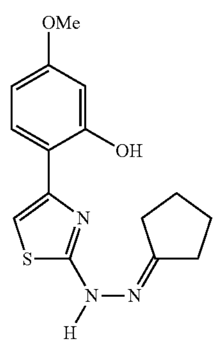 [SMILES: COc1ccc(-c2csc(NN=C3CCCC3)n2)c(O)c1] |
| 3-(2-(2-Cyclopentylidenehydrazinyl)thiazol-4-yl)benzoic acid (Compound 11) | 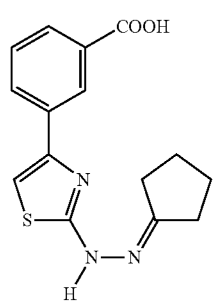 [SMILES: O=C(O)c1cccc(-c2csc(NN=C3CCCC3)n2)c1] |
| 5-(4-Chlorophenyl)-6H-1,3,4-thiadiazin-2-amine (Compound 12) | |

Compound 13

4-(4-Trifluoromethylphenyl)-2-(2-cyclopentylidene-hydrazinyl)thiazole Hydrobromide Salt 2-Cyclopentylidenehydrazine-1-carbothioamide (3.0 g, 18.7 mmol) and 2-bromo-4'-(trifluoromethyl)acetophenone (5.0 g, 18.7 mmol) were stirred in isopropanol (150 mL) at r.t. for 24 h. The precipitate was filtered and recrystallized three times from hot ethanol to yield the hydrobromide salt of the title compound as bright yellow needles (1.5 g, 3.7 mmol, 20%). 1H NMR (300 MHz, CDCl3) δ 11.12 (br s, 2H), 7.80 (d, J=8.5 Hz, 2H), 7.65 (d, J=8.5 Hz, 2H), 6.87 (s, 1H), 2.53 (t, J=7.0 Hz, 2H), 2.47 (t, J=7.0 Hz, 2H), 1.93-1.75 (m, 4H). 13C NMR (75 MHz, CDCl3) δ 171.9, 169.4, 140.3, 131.8 (q, J=32.0 Hz), 131.6, 126.5 (br q, J=3.5 Hz, 2C), 126.1 (2C), 123.7 (q, J=274.0 Hz), 103.5, 33.5, 30.6, 25.1, 24.9. HRMS (m/z): [M+H]+ calcd. for C15H15F3N3S, 326.0933; found, 326.0950.

It will be understood that Compounds 14-21 may be made in an analogous manner to Compounds 1 to 3 and 13, as described above:

| Compound Number | Structure |
|---|---|
| Compound 14 | 4-(3,4-dihydroxyphenyl)-thiazol-2-yl cyclopentylidene hydrazide |
| Compound 15 | 2-cyanophenyl thiazole cyclopentylidene hydrazide |
| Compound 16 | 4-cyanophenyl thiazole cyclopentylidene hydrazide |
| Compound 17 | 4-cyanophenyl thiazole cyclohexenylidene hydrazide |
| Compound 18 | 4-cyanophenyl thiazole cyclohexylidene hydrazide |

-continued

| Compound Number | Structure |
|---|---|
| Compound 19 | 4-(trifluoromethoxy)phenyl thiazole cyclopentylidene hydrazide |
| Compound 20 | 4-cyanophenyl 5-bromothiazole cyclopentylidene hydrazide |
| Compound 21 | 4-cyanophenyl thiazole isopropylidene hydrazide |

Experimental Data

Material and Methods

Cell Culture and Transfections

U2OS and SaOS-2 osteosarcoma cells, HeLa cervical cancer cells, A431 melanoma cells, NCI-SNU5 gastric cancer cells, MRC-5 lung fibroblast cells and Werner syndrome patient-derived SV40 fibroblast cells were grown in Dulbecco's modified Eagle medium (DMEM, Sigma-Aldrich) supplemented with 10% fetal bovine serum (BioSera), 2 mM L-glutamine, 100 U per ml penicillin, 100 μg ml$^{-1}$ streptomycin. Normal skin primary fibroblasts GM03440 and Hutchinson Gilford Progeria Syndrome (HGPS) skin primary fibroblasts AG11498 and AG06297 were purchased from Coriell Cell Repositories and used between passage number 9-12 and 20-23 respectively. Cells were grown in DMEM supplemented as above. RPE-1 retinal pigment epithelial cells were grown in DMEM and Ham F12 mix medium supplemented as above and buffered with sodium bicarbonate. HMV-II melanoma cell line, 22RV1 prostate carcinoma cells, NCI-H82 and NCI-H69 lung carcinoma cells, and NCI-N87 gastric cancer cell lines were grown in RPMI-1640 medium (Sigma-Aldrich) supplemented as above. Stably transfected U2OS cells were maintained in standard medium containing 1 mg ml$^{-1}$ G418 (Invitrogen). The siRNA duplexes were obtained from Life Sciences: Lamin A/C stealth RNAi: CCAUGAAGGAGGAACUG-GACUUCCA (SEQ ID NO: 1) and GCGUGAG-GAGUUUAAGGAGCUGAAA (SEQ ID NO: 2), NAT10 stealth RNAi: GAGCAUGGACCUCUCUGAAUACAUA (SEQ ID NO: 3), and as control siRNA, stealth RNAi negative control duplexes were used. Plasmid DNA and siRNA transfections were carried out using Lipofectamine 2000 and Lipofectamine RNAiMax (Life Sciences) respectively, following the manufacturer's instructions. Cells were analysed 48 to 72 hours after transfection.

Drug Treatments

The following KAT and KDAC inhibitors were used in the nuclear shape rescue screen, incubating cells with the molecules for 16 hours: trichostatin A (1 μM), sodium butyrate (5 mM), tubacin (10 μM), SAHA (5 μM), curcumin (10 μM), garcinol (50 μM), anacardic acid (1 μM), MB-3 (5 μM), 4-(4-chlorophenyl)-2-(2-cyclopentylidenehydrazinyl)thiazole (Compound 2) (50 μM), 4-(4-chlorophenyl)-2-(2-cyclopentylidene-1-(prop-2-yn-1-yl)hydrazinyl)thiazole (Compound 3) (50 μM) and cyclopentylidene-[4-(4-cyanophenyl)thiazol-2-yl)hydrazine (Compound 1) (Remodelin) (10 to 50 μM). For HGPS cellular fitness assays, Remodelin was incubated at 1 μM for 1 to 10 days, renewing the medium every 3 days. For long-term senescence assay, cells were kept and passaged in medium containing 1 μM Remodelin or DMSO only for 12 population doublings. Senescence was assessed after 8 days of Remodelin treatment when cells were at Population Doubling 12, and then after several weeks of Remodelin treatment, when cells reached Population Doubling 24 using the Senescence β-Galactosidase Staining Kit #9860 from Cell Signaling. Nocodazole, colchicine and latrunculin A (Sigma-Aldrich) were used at 200 ng/ml, 1 μg/ml and 1 μM respectively. Aphidicolin (Sigma-Aldrich) was used at 5 μg/ml for 16 h. Farnesyltransferase inhibitor FTI-277 was purchased from Tocris Bioscience and used at 5 μM. ATMi (KU55933) and ATRi (ATR-45) were obtained from Tocris Bioscience and from the Ohio State University respectively and used at 10 μM and 500 nM. Pifithrin alpha (Sigma-Aldrich) was used at 10 μM.

Live Imaging of GFP-H2B Cells

U2OS cells were transfected with siLMNA for 48 hours before addition of (Compound 2) at 50 μM. Pictures were acquired every 15 minutes for 16 hours in z-stack of 0.2 μm interval with a Deltavision PersonalDV (Applied Precision, 512×512 CoolSNAP HQ2 camera) equipped with a 100× UPlanSApo/1.40 oil objective (Olympus) and controlled with SoftWoRx software (Applied Precision). Movies were then assembled from pictures with ImageJ software.

Flow Cytometry

10 μM EdU was incubated for 2 hours when indicated. Cells were fixed in 4% paraformaldehyde (Sigma-Aldrich). EdU was fluorescently labeled using the Click-iT® EdU Flow Cytometry Assay Kit (Life Sciences). DNA was stained with 50 mg ml$^{-1}$ propidium iodide (Sigma-Aldrich) in phosphate buffer solution (PBS) containing 0.1% Triton-X-100 and 0.5 mg ml$^{-1}$ DNase free RNase A (Sigma-Aldrich). Samples were processed on a FACSCalibur flow cytometer equipped with CellQuest software (Becton Dickinson). Results were analysed using FlowJo software (TreeStar).

Nuclear Circularity and Nuclear Area Quantification

CellProfiler software was used to quantify nuclear circularity and nuclear area from DAPI staining pictures, using the "object size shape" measurement. The AreaShape measurement allowed the calculation of the Form Factor index (4×n×Area/Perimeter$^2$) corresponding to circularity (a Form Factor of 1 reflecting a perfect circle), as well as the calculation of nuclear Area.

Proliferation Assay

HGPS cells were plated at the same number in 24 well dishes. Next day, Remodelin (1 μM) or small molecule Compound 2 (1 to 10 μM), were added to the wells and plates were transferred into an IncuCyte microscope (Essen BioScience). Phase contrast pictures were acquired every 2 hours over several days. Percentage of cell confluence was calculated by the Cell Player integrated software (Essen BioScience) and analysed with GraphPad Prism® software.

Protein Purification from Human Cells

HEK293 cells were transiently transfected with NAT10 constructs and harvested after 48 hours in PBS. Cells were lysed for 5 minutes at room temperature in IP lysis buffer (20 mM Tris pH 7.5, 40 mM NaCl, 2 mM MgCl$_2$, 0.5% NP-40) freshly supplemented with 50 U/ml benzonase and EDTA-free protease inhibitor cocktail (Roche). After this initial lysis step, NaCl concentration was adjusted to 450 mM and samples were incubated at 4° C. with rotation. Lysates were clarified by centrifugation (13,200 rpm, 20 minutes at 4° C.), and after recovery NaCl concentration was equilibrated to 150 mM. Lysates were used for immunoprecipitation reaction in IP buffer (25 mM Tris pH 7.5, 150 mM NaCl, 1.5 mM DTT, 10% glycerol, 0.5% NP-40) supplemented with protease inhibitors. Target proteins were captured with anti-FLAG antibody (M2, Sigma-Aldrich) coupled to protein A/G-Dynabeads (Life Sciences). Complexes were washed with IP buffer containing incrementally increasing amounts of NaCl (250 mM, 500 mM, and 1M). Following this, the immuno-complexes were washed in TBS containing gradually decreasing amounts on NaCl (1M, 500 mM, 250 mM, and 150 mM). At this point, elution was carried out using excess triple-Flag peptide (Sigma Aldrich). Eluted proteins were loaded on a gel and the purification was verified by Silver Staining (SilverQuest kit, Life Sciences).

Analysis of Soluble or Polymerised Tubulin

U2OS cells pre-treated with 5 μM Remodelin for 16 hours or with 10 μM nocodazole for 8 hours, were lysed in MT Stabilization Buffer (MSB) (85 mM PIPES [pH 6.9], 1 mM EGTA, 1 mM MgCl$_2$, 2M glycerol, 0.5% Triton with 4 μg/ml Taxol). Lysates were kept at 4° C. for 2 minutes and then centrifuged for 10 minutes at 13,000 rpm. Supernatants, representing the soluble fraction of proteins, were transferred to new tubes, and Laemmli buffer was added. Pellets, representing the polymerized fraction of proteins, were washed once in MSB without Triton, and then resuspended in Laemmli buffer. Equal amounts of lysate were loaded on a gradient gel.

Microtubules Regrowth Assay 48 hours after siRNA transfections, microtubules were depolymerized by cold treatment at 4° C. for 1 hour in cells pre-treated or not with 5 to 10 μM Remodelin for 16 hours. Cold medium was replaced by pre-warmed medium and cells were incubated at 37° C. for 5 or 15 minutes to allow microtubules nucleation and anchorage respectively. Cells were fixed in PFA and stained with anti α-Tubulin antibody as described in the immunofluorescence procedure.

Immunoblotting

Total cell extracts were prepared by scraping cells in SDS lysis buffer (4% SDS, 20% glycerol, and 120 mM Tris-HCl, pH 6.8), boiling for 5 minutes at 95° C., followed by 10 strokes through a 25-gauge needle. Before loading, lysates were diluted with a solution of 0.01% bromophenol blue and 200 mM DTT and boiled for 5 minutes at 95° C. Proteins were resolved by SDS-PAGE on 4-12% gradient gels (NU-PAGE, Life Sciences) and transferred onto nitrocellulose membrane (Protran; Whatman). Secondary antibodies coupled to IRDye fluorophores were from LI-COR Biosciences. Detection and quantification was performed with an imager (Odyssey; LI-COR Biosciences).

Immunofluorescence

Cells were washed with PBS and fixed for 20 minutes with 2% PFA in PBS. Cells were permeabilised for 5 minutes with PBS/0.2% Triton X-100, and blocked with PBS/0.2% Tween 20 (PBS-T) containing 5% BSA. Coverslips were incubated for 1 hour with primary antibodies and for 30 minutes with appropriate secondary antibodies coupled to Alexa Fluor 488 or 594 fluorophores (Life Technologies), before being incubated with 2 µg/ml DAPI. Pictures were acquired with a FluoView 1000 confocal microscope (Olympus). For high resolution imaging, z-stacks were acquired with a Deltavision PersonalDV (Applied Precision, 1024×1024 CoolSNAP HQ2 camera, z-stack of 0.2 µm interval) or with a Deltavision OMX V3 in conventional mode (Applied Precision, 512×512 Cascade II cameras (Photometrics), z-stack of 0.125 µm interval) both equipped with a 100× UPlanSApo/1.40 oil objective (Olympus) and controlled with SoftWoRx software (Applied Precision). Deconvolutions were then performed with SoftWoRx (Applied Precision) in conservative mode. The different channels were acquired sequentially.

Fluorescent Labelling of Clickable Molecules

Cells were pre-incubated with clickable molecules Compound 3 or Reference Compound A (1-Chloro-4-ethynilbenzene, purchased from Sigma-Aldrich) for 2 hours before being fixed and permeabilised as described above. Click reaction was prepared using Invitrogen Click-iT reagents with Alexa fluor 488 Azide and incubated with fixed cells for 1 hour in the dark. In case of co-labelling with another protein, the click reaction was performed before the antibody incubations.

Antibodies

The antibodies used in this study are:

| Abcam antibodies: |
| --- |
| Lamin A/C ab40567 |
| HMG1 ab18256 |
| H2AX total ab11175 |
| Histone H3 ab1791 |
| β-actin ab8226 |
| ATM (phospho S1981) ab81292 |
| SUN1 ab124770 |
| anti-Giantin ab24586 |
| α-tubulin T9026 |
| H3K9me3 ab8898 |
| Sigma-Aldrich antibodies: |
| α-tubulin FITC F2168 |
| FLAG F3165 |
| Santa Cruz antibodies: |
| Lamin A/C sc-6215 |
| p53 (DO-1) sc-126 |
| p21 sc-397 |
| Cell Signaling antibodies: |
| γH2AX 2577 |
| p-Rb (Ser 807/811) 9308 |
| Rb 9309 |
| p-p53 (Ser15) 9284 |
| Others: |
| γH2AX 05-636 Millipore |
| NAT10 13365-1-AP ProteinTech |

Micrococcal Nuclease Digestion Sensitivity Assay $1 \times 10^6$ cells were trypsinized, harvested, and washed once with 1 ml of 1×RSB buffer (10 mM Tris, pH 7.6, 15 mM NaCl, and 1.5 mM $MgCl_2$). After centrifugation (3.00×g), the cell pellet was resuspended in 1 ml of 1×RSB buffer with 1% Triton-X 100 and homogenized by five strokes with a loose-fitting glass pestle to release nuclei. Nuclei were collected by centrifugation (13,000×g) and washed twice with 1 ml of buffer A (15 mM Tris, pH 7.5, 15 mM NaCl, 60 mM KCl, 0.34 M sucrose, 0.5 mM spermidine, 0.15 mM spermine, 0.25 mM PMSF, and 0.1% β-mercaptoethanol). Nuclei were resuspended in Buffer A and aliquoted into 100 µl aliquots. 1.2 µl of 0.1 M $CaCl_2$ was added to each aliquot and nuclei were digested by addition of 0.25 µl of 200 U/ml MNase (Sigma-Aldrich) and incubated at 30° C. Each aliquot was put back on ice at different time points and digestion was immediately stopped by addition of 3 µl EDTA. DNA was purified using the Qiagen PCR purification kit and 1500 ng of DNA was analysed on a 1.5% agarose gel. Digestion profiles were analysed using ImageJ and values were adjusted relative to the global intensity of each lane to compensate for DNA loading variations.

Lysine Acetyltransferase (KAT) Assay

The KAT assay was performed using the Fluorescent HAT Assay kit (Active Motif) using NAT10 purified from HEK293 cells and 5 µg of purified MAP enriched porcine tubulin (Tebu-bio) as a substrate. Remodelin and clickable molecule 2 were used at 50 µM.

Circular Dichroism (CD) Spectroscopy

CD experiments were performed using a Chirascan Circular Dichroism Spectrophotometer (Applied Photophysics, UK). 200 µl of purified FLAG-NAT10 at a final concentration of 10 µM in TBS 0.1% NP-40 (Sigma-Aldrich) was placed in a quartz cuvette with an optical path length of 1 mm, transferred to the spectrophotometer. CD scans were recorded at 25° C. over the wavelength range of 180 to 350 nm with a 1 second response time, 1 nm pitch and 1.5-nm bandwidth. Compound 2 solubilized in DMSO was added and the solution was incubated for 5 minutes before recording scans. CD spectra were buffer subtracted, zero corrected at 300 nm and normalized (Molar ellipticity e is quoted in $10^5$ deg $cm^2$ $dmol^{-1}$).

DNA Manipulations

All DNA constructs were validated to be mutation-free by DNA sequencing. A list of DNA oligonucleotides used in this study is provided below. pICE-FLAG was generated by cloning annealed primers FLAG-S and FLAG-AS into HindIII- and BamHI-digested pICE, a new synthetic plasmid conferring puromycin-resistance to mammalian cells (Britton S, Coates J, Jackson S P. J Cell Biol. 2013). To generate NAT10 cDNA resistant to NAT10 siRNA, NAT10 cDNA was amplified from IMAGE clone 5166101 (Source Bioscience) using primer pairs NAT10-F and NAT10-siR-R, or NAT10-siR-F and NAT10-R. The resulting PCR products were fused together by PCR using primers NAT10-F and NAT10-R. The resulting PCR product was digested with BamHI and MluI and cloned into pICE-FLAG digested with the same restriction enzymes. To generate pICE-FLAG-NAT10-G641E, the G641E mutation was introduced into pICE-FLAg-NAT10 using QuickChange Site-Directed Mutagenesis kit (Agilent Technologies), according to the manufacturer's instructions and using primers NAT10-G641E-F and NAT10-G641E-R.

TABLE 1

List of DNA oligonucleotides

| Name | Sequence 5' to 3' | SEQ ID NO. |
|---|---|---|
| FLAG-S | AGCTTGCGGCCGCCGCCACCATGGATTACAAGG ATGACGACGATAAGG | 4 |
| FLAG-AS | GATCCCTTATCGTCGTCATCCTTGTAATCCATGGT GGCGGCGGCCGCA | 5 |
| NAT10-F | GCCGGATCCATGCATCGGAAAAAGGTGGATAAC CG | 6 |
| NAT10-R | CGGACGCGTCTATTTCTTCCGCTTCAGTTTCATAT C | 7 |
| NAT10-siR-F | CTGAAATCAATGGATTTGAGTGAATATATTATCC GTGGGGACGATGAAGAGTGG | 8 |
| NAT10-siR-R | GGATAATATATTCACTCAAATCCATTGATTTCAGC TTCCCTACTTCCTTCTTGTG | 9 |
| NAT10-G641E-F | CAAGGGATGGGCTATGAGAGCCGTGCTCTGCAG | 10 |
| NAT10-G641E-R | CTGCAGAGCACGGCTCTCATAGCCCATCCCTTG | 11 |

Small Molecules for Protein Pull-Down Assays

Biotinylated derivative was synthesized from Compound 3 ("biotinylated Compound 3") using commercially available O-(2-aminoethyl)-O'-(2-azidoethyl)heptaethylene glycol and (+)-biotin N-hydroxysuccinimide. Further biotinylated derivatives of Compound 3 ("PEG4 biotinylated Compound 3") and control Reference Compound A ("PEG4 biotinylated Compound A") were generated in situ by addition of PEG4 carboxamide-6-azidohexanyl biotin (Life Sciences) and click reagents in cell extracts.

Biotinylated Small Molecule Pull-Downs

Cells were harvested in PBS and lysed in RIPA buffer supplemented with 1 mM PMSF and protease inhibitors (Roche) for 30 minutes at 4° C. with rotation. The supernatants were collected by centrifugation at 16,000×g for 10 minutes. Supernatants were then incubated with 40 μM of biotinylated small molecule (biotinylated Compound 3) or for the competition experiment with 200 μM of (Compound 2) and 40 μM of (biotinylated Compound 3) for 2 hours. Streptavidin coated magnetic beads (Dynabeads M-280 Streptavidin, Life Sciences) were washed 3 times with binding buffer (25 mM Tris.HCl, 150 mM NaCl, 0.1% Triton) and incubated with supernatants for 1 hour at 4° C. with rotation. The magnetic beads were washed 3 times with the binding buffer followed by boiling in Laemmli buffer for 5 minutes to elute the proteins. Samples were then loaded on 4-12% gradient gels (NUPAGE, Life Sciences), analyzed by silver staining (SilverQuest staining kit, Life Sciences) and specific bands were cut and analysed by LC-MS/MS.

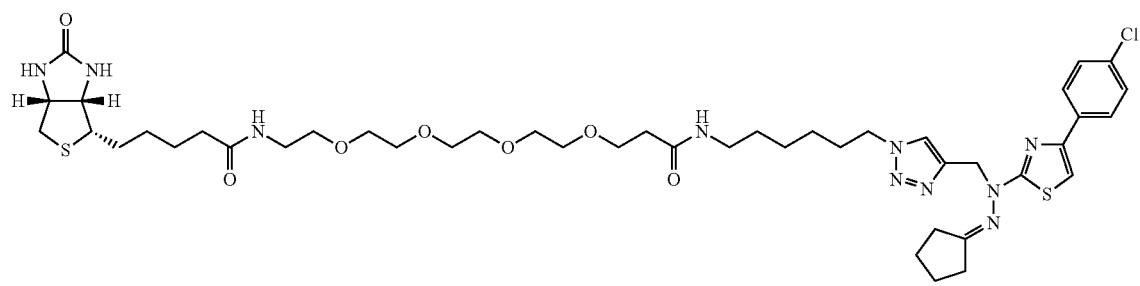

Compound 3

Biotinylated

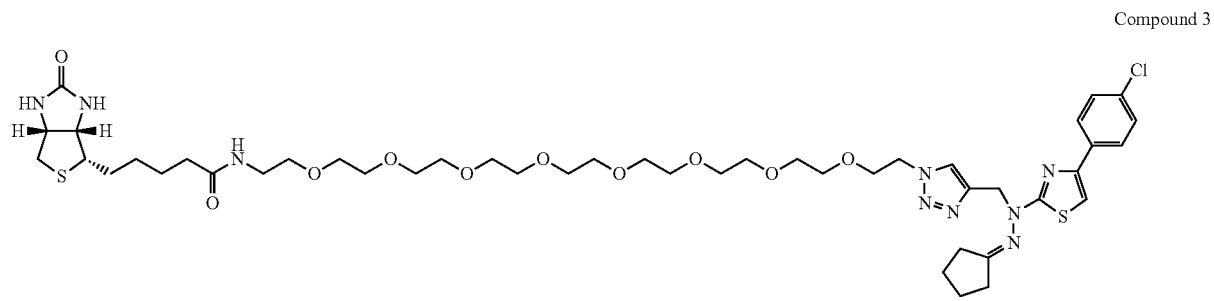

Compound 3

PEG4 biotinylated

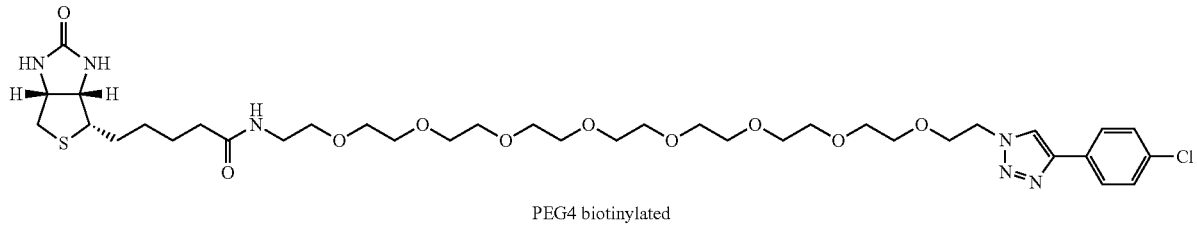

Compoun A

PEG4 biotinylated

Clickable Small Molecule Pull-Downs

PEG4 biotinylated Compound 3 was synthesized from Compounds 2, commercially available O-(2-aminoethyl)-O'-(2-azidoethyl)heptaethylene glycol and (+)-biotin N-hydroxysuccinimide, prior to being incubated with cell extracts (used in pull-down and mass spectrometry analyses).

Biotinylated Compound 3 and PEG4 biotinylated Compound A were generated in situ from Compounds 2 and 3, pre-incubated in live cells for 2 h prior to adding commercially available PEG4 carboxamide-6-azidohexanyl biotin and click reagents in cell extracts (used in click-pull-down and western blotting validation).

Click reaction reagents were added to the cell lysates as follows: 10 μM biotin azide (PEG4 carboxamide-6-Azidohexanyl Biotin, Life Sciences), 10 mM sodium ascorbate (Sigma-Aldrich), 2 mM $CuSO_4$ (Life Sciences). Click reactions were incubated in the dark for 1 hour at 4° C. with rotation. Streptavidin beads were then incubated for 1 hour and samples were eluted and loaded on a gel as described above, before immunoblotting.

Results

Example 1: Nuclear Shape Rescue by a KAT Inhibitor

Figure 2:
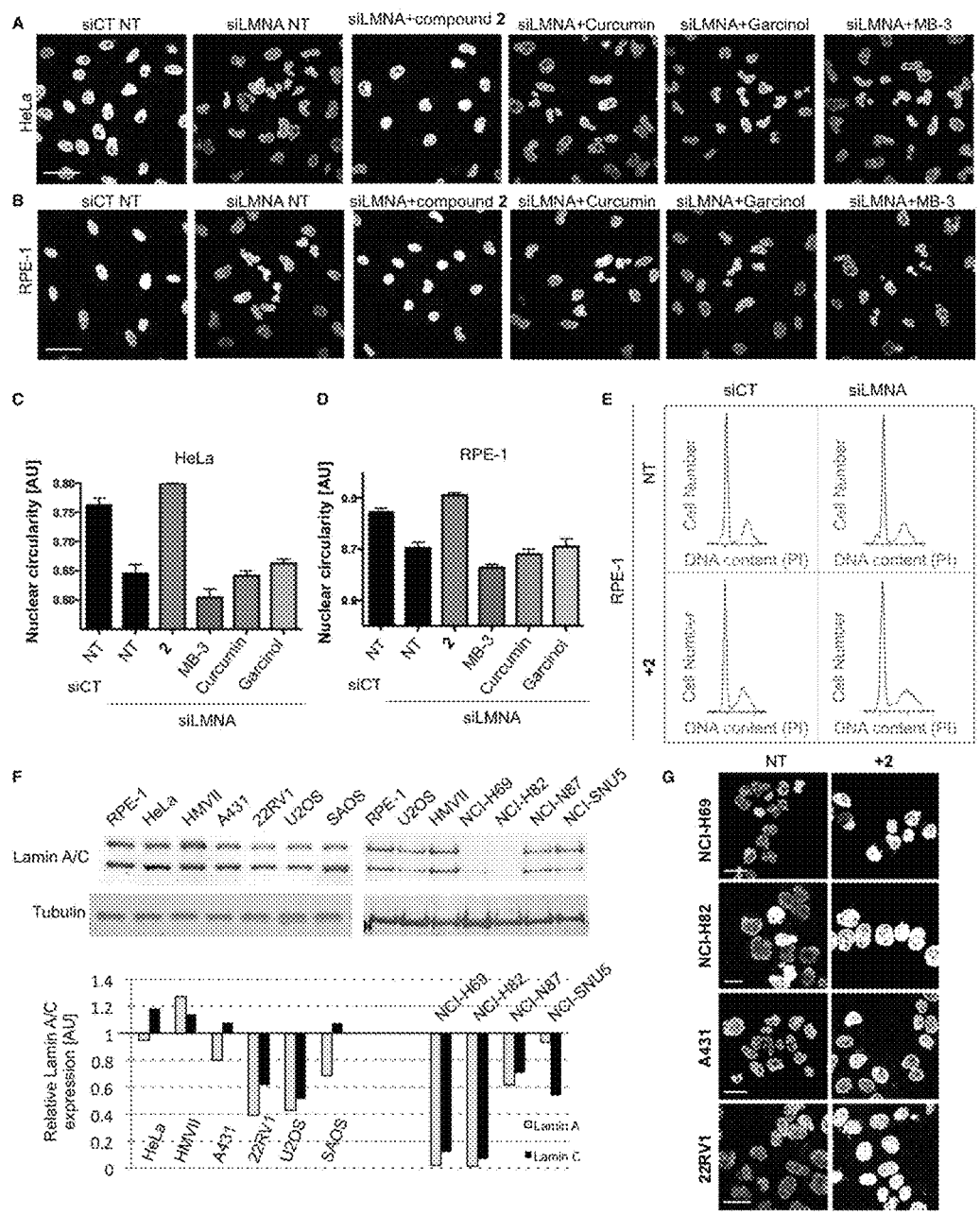
FIG. 2: Small molecule Compound 2 rescues nuclear shape defects in various Lamin A/C depleted cells. A) and B) Nuclear shape visualization by DAPI staining of HeLa (A) or RPE-1 (B) cells depleted for Lamin A/C (siLMNA) and treated with various KATi. Scale bars: 50 μm. C) and D) Cell Profiler quantification of nuclear circularity of HeLa (C) or RPE-1 (D) cells from DAPI staining as shown in A) and B) (means of three independent experiments with n>252±s.d). E) Cell cycle profile analysed by flow cytometry. PI: propidium iodide. F) Analysis of Lamin A/C expression levels in indicated cancer cell lines. Bottom panel: Image J quantification of Lamin A/C expression in cancer cells relative to normal RPE-1 cells. G) Representative pictures of DAPI staining showing nuclear shape improvement in low Lamin A/C expressing cancer cells after treatment with Compound 2. Scale bars: 20 μm.
Figure 3:
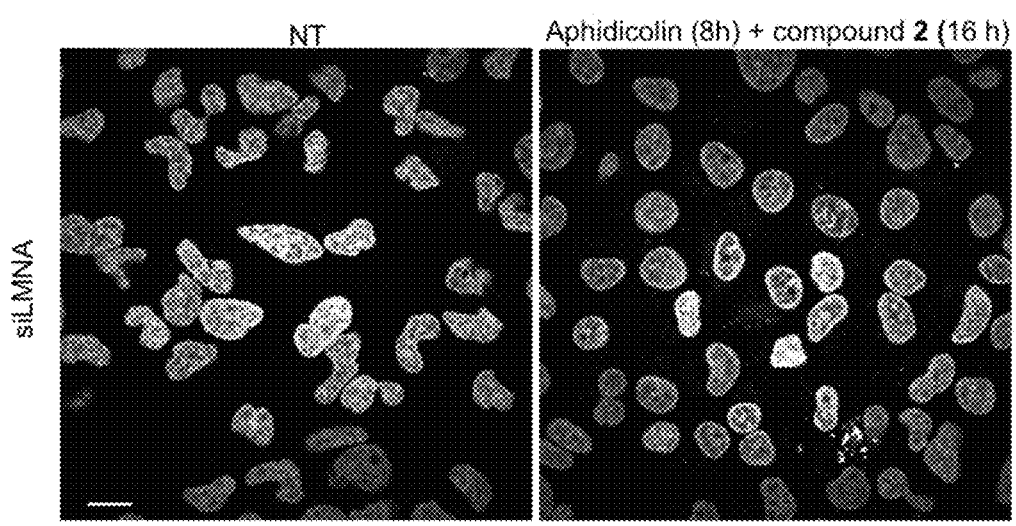
FIG. 3: Nuclear shape rescue of Lamin A/C depleted cells after treatment with Compound 2 is independent of mitosis. Nuclear shape rescue observed by DAPI staining in cells synchronized in S phase by aphidicolin and then treated with Compound 2 in the presence of aphidicolin to prevent mitotic entry. Scale bars: 20 μm.

Because lamin proteins act as a scaffold to maintain nuclear architecture and to anchor chromatin at the nuclear periphery (J. Gotzmann, R. Foisner (1999) *Crit. Rev. Eukaryot. Gene* Expr. 9, 257), small-interfering RNA (siRNA) mediated depletion of Lamin A/C (siLMNA) causes nuclear shape defects in various human cell lines (FIG. 1A, B and FIG. 2A, B). Notably, it was found that Lamin A/C depletion was also associated with global chromatin relaxation as observed by increased micrococcal nuclease (MNase) sensitivity and increased nuclear area (FIG. 1B, C). Thus, it was reasoned that re-compacting chromatin in Lamin A/C depleted cells might improve some of their nuclear architecture defects. Lysine acetyltransferase (KAT) and lysine deacetylase (KDAC) enzymes have the ability to modulate the acetylation status of histones and other proteins, thus affecting global chromatin organization. Therefore, the effects of various natural and synthetic small molecules (see Material and Methods) known to inhibit the activity of individual KAT or KDAC enzymes, were evaluated on chromatin compaction and nuclear shape of siLMNA cells. This identified the KAT inhibitor 4-(4-chlorophenyl)-2-(2-cyclopentylidenehydrazinyl)thiazole (Compound 2) (F. Chimenti et al., (2009) *J. Med. Chem.* 52, 530) (FIG. 1D) as completely restoring nuclear shape and circularity in various cell lines depleted of Lamin A/C (FIG. 1E, F and FIG. 2A-D). Despite small molecule Compound 2 having been initially identified as a GCN5 network inhibitor in *Saccharomyces cerevisiae* (F. Chimenti et al., (2009) *J. Med. Chem.* 52, 530), the classical GCN5 inhibitor MB-3 (M. Biel et al. (2004) *Angew. Chem. Int. Ed. Engl.* 43, 3974), did not improve nuclear circularity of siLMNA cells (FIG. 1F), suggesting that the small molecule-dependent nuclear shape rescue was independent of GCN5 inhibition. Molecule Compound 2 also improved global chromatin compaction in siLMNA cells as observed by decreased MNase sensitivity (FIG. 1G), and reduced nuclear area (FIG. 1H). By using cells expressing GFP-tagged histone H2B (GFP-H2B), it was observed by live imaging that complete nuclear shape rescue in siLMNA cells occurred within 12 hours upon treatment with Compound 2, independently of mitosis (FIG. 1I and FIG. 3) and without markedly affecting the cell cycle profile (FIG. 1J and FIG. 2E). Moreover, Compound 2 improved the nuclear morphology of several cancer cell lines displaying reduced Lamin A/C expression (FIG. 2F, G), indicating that the observed effects were not specific to siRNA-mediated Lamin A/C depletion.

Example 2: Protein Target Identification by Chemical Labelling of Compound 2

Figure 4:
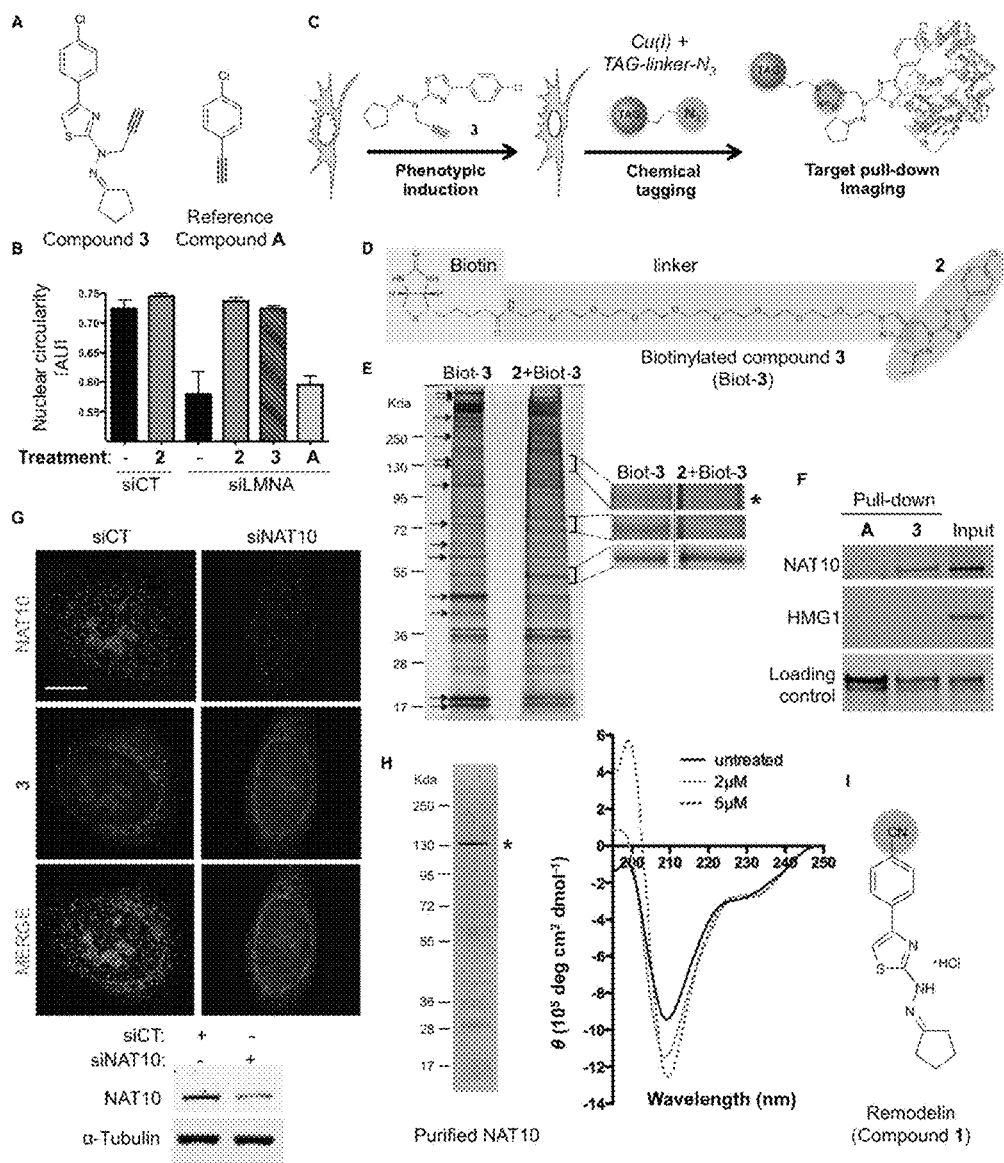
FIG. 4: The N-acetyltransferase NAT10 is a cellular target of small molecule Compound 2. A) Molecular structure of clickable analogue Compound 3 and clickable inactive control molecule Reference Compound A. B) Quantification of U2OS nuclear circularity (means of three independent experiments with n>224±s.d.) C) Principle of click-chemistry strategy for small molecule tagging. D) Molecular structure of biotinylated analogue of Compound 3. E) Silver staining of proteins after pull-down of small molecule biotinylated Compound 3 and identification of specific bands (see arrows) decreasing in the presence of 5 equivalents of non-clickable molecule Compound 2. The band corresponding to NAT10 is magnified on the right (*) together with other specific and non-specific bands. F) Pull-down of clickable molecules Compound 3 and Reference Compound A pre-incubated in U2OS cells and analysis of bound proteins. G) High resolution representative microscopy pictures of NAT10 (red) and fluorescently labeled Compound 3 (green) in control or NAT10 depleted cells (siNAT10) as observed by western blotting (bottom panel). Scale bars: 10 μm. H) Analysis of purified (silver staining, left) NAT10 folding by circular dichroism spectroscopy (right), showing the incremental effects of increasing concentrations of Compound 2 on NAT10 helical character. I) Molecular structure of Remodelin (Compound 1), a stable and potent analogue of Compound 2.

To identify putative biological targets of molecule Compound 2 and elucidate the mechanisms by which it improves nuclear morphology, a molecular-based strategy was established involving cellular functionalization of the molecule by means of "click chemistry" to retrieve and validate drug-associated protein complexes. To this end, an alkyne group was strategically introduced onto the hydrazone moiety of Compound 2, thereby producing "clickable" analogue Compound 3 (FIG. 4A) that exhibited equivalent cellular activity as Compound 2 (FIG. 4B), and used the inactive clickable molecule Reference Compound A as a negative control (FIG. 4A, B). While the alkyne moiety is biologically inert, it can selectively react with any molecule carrying an azide group upon copper exposure (V. V. Rostovtsev et al. (2002) *Angew. Chem. Int. Ed. Engl.* 41, 2596), thus allowing tagging of the small molecule in cells (FIG. 4C). As a first step, a biotinylated derivative of Compound 3 was generated (biotinylated Compound 3) (FIG. 4D) and incubated with cell extracts. Proteins associated with biotinylated Compound 3 were then retrieved with streptavidin beads and resolved by gel electrophoresis (FIG. 4E). Through carrying out competition experiments, several protein species were identified whose staining intensities were reduced in the presence of an excess of competitor Compound 2. Proteins selectively interacting with biotinylated Compound 3 by such competition criteria were then excised from gels and identified by mass spectrometry (LC-MS/MS).

Strikingly, N-acetyltransferase 10 (NAT10) was the only KAT protein identified by the above procedures (see Table 2), thus being the only likely relevant target of Compound 2.

TABLE 2

Biotin analogue of Compound 2 pulls-down the acetyl-transferase protein NAT10. Specific protein hits retrieved by small molecule biotinylated Compound 3 and identified by liquid chromatography-tandem mass spectrometry (LC-MS/MS).

| | Peptide Hits | Protein Name |
|---|---|---|
| Cytoskeleton | | |
| A2BDB0 | 21 | Gamma-actin |
| P15924 | 2 | Desmoplakin |
| P21333 | 8 | Filamin-A |
| Q14315 | 7 | Filamin-C |
| P35527 | 6 | Keratin, type I |
| Q5R844 | 3 | Myosin light polypeptide 6 |
| P48681 | 2 | Nestin |
| A6QQJ3 | 2 | Peripherin |
| Q15149 | 46 | Plectin |
| O94915 | 4 | Protein furry homolog-like |
| Q54HF0 | 4 | Putative actin-25 |
| Q9NYL9 | 3 | Tropomodulin-3 |
| P23729 | 2 | Type III intermediate filament |
| O43795 | 15 | Unconventional myosin-Ib |
| O00159 | 21 | Unconventional myosin-Ic |
| O94832 | 3 | Unconventional myosin-Id |
| P08670 | 52 | Vimentin |
| RNA/Nucleolus | | |
| Q3SZ63 | 2 | Nucleolar protein 56 |
| A4FUD3 | 3 | 116 kDa U5 small nuclear ribonucleoprotein component |
| Q1HR24 | 3 | 40S ribosomal protein S14 |
| Q76I82 | 3 | 40S ribosomal protein S15a |
| Q3T0X6 | 3 | 40S ribosomal protein S16 |
| Q6Q311 | 3 | 40S ribosomal protein S25 |
| Q4R5I3 | 2 | 60S ribosomal protein L22 |
| Q3T057 | 3 | 60S ribosomal protein L23 |
| Q3T0D5 | 2 | 60S ribosomal protein L30 |
| Q3T171 | 3 | 60S ribosomal protein L36 |
| Q02878 | 5 | 60S ribosomal protein L6 |
| Q99020 | 2 | Heterogeneous nuclear ribonucleoprotein A/B |
| A5A6H4 | 3 | Heterogeneous nuclear ribonucleoprotein A1 |
| Q6URK4 | 5 | Heterogeneous nuclear ribonucleoprotein A3 |
| Q5RA82 | 2 | Heterogeneous nuclear ribonucleoprotein C |
| Q14103 | 3 | Heterogeneous nuclear ribonucleoprotein D0 |
| Q4R4M6 | 6 | Heterogeneous nuclear ribonucleoprotein K |
| Q8VEK3 | 8 | Heterogeneous nuclear ribonucleoprotein U |
| Q2HJ60 | 8 | Heterogeneous nuclear ribonucleoproteins A2/B1 |
| Q9H0A0 | 8 | N-acetyltransferase 10 |
| Q9NR30 | 5 | Nucleolar RNA helicase 2 |
| Q3T160 | 2 | Nucleophosmin |
| Q08E38 | 2 | Pre-mRNA-processing factor 19 |
| A1A5S1 | 3 | Pre-mRNA-processing factor 6 |
| Q5RAS1 | 3 | pre-rRNA processing protein FTSJ3 |
| Q4R6M5 | 16 | Probable ATP-dependent RNA helicase DDX5 |
| Q9D903 | 2 | Probable rRNA-processing protein EBP2 |
| Q28009 | 5 | RNA-binding protein FUS |
| Q9UKM9 | 8 | RNA-binding protein Raly |
| O75691 | 41 | Small subunit processome component 20 homolog |
| Chromatin | | |
| Q91ZW3 | 2 | SWI/SNF-related matrix-associated actin-dependent regulator of chromatin subfamily A member 5 |
| Q9QZQ8 | 3 | Core histone macro-H2A.1 |
| Q8CCK0 | 2 | Core histone macro-H2A.2 |
| Q6URC2 | 3 | High mobility group protein HMG-I/HMG-Y |
| P0C0S8 | 3 | Histone H2A type 1 |
| A9UMV8 | 3 | Histone H2A.J |
| P02272 | 3 | Histone H2A.V |
| Q2M2T1 | 4 | Histone H2B type 1-K |
| P18437 | 2 | Non-histone chromosomal protein HMG-17 |
| Nuclear Envelope | | |
| Q5SRE5 | 4 | Nucleoporin NUP188 homolog |
| P20700 | 5 | Lamin-B1 |
| Q03252 | 22 | Lamin-B2 |
| Trafficking | | |
| Q6P5F9 | 4 | Exportin-1 |
| Q9EPL8 | 2 | Importin-7 |
| Other | | |
| P46940 | 2 | Ras GTPase-activating-like protein IQGAP1 |
| Q86VI3 | 4 | Ras GTPase-activating-like protein IQGAP3 |

Figure 5:
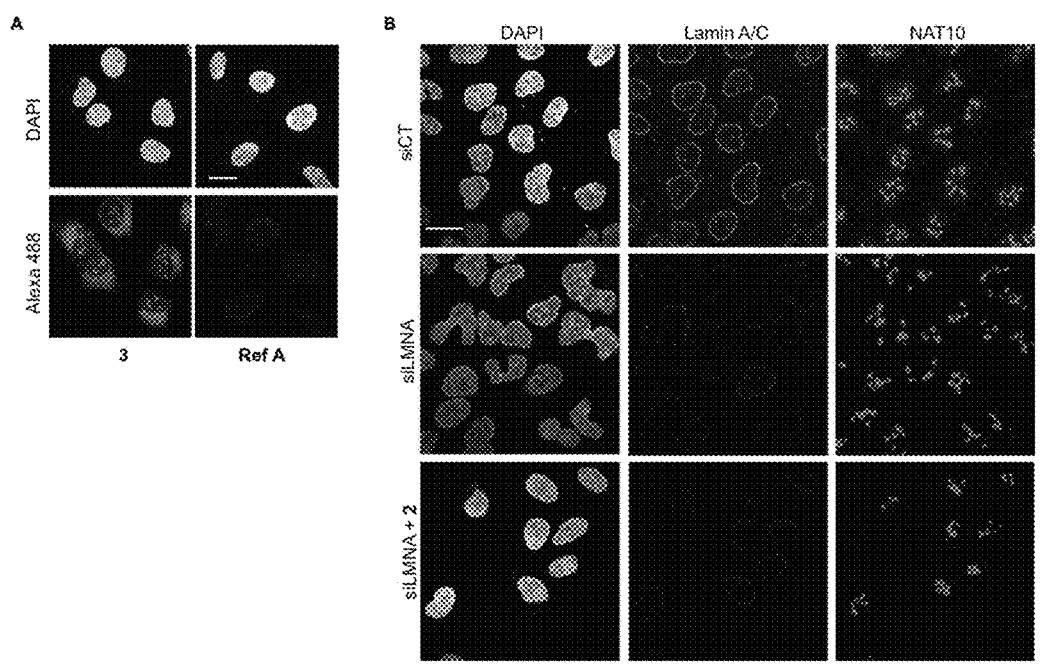
FIG. 5: Subcellular localization of the molecules and analysis of their effects on NAT10 localization. A) Fluorescent labelling of clickable control molecule Reference Compound A showing no specific staining, contrary to molecule Compound 3 (see FIG. 2). Scale bar: 20 μm. B) IF pictures of Lamin A/C and NAT10 staining within cells transfected or treated as indicated. Scale bar: 20 μm.

Further highlighting its potential as a biologically relevant target of Compound 2, it was noted that NAT10 had previously been linked with the SUN1 nuclear envelope protein (Y. H. Chi et al. (2007) *J. Bio. Chem.* 282, 27447), whose depletion was recently shown to rescue nuclear shape in LMNA depleted cells (C. Y. Chen et al. (2012) *Cell* 149, 565), and that the KAT activity of NAT10 has been demonstrated towards microtubule and histone substrates (Shen et al. (2009) *Exp. Cell Res.* 315, 1653). To validate the interaction between NAT10 and Compound 2, cells were pre-incubated with the clickable bioactive analogue Compound 3 or non-bioactive control Reference Compound A to allow their binding to protein targets in live cells. Next, the molecules were functionalized by addition of a biotin-containing linker, then streptavidin beads were used to retrieve bound proteins. This analysis revealed that Compound 3 but not Reference Compound A specifically retrieved NAT10 (FIG. 4F), thereby establishing that NAT10 is a target of Compound 2 in the context of living cells and indicating that this protocol selected for specific protein partners without the use of photo-crosslinking agents (S. E. Ong et al. (2009) *PNAS* 106, 4617; X. Li, T. M. Kapoor (2010) *J. Am. Chem. Soc.* 132, 2504). In parallel studies, cells were treated with Compound 3 or Reference Compound A, fixed and then Compound 3 was functionalized with a fluorophore (R. Rodriguez et al. (2009) *Nat. Chem. Biol.* 8, 301) to allow visualization of their sub-cellular distributions by high-resolution microscopy (FIG. 4G). Importantly, while little or no cellular staining was observed for inactive control Reference Compound A (FIG. 5A), there was a predominant accumulation of Compound 3 in nucleoli as well as some staining at the nuclear periphery and in the cytoplasm (FIG. 4G and FIG. 5A). Moreover, a striking overlap of labelled Compound 3 and NAT10 staining was observed, further corroborating the affinity pull-down studies. In line with these observations, siRNA-mediated depletion of NAT10 (FIG. 4G, bottom panel) led to a marked reduction of molecule Compound 3 accumulation in the nucleolus (FIG. 4G), without changes in nucleolar architecture. Collectively, these data established that NAT10 is a specific target of Compound 2 in cells.

Figure 6:
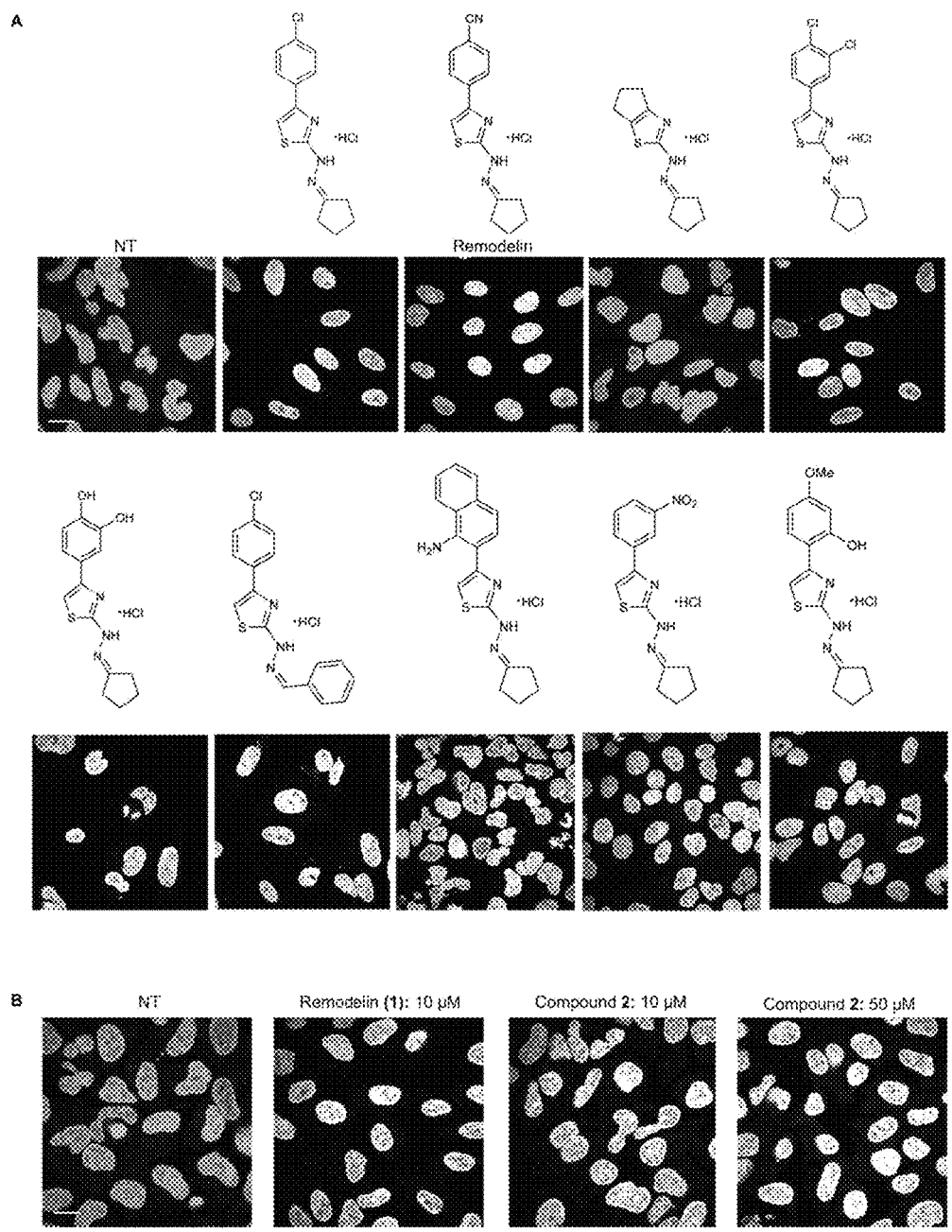
FIG. 6: A screen of Compound 2 analogues to identify structural requirements for nuclear shape rescue. A) Nuclear shape analysis by DAPI staining in siLMNA cells treated with the indicated analogues of Compound 2. B) Dose-dependent nuclear shape rescue observed by DAPI staining of siLMNA cells, showing an ~5-fold increase in the potency of Remodelin compared to Compound 2. Scale bar: 20 μm.

To assess whether the interaction between Compound 2 and NAT10 was direct, NAT10 purified from human HEK293 cells (FIG. 4H, left panel) was titrated with Compound 2 and NAT10 conformation was monitored by circular dichroism spectroscopy (FIG. 4H, right panel). In the absence of compound, the NAT10 spectra displayed a characteristic negative signal at 210 nm, reflecting the presence of α-helices. Upon addition of Compound 2, a clear increase in the absolute molar ellipticity was observed in a concentration-dependent manner, consistent with stabilization of the protein by supramolecular stapling, a process reminiscent of covalent intramolecular stapling previously described (R. E. Moellering et al. (2009) *Nature* 462, 182). These data demonstrated a direct physical interaction between Compound 2 and NAT10, and suggested that stabilization of protein folding by the molecule might inhibit NAT10 activity. During our analyses, it was found that Compound 2 was rapidly degraded upon exposure to light or air. Because of this and to try to identify more potent molecules, the ability of structural variants of Compound 2 were explored to rescue nuclear shape of LMNA depleted cells at varying doses. This revealed that while the central thiazolehydrazone core was required for nuclear shape rescue, the cyclopentane ring could be drastically altered, whereas only subtle aromatic modifications were tolerated (FIG. 6A). These studies thus identified Compound 1, containing a cyano function in the para position (FIG. 4I) as the most potent and stable analogue of the series, with a five-fold potency improvement as compared to Compound 2 (FIG. 6B). This analogue was named "Remodelin" based on its ability to remodel nuclear architecture of siLMNA cells and was used in the following experiments.

Example 3: NAT10 Inhibition Mediates Nuclear Shape Rescue

Figure 7:
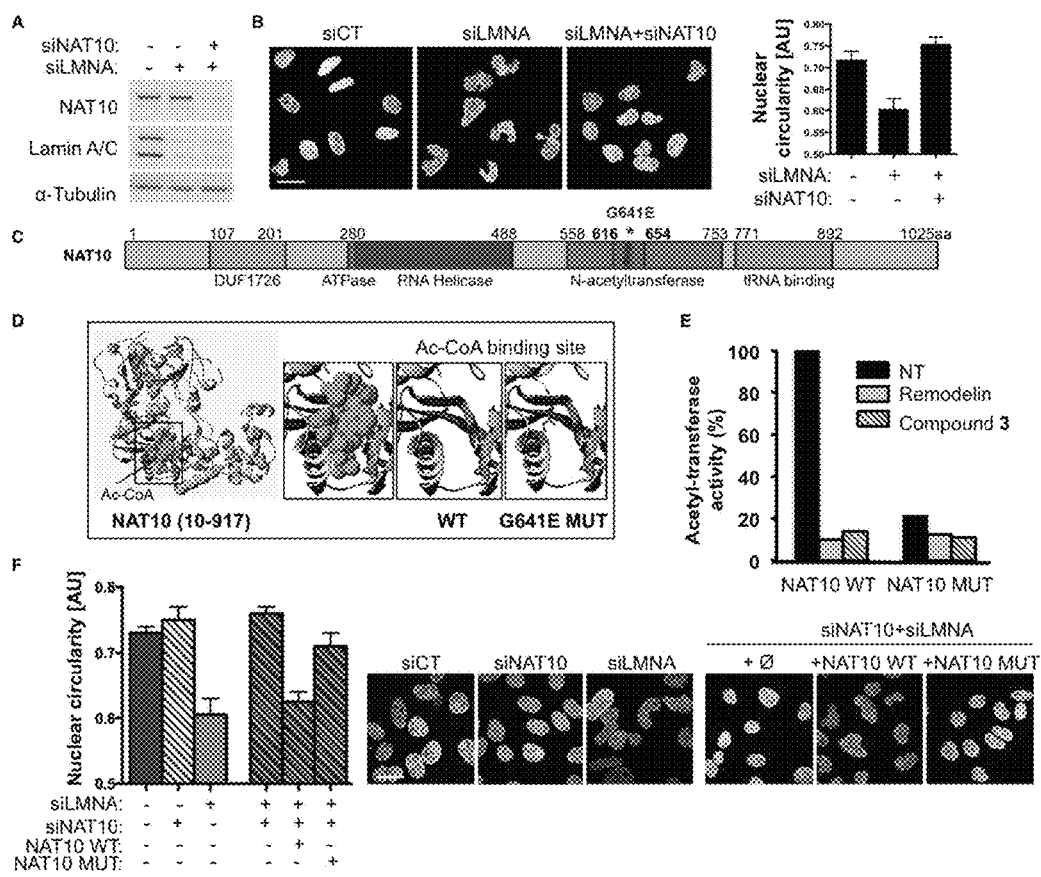
FIG. 7: Inhibiting NAT10 activity by Remodelin mediates nuclear shape rescue of LMNA depleted cells. A) Analysis of NAT10 and Lamin A/C depletion in U2OS cells. B) Nuclear shape visualised by DAPI staining (left) and quantification of nuclear circularity (right) (means of three independent experiments with n>267±s.d.). Scale bar: 20 μm. C) Representation of NAT10 with its known domains. The G641E mutation identified in D) is indicated by an asterisk. D) Modelled 3D structure of human NAT10 residues 10 to 917 showing the acetyl-CoA binding site (left) and disruption of Ac-CoA binding by NAT10 mutation (G641E, right) visualised with Swiss-Prot PDB Viewer. E) In vitro acetylation assay showing the acetyltransferase activity of NAT10 towards tubulin. F) Quantification of nuclear circularity (left) in cells stably expressing siRNA-resistant FLAG-NAT10 WT or FLAG-NAT10 G641E (FLAG-NAT10 MUT) (means of three independent experiments with n>198±s.d.) and nuclear shape visualised by DAPI staining (right). Scale bar: 20 μm.

The above studies suggested that Remodelin and related compounds might reverse nuclear shape of Lamin A/C depleted cells through NAT10 targeting. To explore this idea, NAT10 and Lamin A/C was co-depleted in human U2OS cells (FIG. 7A). Strikingly, this revealed that, comparable to the effects observed with Remodelin, NAT10 depletion completely rescued nuclear morphology defects caused by Lamin A/C depletion (FIG. 7B; similar effects were observed in RPE-1 and HeLa cells). Because molecule Compound 2, the analogue of Remodelin, was discovered as a KAT inhibitor, it was assessed whether NAT10 acetyltransferase activity was altered by Remodelin and involved in nuclear shape rescue in Lamin A/C depleted cells. To this end, a 3D-model for region 10 to 917 of human NAT10 was generated from the structure of its highly conserved bacterial homolog TmcA (Chimnaronk et al. (2009) *Embo. J.* 28, 1362), using the Phyre2 online server (L. A. Kelley, M. J. Sternberg (2009) *Nat. Protoc.* 4, 363) (FIG. 7C, D). The site of acetyl-CoA binding was then predicted by aligning this model with the original TmcA structure in complex with Ac-CoA (FIG. 7D). The conserved Gly 641 was then mutated to Glu (G641E) (FIG. 8A) which was predicted to block NAT10 acetyltransferase activity (FIG. 7D, right). Indeed, biochemical assays with wild-type (WT) and G641E mutant (MUT) NAT10 proteins expressed and purified from human HEK293 cells (FIG. 8B) showed that the G641E mutation abolished NAT10 KAT activity (FIG. 7E). Moreover, the inclusion of Remodelin or clickable bioactive Compound 3 in these reactions abolished NAT10 WT KAT activity, revealing that Remodelin is a NAT10 inhibitor.

To explore the function of NAT10 KAT activity in controlling nuclear shape, stable cell lines expressing siRNA-resistant NAT10 WT or G641E constructs were generated. Given the correct expression and subcellular localization of both proteins (FIG. 8C, D), Lamin A/C and the endogenous NAT10 protein were co-depleted and the nuclear shape morphology was studied. Strikingly, while Lamin A/C depletion impaired nuclear circularity in cells expressing NAT10 WT, this was not the case in cells expressing catalytically inactive NAT10 MUT (FIG. 7F). Collectively, these data thereby established that inactivating NAT10 KAT activity by mutation or by Remodelin action restores normal nuclear morphology of siLMNA cells.

Example 4: Remodelin Targets NAT10 to Improve Fitness of HGPS Cells

Figure 9:
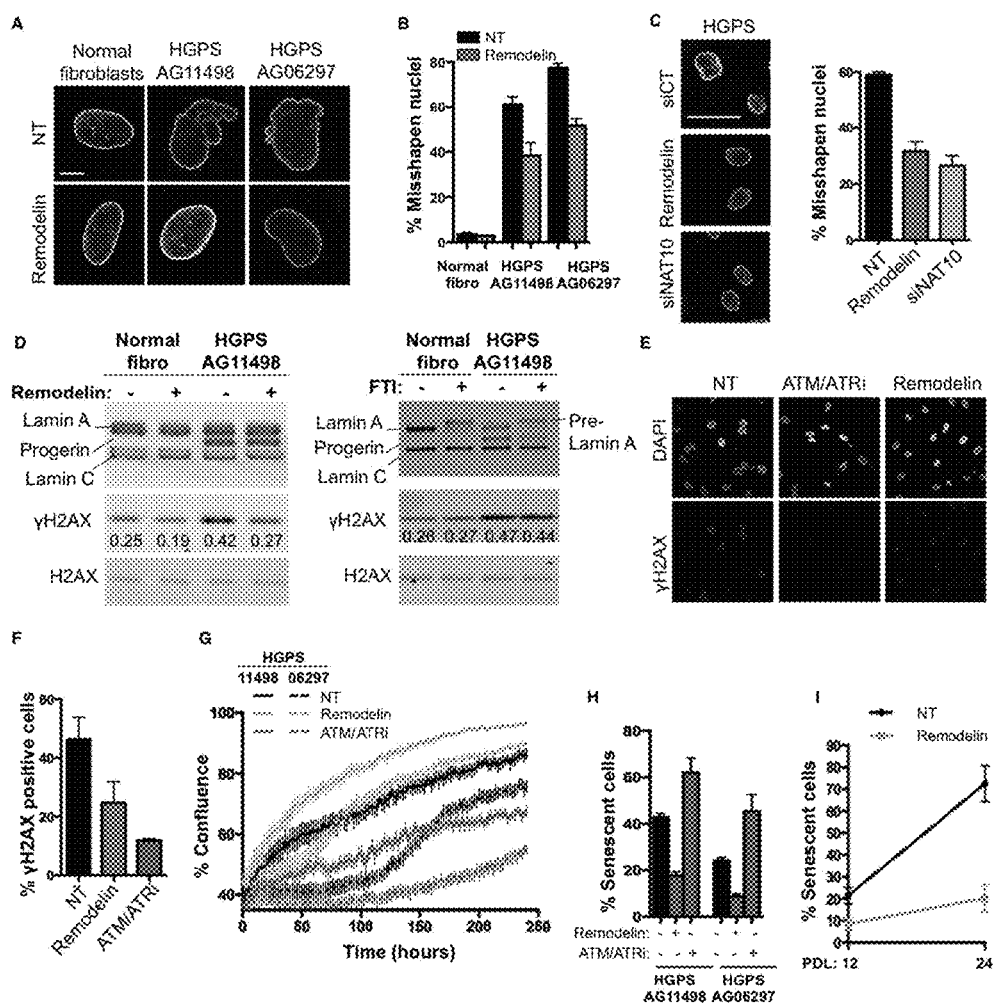
FIG. 9: Remodelin targets NAT10 to improve nuclear shape and fitness of HGPS cells. A) Representative immunofluorescence (IF) pictures of Lamin A/C in HGPS cell lines compared to matched normal fibroblasts at the same population doubling. Scale bar: 10 μm. B) Quantification of misshapen nuclei upon Remodelin treatment (means of three independent experiments with n>213±s.e.m.). C) Lamin A/C staining in HGPS AG11498 cells (left) and quantification of misshapen nuclei (right; means of three independent experiments with n>176±s.e.m.). Scale bar: 50 μm. D) Western blotting analysis of γH2AX after Remodelin or FTI treatment. E) Immunofluorescence analysis of γH2AX staining upon Remodelin or ATM/ATR inhibition (ATM/ATRi). F) Quantification of γH2AX positive cells observed by IF (means of three independent experiments with n>127±s.e.m.). G) HGPS proliferation upon Remodelin or ATM/ATR-inhibitor treatment (means of nine replicates±s.e.m). H) Quantification of senescence-associated β-galactosidase positive cells (means of three independent experiments with n>257±s.e.m.). I) Quantification of senescence-associated β-galactosidase positive cells in HGPS AG11498 after 8 days of Remodelin treatment at population doubling 12 (PDL 12) and after several weeks of Remodelin treatment and 12 cell divisions (PDL 24) (means of two independent experiments with n>298±s.d.).
Figure 10:
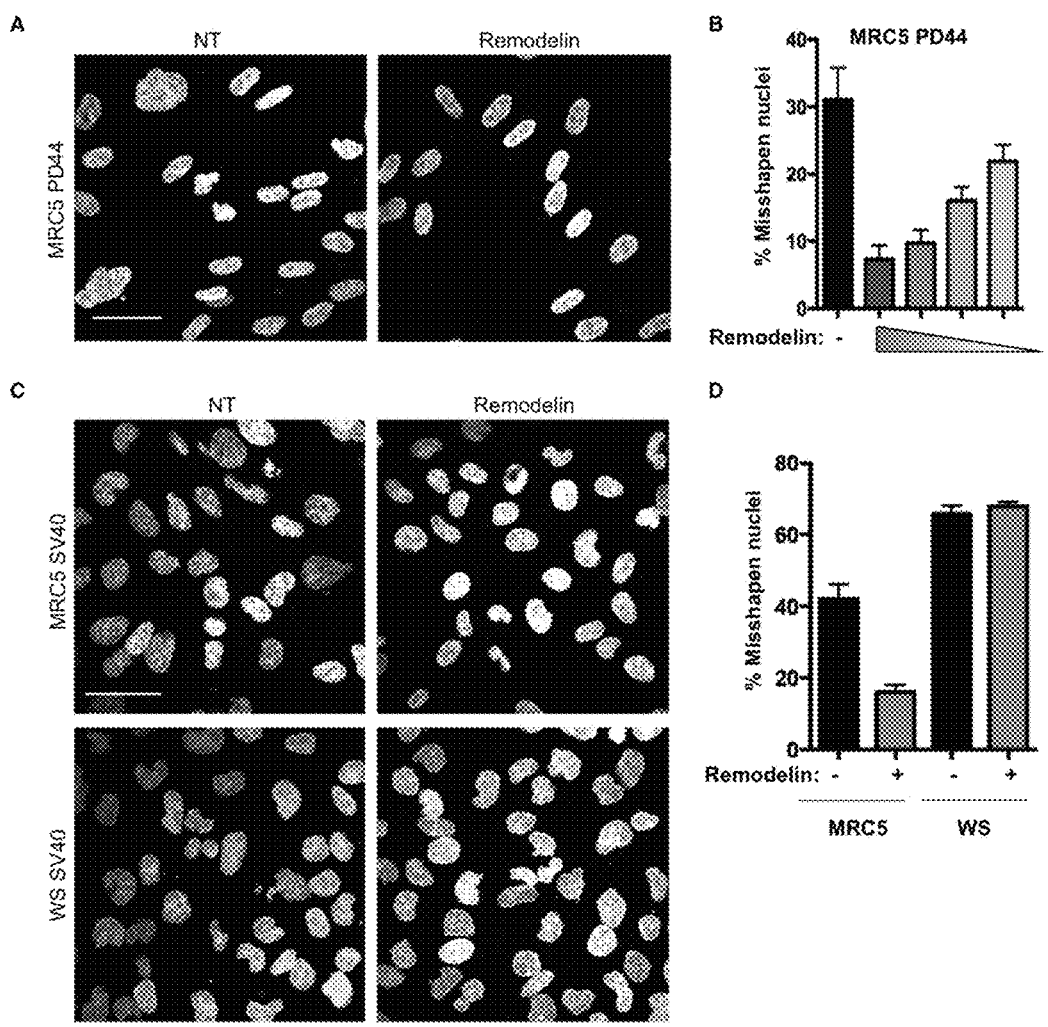
FIG. 10: Remodelin rescues nuclear shape of aged MRC5 cells but not WS cells in a dose dependent manner. A) Misshapen nuclei observed by DAPI staining in MRC5 aged cells in culture, at population doubling 44 (PD44) were rescued by Remodelin. B) Quantification of misshapen nuclei after increasing concentrations of Remodelin (mean of three independent experiments±s.e.m.). C) DAPI staining of non-laminopathic Werner Syndrome cells (WS) showing no nuclear shape improvement upon Remodelin treatment. D) Cell Profiler quantification of misshapen nuclei (mean of three independent experiments±s.d. n>273). Scale bars: 50 μm.

Having found that Remodelin rescues nuclear shape defects of Lamin A/C depleted cells, its effects on nuclear shape of LMNA mutated cells was investigated by using two primary fibroblast cell lines derived from HGPS patients (AG11498 and AG06267) carrying the heterozygous dominant point mutation LMNA c.1824C>T, p.G608G. On account of this mutation, HGPS cells express a permanently farnesylated, truncated form of Lamin A called Progerin, which accumulates with cell passage number at the nuclear rim. This leads to nuclear membrane folding and nuclear blebbing (FIG. 9A), and is at least in part responsible for the premature ageing phenotypes of HGPS patients (K. Cao et al. (2011) *J. Clin. Invest.* 121, 2833). Notably, Remodelin significantly reduced the number of HGPS cells with misshapen nuclei (FIG. 9A, B) and also had this effect on primary MRC5 fibroblasts aged in culture (FIG. 10A, B) that also become misshapen and accumulate Progerin upon extended passaging (P. Scaffidi, T. Misteli (2006) *Science* 312, 1059). By contrast, Remodelin had no detectable effect on misshapen nuclei of non-laminopathic Werner syndrome cells, indicating that nuclear shape rescue is specific to lamin-associated defects (FIG. 10C, D).

Farnesyltransferase inhibitors (FTIs) have been used in HGPS cells to prevent the toxic accumulation of farnesylated Progerin at the nuclear membrane. Indeed, non-farnesylated Progerin is relocalized away from the nuclear envelope and, as a result, nuclear blebbing is reduced (B. C. Capell et al. (2005) *PNAS* 102, 12879). To determine whether Remodelin leads to farnesyltransferase inhibition, Lamin A processing was examined by western blotting (FIG. 11A). Importantly, this demonstrated that Remodelin did not block pre-Lamin A cleavage and maturation, unlike FTI that caused accumulation of the pre-Lamin A intermediate. While this indicated that Remodelin does not inhibit farnesyltransferase activity, it was found that Remodelin and FTI did not act synergistically on nuclear shape improvement, suggesting that they impact on a common pathway (FIG. 11B, C). Significantly, unlike what was had observed for Remodelin, FTI does not improve nuclear morphology in LMNA-depleted cells, in accordance with its proposed mode of action. Furthermore, although FTI improves the nuclear shape of HGPS cells, it has the opposite effect on normal cells that do not express Progerin, (FIG. 11B, C) probably through FTI treatment leading to the accumulation and inappropriate localization of unprocessed Lamin A and B together with centrosome separation defects (V. L. Verstraeten et al. (2011) PNAS 108, 4997; M. W. Glynn, T. W. Glover (2005) Hum. Mol. Genet. 14, 2959; Y. Wang et al. (2012) Nucleus 3, 452). By contrast, Remodelin did not induce nuclear shape defects in normal human fibroblasts; and indeed, it prevented FTI-induced nuclear shape defects in such fibroblasts (FIG. 11B-D). Crucially, a comparable decrease in the number of misshapen nuclei was observed in HGPS cells upon Remodelin treatment or NAT10 depletion (FIG. 9C and FIG. 12A), leading us to conclude that—as was the case for siLMNA cells—NAT10 inhibition by Remodelin was responsible for nuclear shape improvement in HGPS cells.

Figure 12:
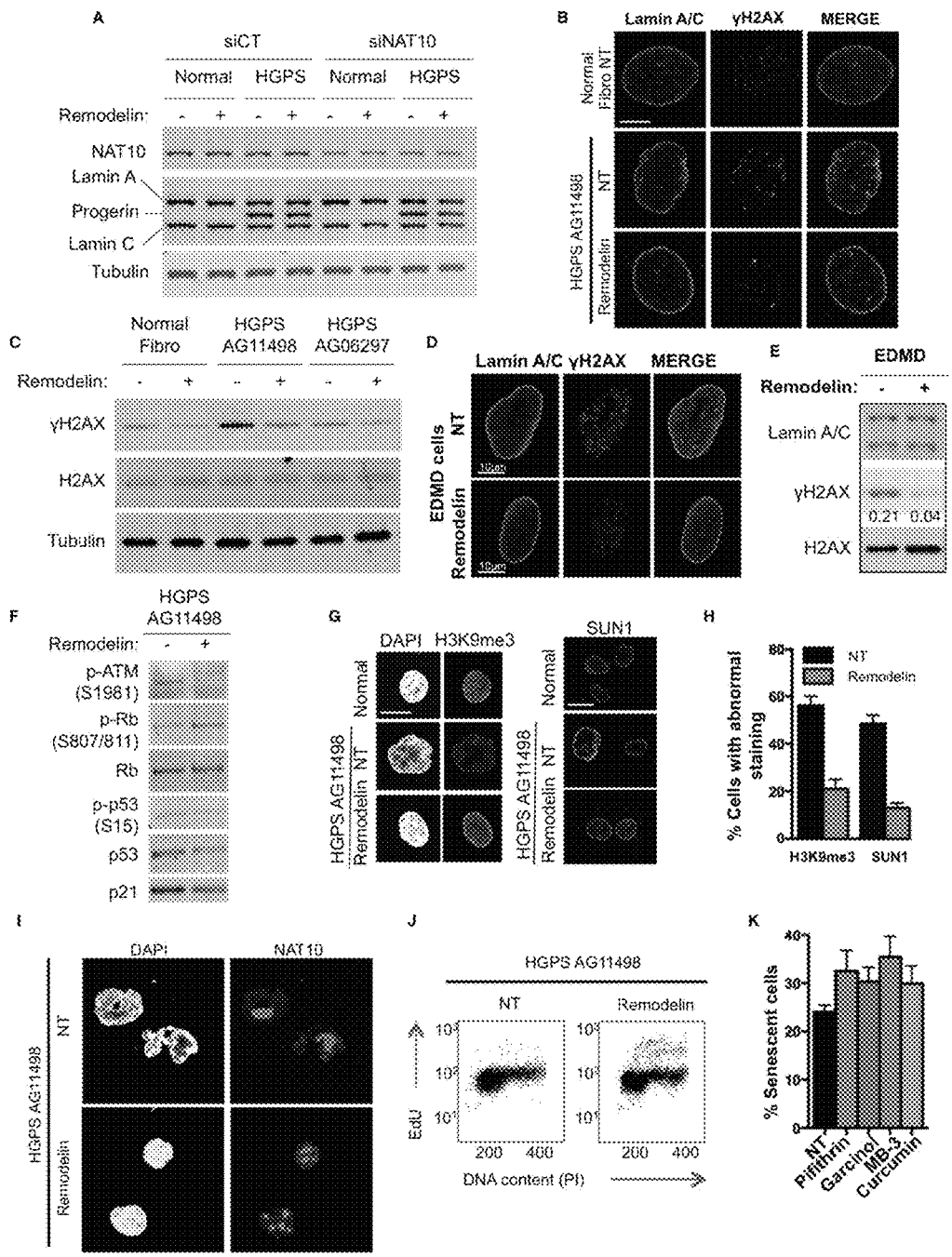
FIG. 12: Remodelin improves global cellular fitness of HGPS cells. A) NAT10 depletion in normal fibroblasts and HGPS AG11498 cells observed by western blotting, and showing that siNAT10 has no effect on Lamin A/C expression and processing. B) IF images showing nuclear shape improvement and decreased numbers of γH2AX foci in HGPS cells upon Remodelin treatment. Scale bars: 10 μm. C) Western Blotting analysis showing that Remodelin decreases γH2AX levels in both HGPS cell lines tested. D) IF images showing nuclear shape improvement and decreased intensity of γH2AX staining in Emery-Dreifuss muscular dystrophy cells (EDMD) upon Remodelin treatment. Scale bars: 10 μm. E) Western Blotting analysis showing that Remodelin decreases γH2AX levels in EDMD. F) Western blotting analysis showing the effect of Remodelin on the p53 and DNA damage signalling pathways in HGPS AG11498 cells. G) Representative IF images of H3K9me3 or SUN1 patterns quantified in H). Scale bars: 20 μm. I) IF staining showing more intense and homogenous DAPI staining, as well as reorganization of nucleolus architecture as observed by NAT10 staining upon Remodelin treatment. Scale bars: 10 μm. J) Flow cytometry analysis after 2 hours of EdU incorporation in HGPS cells upon Remodelin treatment showing enhancement of DNA replication rate. K) Quantification of senescence-associated β-galactosidase positive cells after treatment with p53 inhibitor (Pifithrin) or with the indicated KAT inhibitors, showing that none of these compounds decrease the senescence in HGPS AG11498.

While nuclear shape improvement is not always associated with overall amelioration of HGPS cell phenotypes (M. X. Ibrahim et al. (2013) Science 340, 1330), the inventors found that Remodelin improved global HGPS-cell fitness as observed by decreased steady-state levels of γH2AX and autophosphorylated ATM (markers of unrepaired DNA double-strand breaks) and decreased DNA damage signaling (FIG. 9D and FIG. 12B, C, F), improved chromatin and nucleolar organization as assessed by H3K9me3 and NAT10 staining, and decreased SUN1 accumulation at the nuclear envelope (FIG. 12G-I). That, Remodelin does not detectably affect the expression and localization of SUN1 in siLMNA cells, implies that the mechanism of nuclear shape rescue by Remodelin is distinct from that observed upon SUN1 depletion (C. Y. Chen et al. (2012) Cell 149, 565). Interestingly, cells derived from patients with Emery-Dreifuss muscular dystrophy (EDMD), also displayed decreased levels of γH2AX upon Remodelin treatment (FIG. 12D, E), suggesting that Remodelin might have broader applications to other types of laminopathies. Blocking signaling by the apical DNA-damage response kinases ATM and ATR also decreased γH2AX (FIG. 9E, F). However, unlike Remodelin—which also improved DNA replication (FIG. 12J), enhanced cell proliferation capacity (FIG. 9G) and decreased senescence (FIG. 9H, I; it should be noted from FIG. 12K that other KAT inhibitors do not decrease senescence)—inhibiting ATM and ATR decreased proliferation and induced senescence (FIG. 9G, H). As shown in FIG. 12K similar effects were observed upon p53-pathway inhibition. These data thus supported the notion that Remodelin reduces the amount of DNA damage in HGPS cells, while damage is still present but no longer signaled properly upon ATM/ATR inhibition, leading to cell growth arrest and senescence. In addition, Remodelin improved HGPS cell chromatin compaction as observed by DAPI staining intensity (FIG. 12G) and nucleolar organization, without altering NAT10 localization (FIG. 12I). Importantly, these effects of Remodelin were associated with globally increased fitness of HGPS cells, as observed by increased DNA replication (FIG. 12J), enhanced cell proliferation capacity (FIG. 9G) and decreased proportion of senescent cells (FIG. 9H). Highlighting its potential for long-term benefits, it was found that Remodelin prevented HGPS cell senescence even after several weeks of treatment (FIG. 9I).

Example 5: NAT10 Inhibition Reorganizes Microtubules to Restore Nuclear Shape

Figure 13:
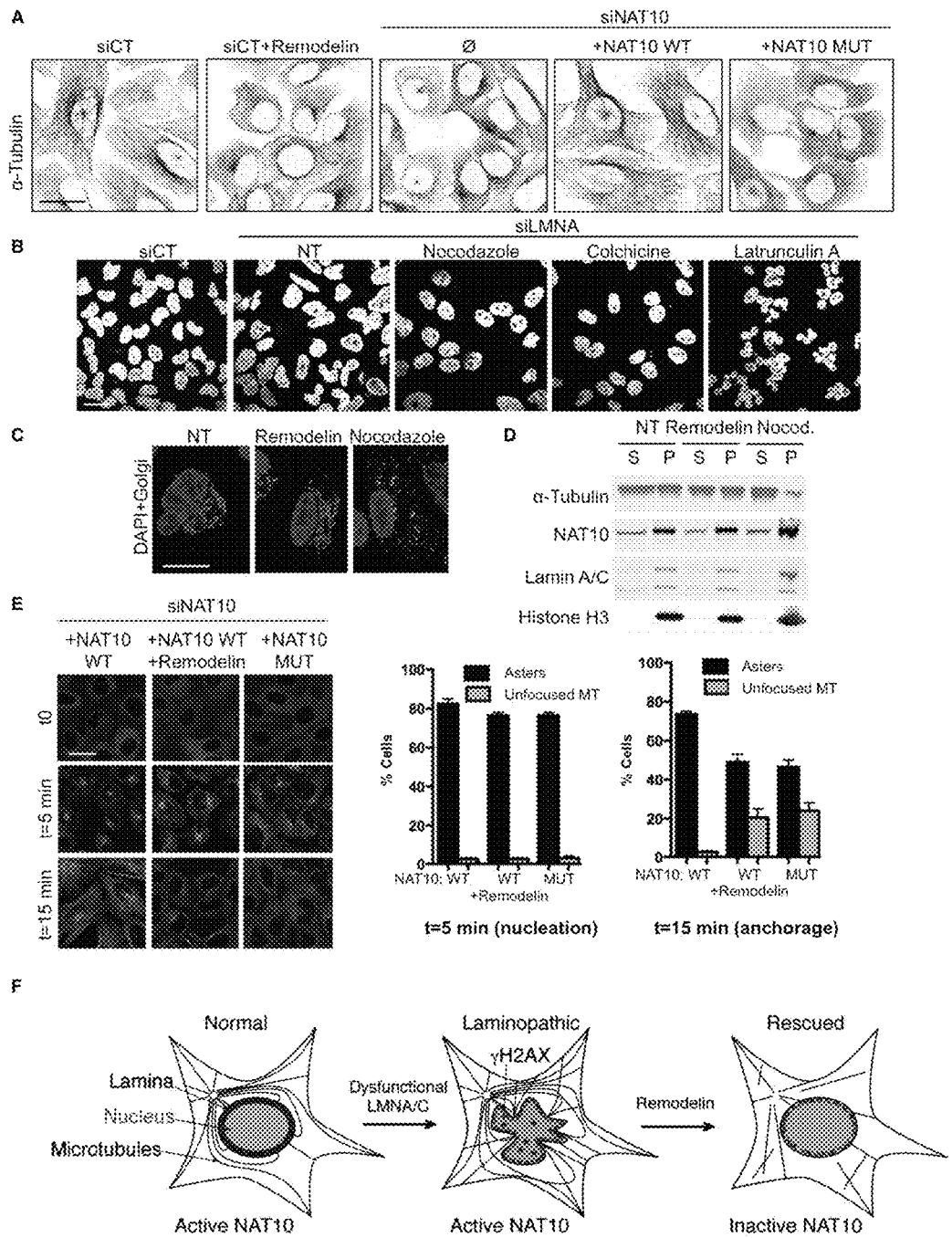
FIG. 13: Inhibiting NAT10 acetyltransferase activity modifies microtubule organisation to rescue nuclear shape defects. A) Microtubule network visualisation by inverted IF pictures of α-Tubulin. B) Nuclear shape visualisation after treating cells with microtubule or actin cytoskeleton disrupting agents. C) Visualisation of nuclear shape (DAPI) and Golgi (anti-Giantin) integrity in siLMNA cells. D) Fractionation of polymerised (P) and soluble (S) tubulin upon Remodelin or nocodazole (Nocod.) treatment. E) Microtubule regrowth assay in cells transfected with siNAT10 and expressing the indicated siRNA resistant constructs. α-tubulin IF staining (left) shows nucleation phase: t=5 minutes and microtubule anchorage (t=15 min). Right: quantification of cells with the indicated patterns (means of three independent experiments with n>103±s.e.m.). F) Laminopathic cells have enlarged, misshapen nuclei associated with disorganized chromatin structure. Upon Remodelin treatment, NAT10 acetyltransferase activity is inhibited, leading to disruption of microtubule anchorage at the centrosome and release of microtubule forces on the nuclear envelope. This release of mechanical stress on the nucleus contributes to nuclear shape rescue and global improvement of cellular fitness and chromatin organization. Scale bars: 20 μm.
Figure 14:
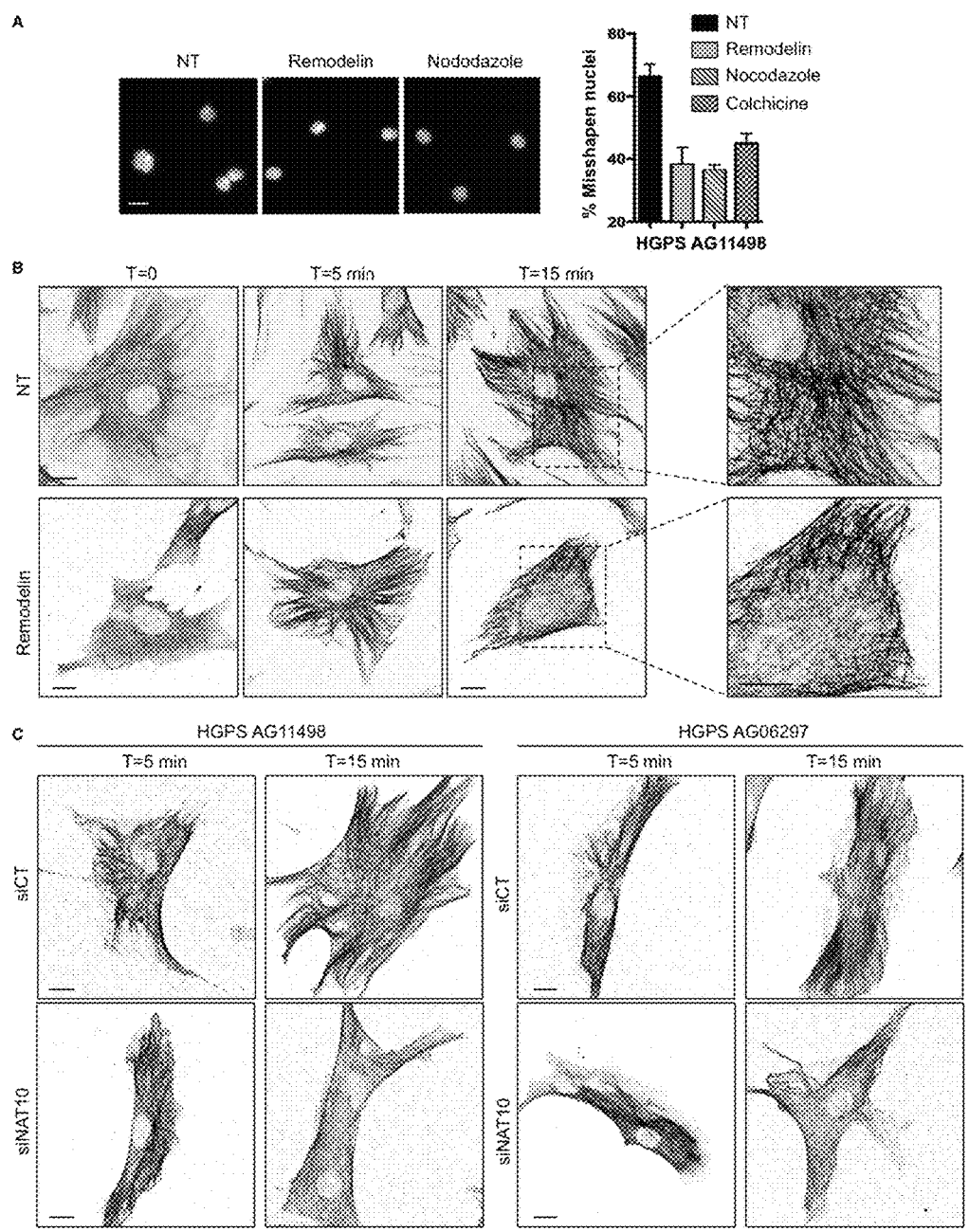
FIG. 14: Remodelin targets the microtubule network in HGPS cells to improve nuclear shape. A) Nuclear shape visualisation and quantification after treating cells with microtubule-disrupting agents. B) Microtubule regrowth assay in HGPS AG11498 cells treated with Remodelin. α-tubulin inverted IF staining shows normal microtubule depolymerisation (T=0) and nucleation phase (T=5 min) but defects in the microtubule anchorage (T=15 min) upon Remodelin treatment. C) Microtubule regrowth assay as in B) showing defects in the microtubule anchorage (T=15 min) upon NAT10 depletion (siNAT10) in the indicated HGPS cell lines and compared to cells transfected with control siRNA (siCT). Scale bars: 20 μm.

NAT10 localizes mainly in the nucleolus, a nuclear compartment whose role in maintaining global nuclear organization and nuclear shape has been demonstrated by studies showing that depleting the nucleolar proteins nucleophosmin (NPM1), fibrillarin or SENP5 leads to changes in nuclear shape (M. A. Amin et al. (2007) Biochem. Biophys. Res. Commun. 360, 320; A. Di Bacco et al. (2006) Mol. Cell Biol. 26, 4489; M. A. Amin et al. (2008) Biochem. J. 415, 345). In the case of NPM1, this has been established to occur through changes in microtubule stability (G. Wang et al. (2010) J. Biol. Chem. 285, 19060), which then impact on the nucleus via connections between the cytoskeleton and the nuclear envelope. Because of this and since tubulin is a known NAT10 substrate, the microtubule network of cells was examined by immunofluorescence and observed a striking reorganization upon Remodelin treatment. Moreover, by using the cell complementation system, it was established that equivalent microtubule reorganization was triggered by NAT10 depletion or by mutational inactivation of the NAT10 catalytic domain (FIG. 13A). In accordance with there being a functional link between microtubule reorganization and nuclear shape rescue by Remodelin treatment or NAT10 inhibition, the microtubule destabilizing drugs nocodazole and colchicine also rescued the nuclear shape defects of siLMNA cells (FIG. 13B) and HGPS cells (FIG. 14A), whereas latrunculin A, an inhibitor of actin polymerization, increased nuclear distortion (FIG. 13B). These results thereby indicated that microtubule but not actin cytoskeleton reorganization can rescue nuclear shape in the context of Lamin A/C depletion. Importantly, it was established that the effects of Remodelin were not linked to Golgi apparatus fragmentation or tubulin depolymerization, because in contrast to nocodazole or colchicine, Remodelin did not affect Golgi apparatus integrity (FIG. 13C) or tubulin assembly into polymers (FIG. 13D). These differences help explain why, unlike the situation in response to nocodazole or colchicine exposure, cells did not accumulate in mitosis upon Remodelin treatment.

Figure 11:
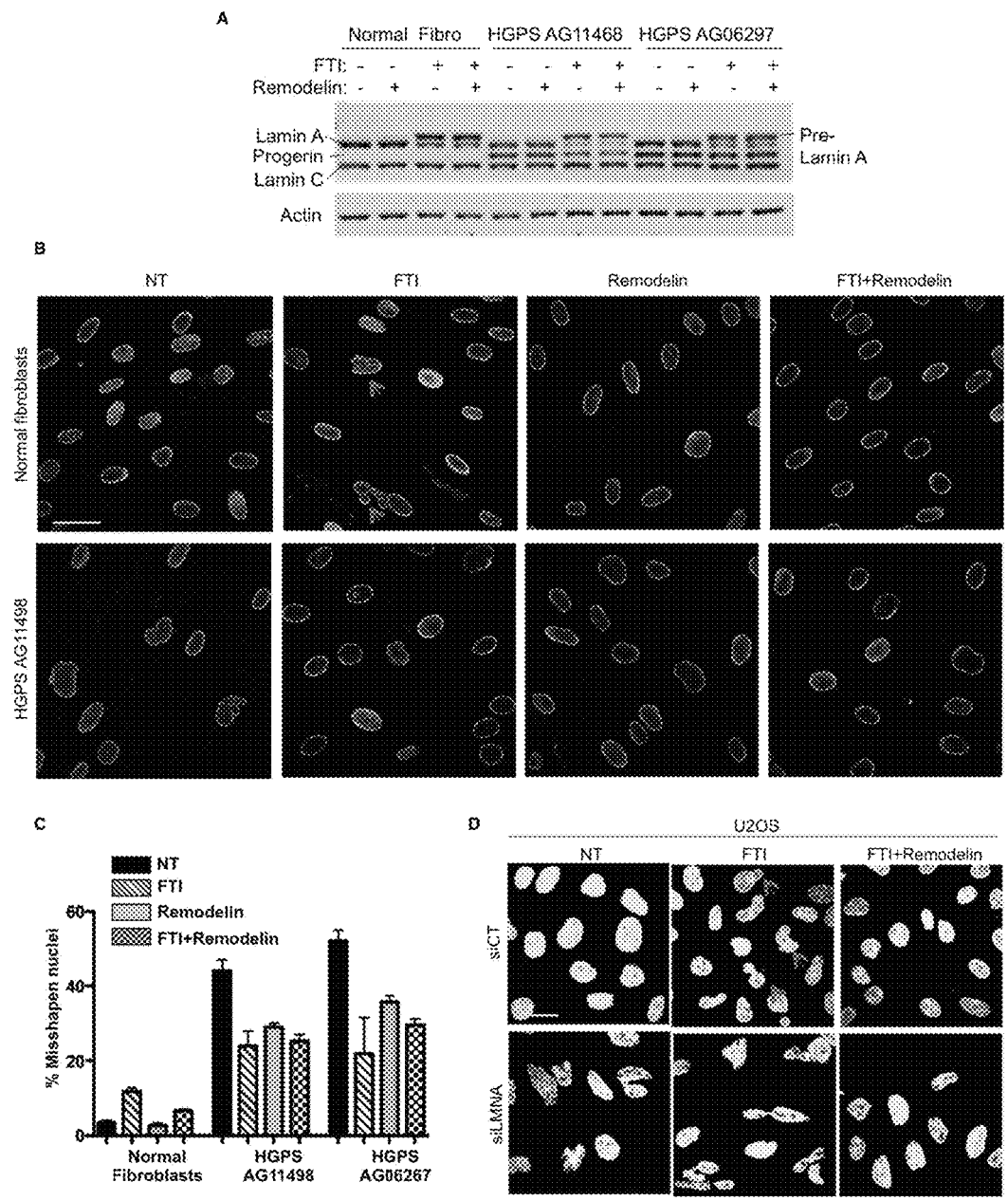
FIG. 11: Remodelin prevents FTI induced nuclear shape defects in non-progeric cells. A) Analysis of Lamin A/C processing after Remodelin or FTI treatment, showing that Remodelin is not a FTI. B) Representative pictures of Lamin A/C IF staining after the indicated treatments. Arrows indicate FTI induced misshapen nuclei in normal fibroblasts. Scale bar: 50 μm. C) Quantification of misshapen nuclei with the indicated cell lines and inhibitor treatments (means of three independent experiments±s.e.m. n>178). D) Representative pictures of DAPI staining showing effects of FTI and Remodelin on nuclear shape of U2OS cells. Scale bars: 20 μm.

To gain insight into how NAT10 modifies microtubule organization, microtubule dynamics were analysed by performing regrowth assays after cold-induced depolymerization and release into warm medium. While initial microtubule regrowth (the nucleation phase) appeared normal after NAT10 inhibition in siLMNA cells (FIG. 13E, t=5 minutes) and HGPS cells (FIG. 14B), anchorage of microtubules to centrosomes was clearly affected by Remodelin treatment in both siLMNA cells (FIG. 13E) and HGPS cells (FIG. 14B) or by the NAT10 G641E mutation (FIG. 13E, t=15 minutes), indicating that NAT10 KAT activity promotes microtubule anchorage. In accord with this, nuclear shape rescue was observed in siLMNA cells upon depletion of the PCM-1 protein that is involved in microtubule anchorage (A. Dammermann, A. Merdes (2002) J. Cell Biol. 159, 255). Since microtubules exert an external force on the nucleus that contributes to nuclear envelope deformation (M. C. King et al. (2008) Cell 134, 427), the results therefore support a model in which inhibiting NAT10 KAT activity in laminopathic cells reduces microtubule anchorage, thereby releasing an external force on the nuclear envelope and contributing to nuclear shape rescue and global enhancement of cellular fitness (FIG. 13F). This model is in accordance with previous work suggesting that releasing microtubule forces on the nucleus by modifying substrate stiffness normalizes the nuclear shape of laminopathic cells (C. Tamiello et al. (2013) *Nucleus* 4, 61) and helps explain why Remodelin, like other microtubule reorganizing agents (N. Suzuki et al. (1998) *PNAS* 95, 10499), corrects FTI-induced nuclear shape defects in non progeric cells (FIG. 11).

Example 6: Analysis of Structure Requirements for Nuclear Shape Rescue

Figure 18:
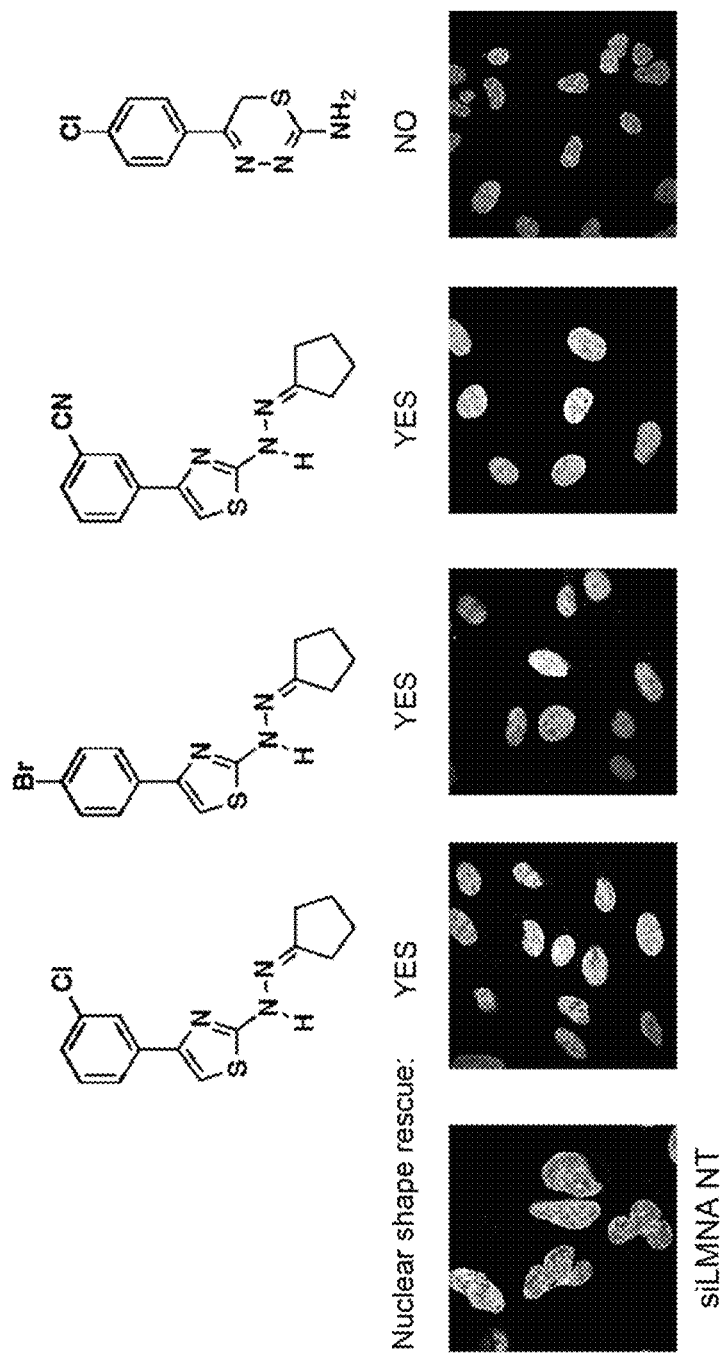
FIGS. 18 and 19: Analysis of structure requirements for nuclear shape rescue. The results of this analysis are described in Example 6.
Figure 19:
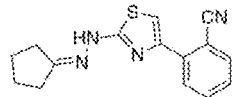

Lamin A/C was depleted by siRNA in U2OS cells (siLMNA) to induce misshapen nuclei. Cells were then treated for 16 h with various analogues of Compound 2 and nuclear shape rescue was analysed by DAPI staining. The results are shown in FIG. 18 and FIG. 19 which display the structures of the tested molecules and their ability to rescue nuclear shape.

Figure 15:
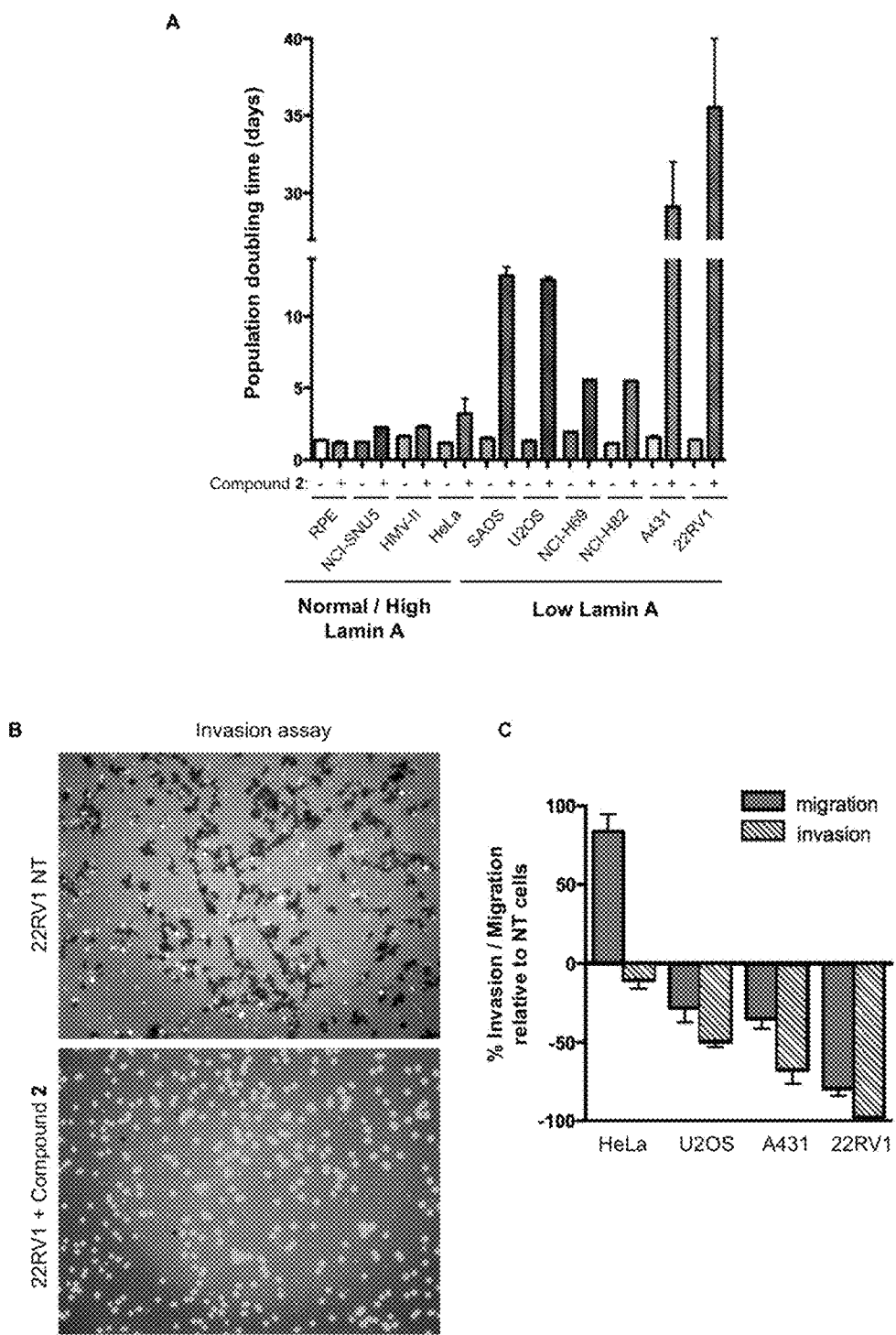
FIG. 15: Compound 2 inhibits the proliferation, migration and invasion of cancer cells with low Lamin A/C expression. A) Population doubling time of the indicated cancer cell lines treated or not with 50 μM of compound 2 for 1 week, showing that cells expressing low levels of Lamin A are more sensitive to the molecule. B) Representative pictures of matrigel invasion assay of prostate 22RV1 cancer cells, showing no invasion upon treatment with 50 μM of compound 2. C) Quantification of transwell migration assays and matrigel invasion assays from the indicated low expressing cancer cell lines after treatment with 50 μM of compound 2.
Figure 16:
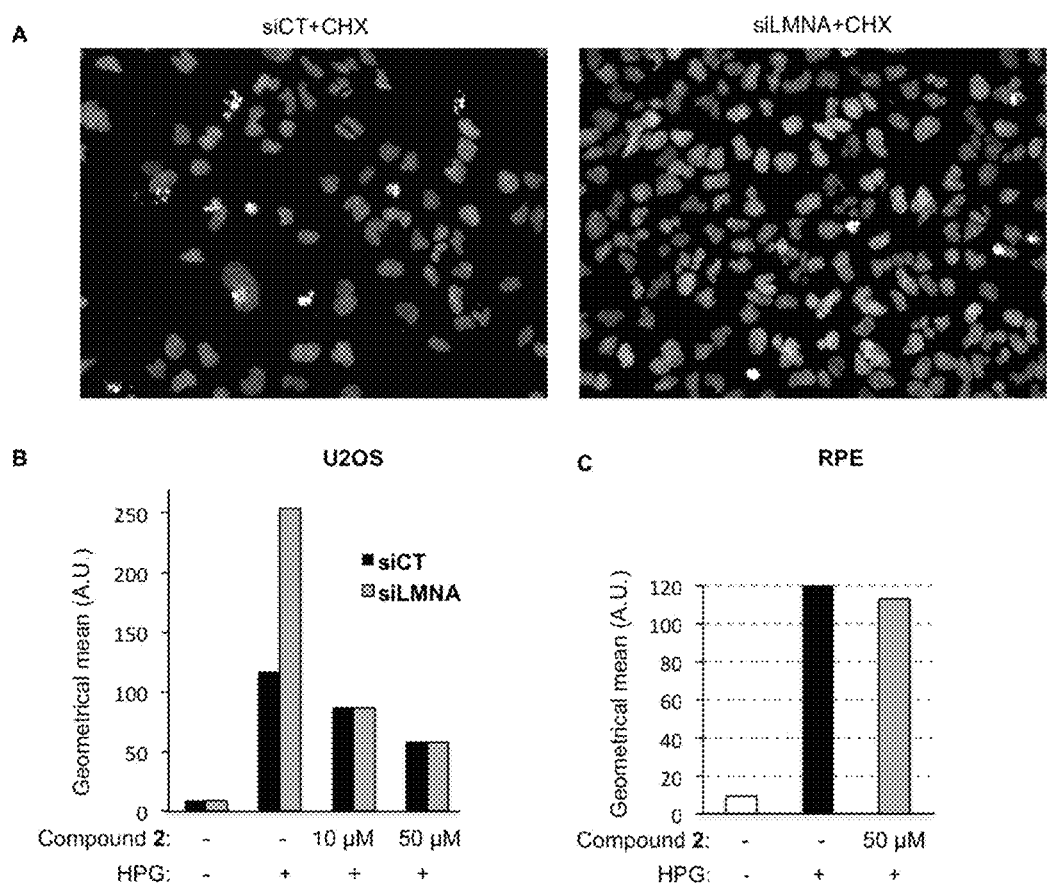
FIG. 16: Compound 2 decreases protein translation of Lamin A/C depleted cells. A) U2OS cells transfected with siRNA control (siCT) or siRNA Lamin A/C (siLMNA) were plated at the same density, treated with cycloheximide (CHX) for 24 h to inhibit protein synthesis and stained with DAPI. Representative pictures of DAPI staining show that siLMNA cells are more resistant to CHX. B) Protein synthesis was measured by quantifying the incorporation of HPG, a clickable analogue of methionine. FACS analysis shows quantification of HPG intensity in low Lamin A expressing U2OS cells (B) or in normal RPE cells (C) after increasing doses of compound 2.
Figure 17:
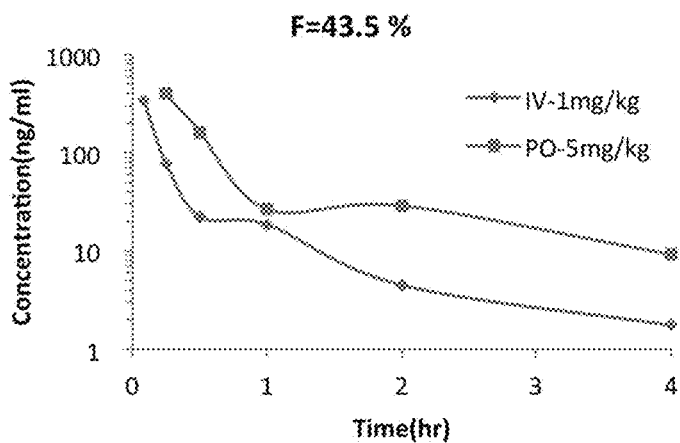
FIG. 17: Pharmacokinetics assay of Remodelin in mice. A) The pharmacokinetics of Remodelin was evaluated in ICR mice following IV at 1 mg/kg and PO at 5 mg/kg dose level. Following IV 1 mg/kg administration, the half-life (T½) was 0.915 h, and clearance was 139 mL/min/kg. Following PO 5 mg/kg administration, the half-life (T½) was 1.81 h, the maximum plasma concentration (Cmax, 409 ng/mL) was achieved at 0.25 h (Tmax) and Oral exposure was 259 ng/h/mL (AUCO-∞), bioavailability is 43.5%. B) Details of the results obtained in the curves shown in A).
Figure 20:
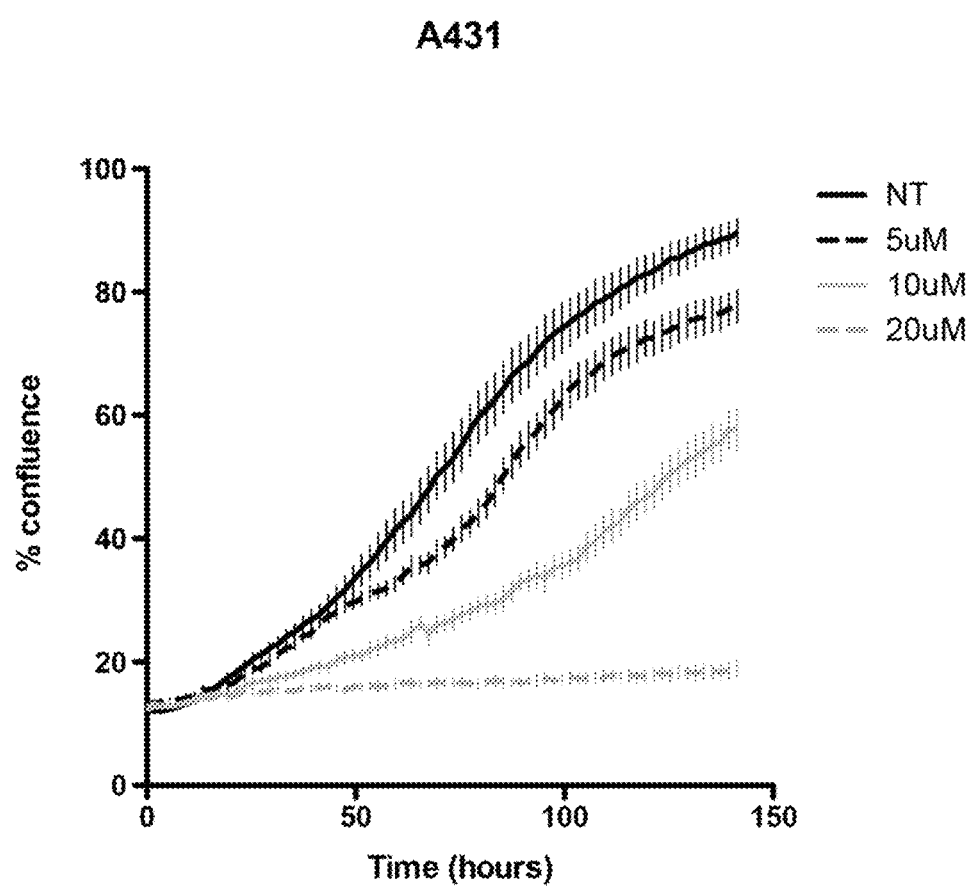
FIG. 20: Compound 2 inhibits the growth of A431 melanoma cell line in a dose-dependent manner. The results of this analysis are described in Example 7.

Example 7: Compound 2 Inhibits the Growth of A431 Melanoma Cell Line in a Dose-Dependent Manner A431 cells expressing a low level of Lamin A protein (see FIG. 2) were plated at low density and treated with the indicated concentration of Compound 2. Cell growth was monitored automatically over time using an IncuCyte ZOOM®. The results are shown in FIG. 20. The proliferation assay shows that A431 cell growth is inhibited in a dose-dependent manner. A concentration of 10 µM Remodelin is enough to reduce the proliferation of these cells by about 50% whereas cells expressing high levels of lamin A/C were not affected by up to 50 µM Remodelin (see FIG. 15).

Figure 21:
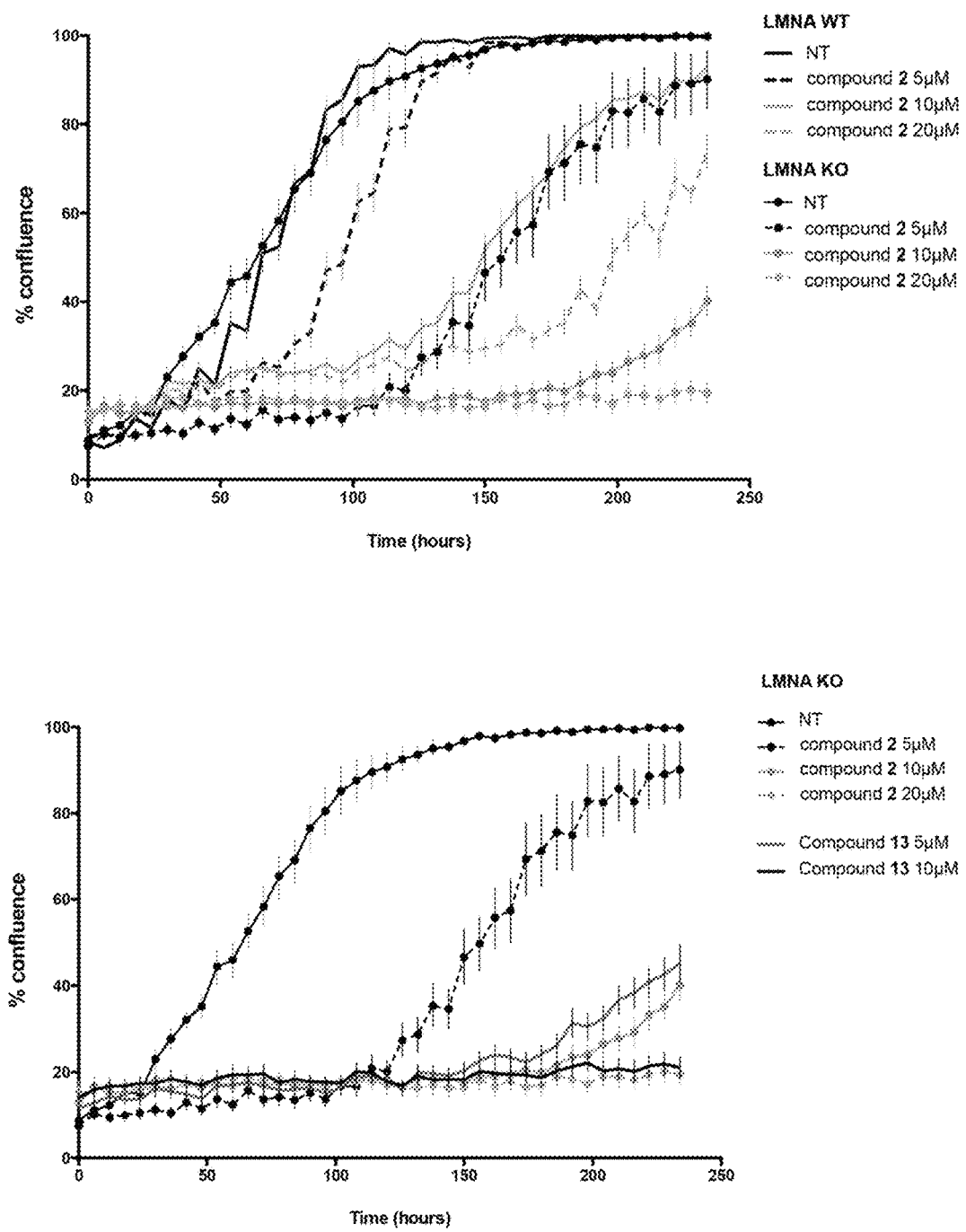
FIG. 21: Lamin A/C knock-out U2OS cells are more sensitive to Compound 2 and analogues than wild type cells. The results of this analysis are described in Example 8.

Example 8: Lamin A/C Knock-Out U2OS Cells are More Sensitive to Compound 2 and Analogues than Wild Type Cells LMNA knock out (KO) U2OS cell line was engineered using CripR/Cas9 technology. The sensitivity of LMNA KO cells to Compound 2 was compared to cells expressing wild type LMNA (LMNA WT). Cell growth was monitored automatically over time using an IncuCyte ZOOM®. The results are shown in FIG. 21 which has been split into two graphs for easier reading of the curves. The upper panel shows the specificity of Compound 2 towards inhibiting cell growth of LMNA KO cells. The lower panel shows an increased potency of Compound 13, compared to Compound 2 on LMNA KO cell growth inhibition.

Figure 22:
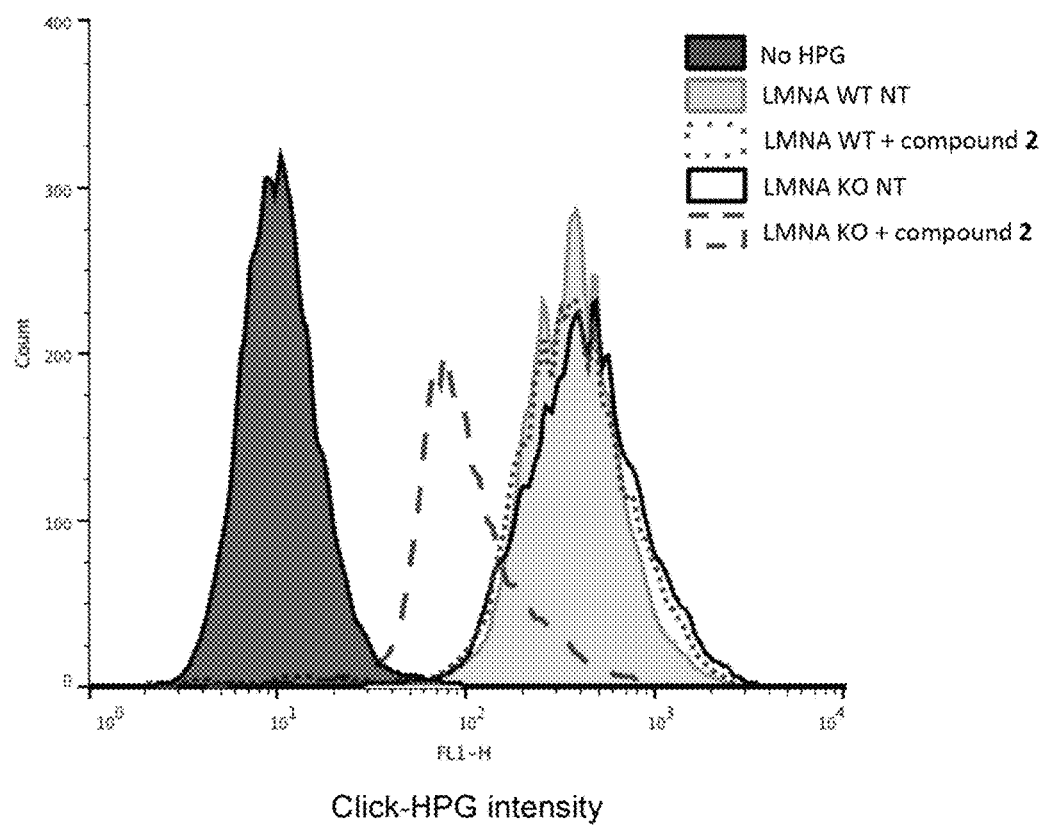
FIG. 22: Compound 2 inhibits global protein translation specifically in LMNA KO cells. The results of this analysis are described in Example 9.

Example 9: Compound 2 Inhibits Global Protein Translation Specifically in LMNA KO Cells U2OS cells expressing wild type or KO LMNA were treated with Compound 2 for 24 h and incubated for 1 h with the clickable methionine analogue HPG to measure global protein translation. HPG was then clicked with an Alexa fluor 488 and global fluorescence intensity was quantified by FACS on 10 000 cells. The graphs in FIG. 22 show a strong reduction of global protein translation upon Compound 2 addition in LMNA KO cells but not in LMNA WT cells, which might account for the difference of cell growth inhibition observed in the previous figure.

Example 10: Depletion of NAT10 Leads to Similar Inhibition of Proliferation, Migration and Invasion than Treatment with Compound 2

Figure 23:
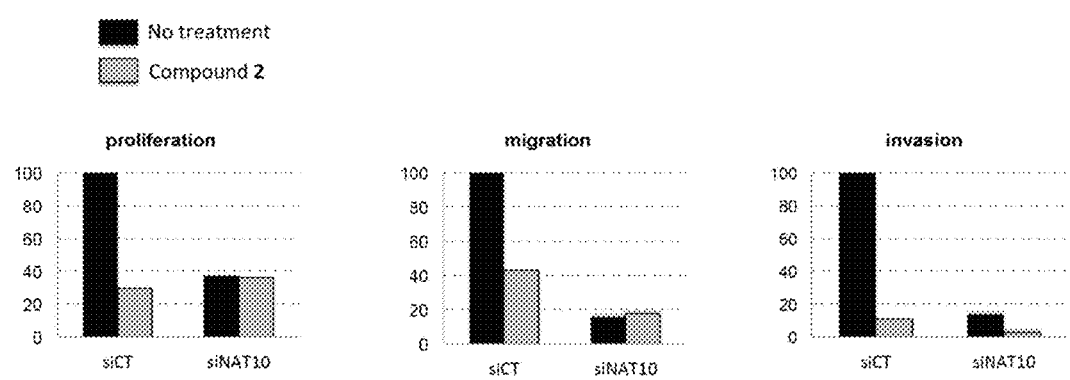
FIG. 23: Depletion of NAT10 leads to similar inhibition of proliferation, migration and invasion than treatment with Compound 2. The results of this analysis are described in Example 10.

NAT10 was depleted by siRNA in U2OS cells (siNAT10) and cells were then treated with Compound 2 for 16 h before being seeded on matrigel for migration/invasion assays. In parallel, cells from the same plates were seeded separately to assess cell proliferation. The results are shown in FIG. 23 and are presented as percentage of cell number compared to untreated control cells (siCT). The graphs show that inhibiting NAT10 with Compound 2 or depleting it with siRNA leads to similar reduction of cell proliferation, migration and invasion.

Example 11: Assessment of Compound 2 In Vivo Toxicity and In Vitro Specificity

Figure 24:
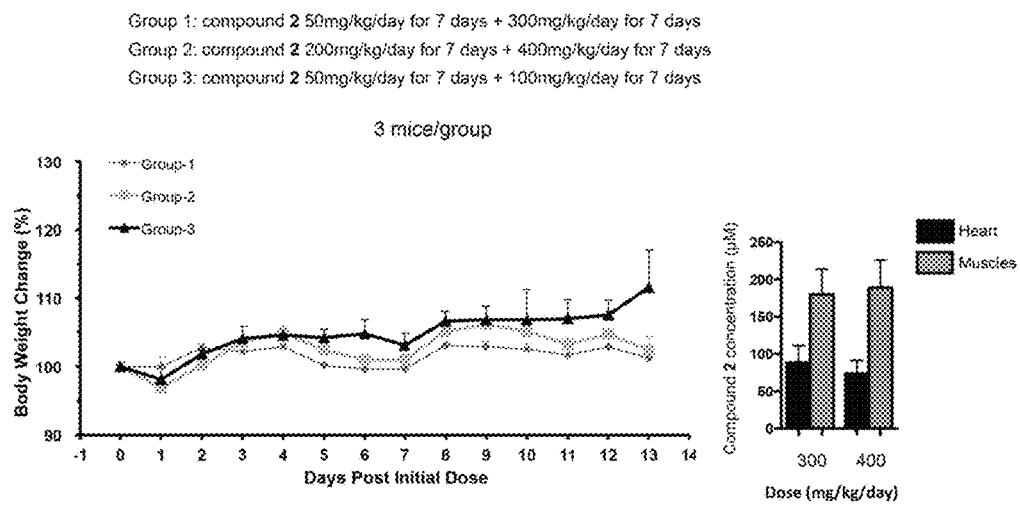
FIG. 24: Assessment of Compound 2 in vivo toxicity and in vitro specificity. The results of this analysis are described in Example 11.
Figure 24:
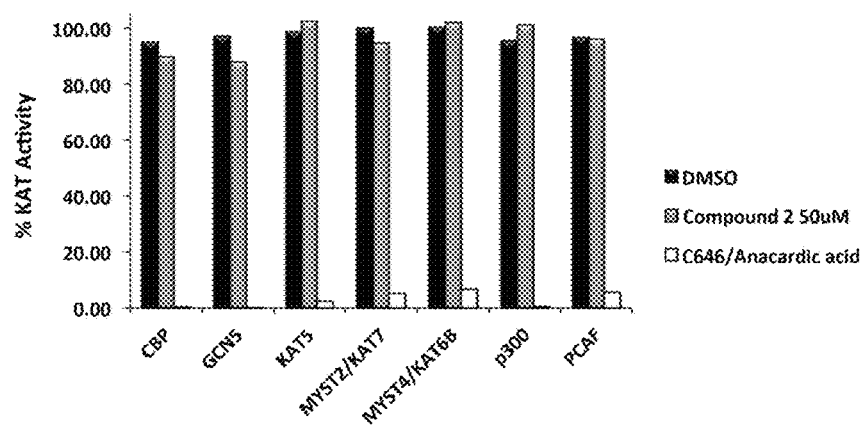

Compound 2 was administered to mice orally with the indicated daily dose, for 14 days and the results are shown in FIG. 24. Left panel of FIG. 24: body weight change shows that the compound is well tolerated orally, up to high doses of 400 mg/kg/day, without significant decrease of body weight. Right panel of FIG. 24: measurement of Compound 2 concentration in heart and muscles of mice treated with the indicated dose, at the end of the 14 days treatment. The graph shows a very high concentration of the compound in both heart and muscles, suggesting compound accumulation over time.

Lower panel of FIG. 24 shows that Compound 2 does not inhibit the activity of the main lysine acetyltranferase proteins (KAT) in vitro towards their histone substrates, suggesting high specificity towards NAT10 inhibition, and thus potentially low toxicity in vivo.

Figure 25:
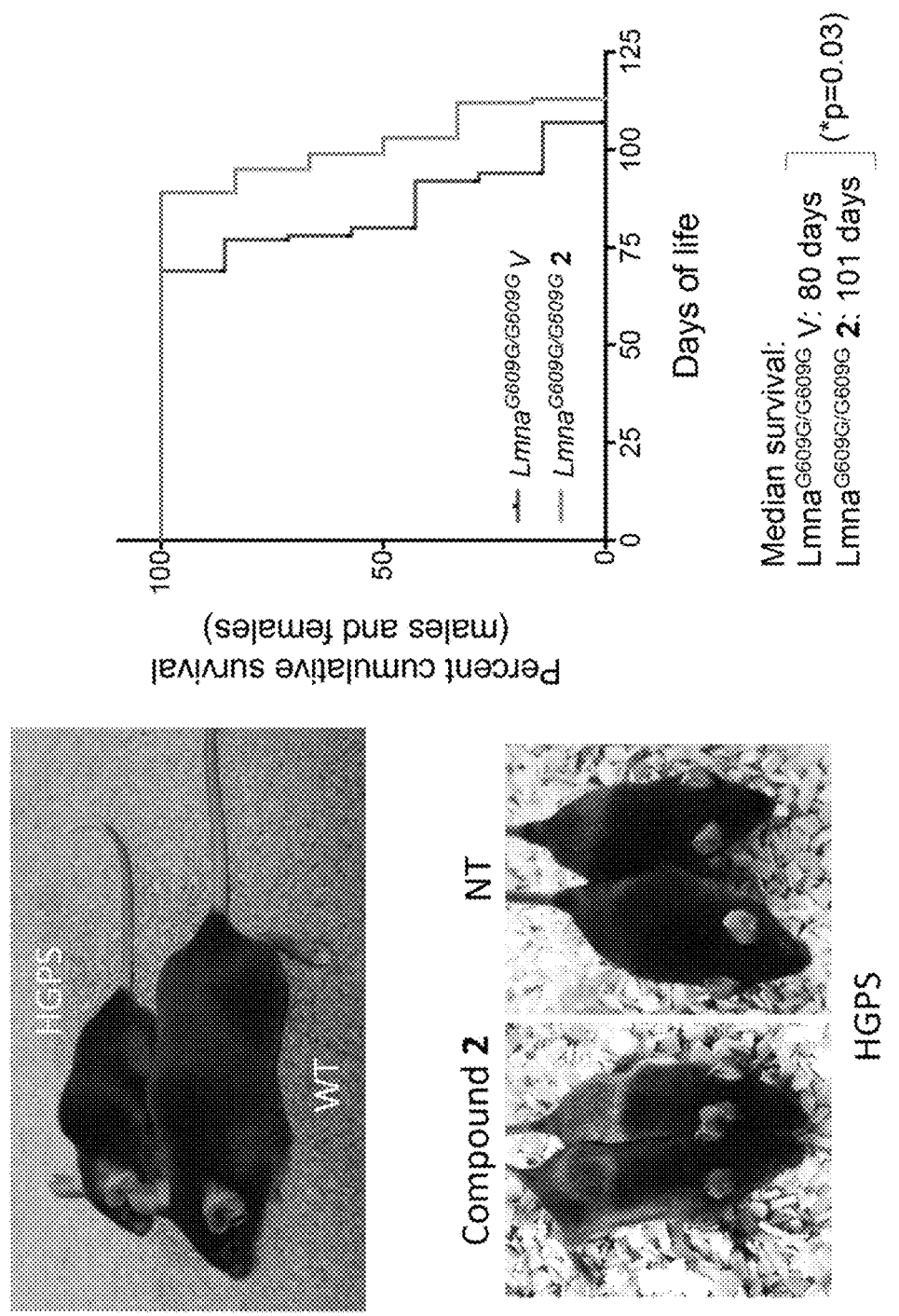
FIG. 25: Effect of Compound 2 treatment on a mouse model of Hutchinson Gilford progeria syndrome. The results of this analysis are described in Example 12.

Example 12: Effect of Compound 2 Treatment on a Mouse Model of Hutchinson Gilford Progeria Syndrome Left panel of FIG. 25: An HGPS mouse model engineered to carry the G609G mutation on both alleles displayed smaller size and back curvature compared to wild type mice. Middle panel of FIG. 25: HGPS mice were treated with a daily oral dose of 100 mg/kg/day of Compound 2 from 3 weeks of age and until culled due to >20% body weight loss. After several days of treatment with Compound 2, mice displayed hair graying that could reflect target engagement. Right panel of FIG. 25: Global survival of HGPS mice (Lmna$^{G609G/G609G}$) treated with vector only (Lmna$^{G609G/G609G}$ V) or with Compound 2 (Lmna$^{G609G/G609G}$2) showing a significant increase of the median survival of mice upon Compound 2 treatment (+25%). Number of mice/group n=10.

Example 13: Molecular Effects of Compound 2 In Vivo

Figure 26:
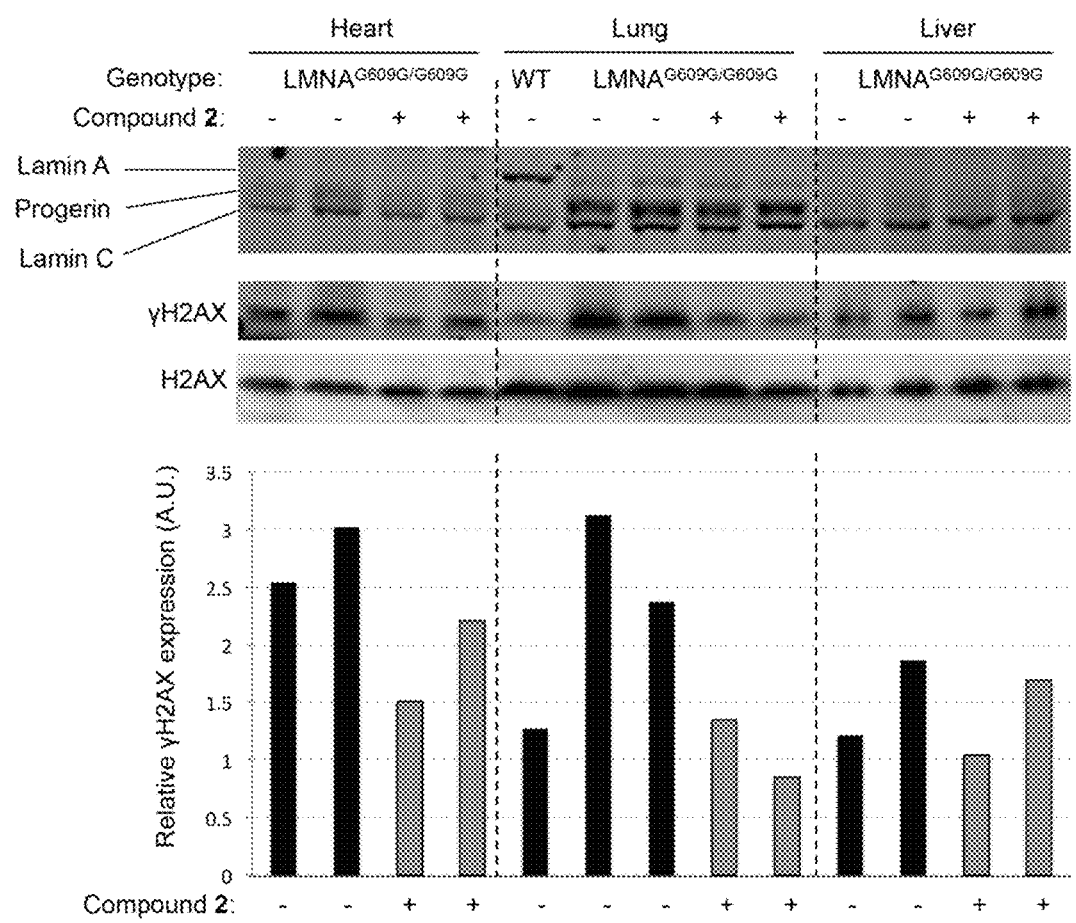
FIG. 26: Molecular effects of Compound 2 in vivo. The results of this analysis are described in Example 13.

Tissues from wild type mice or Lmna$^{G609G/G609G}$ mice treated with Compound 2 were harvested and proteins were extracted and loaded on a western blot which is shown in FIG. 26. Lmna$^{G609G/G609G}$ mice indeed show progerin expression (readily detectable mainly in the Lung tissues), confirming their genotype. DNA damage was assessed by the DNA double strand break marker γH2AX that was quantified using a Licor Odyssey Imaging system. The relative amount of γH2AX compared to total H2AX is represented below the western blot and shows a clear decrease of DNA damage in tissues from Lmna$^{G609G/G609G}$ mice that were treated with Compound 2, compared to the untreated mice, in both heart and lung. No effect was observed in liver extracts, suggesting that Compound 2 might not accumulate in the liver.

Figure 27:
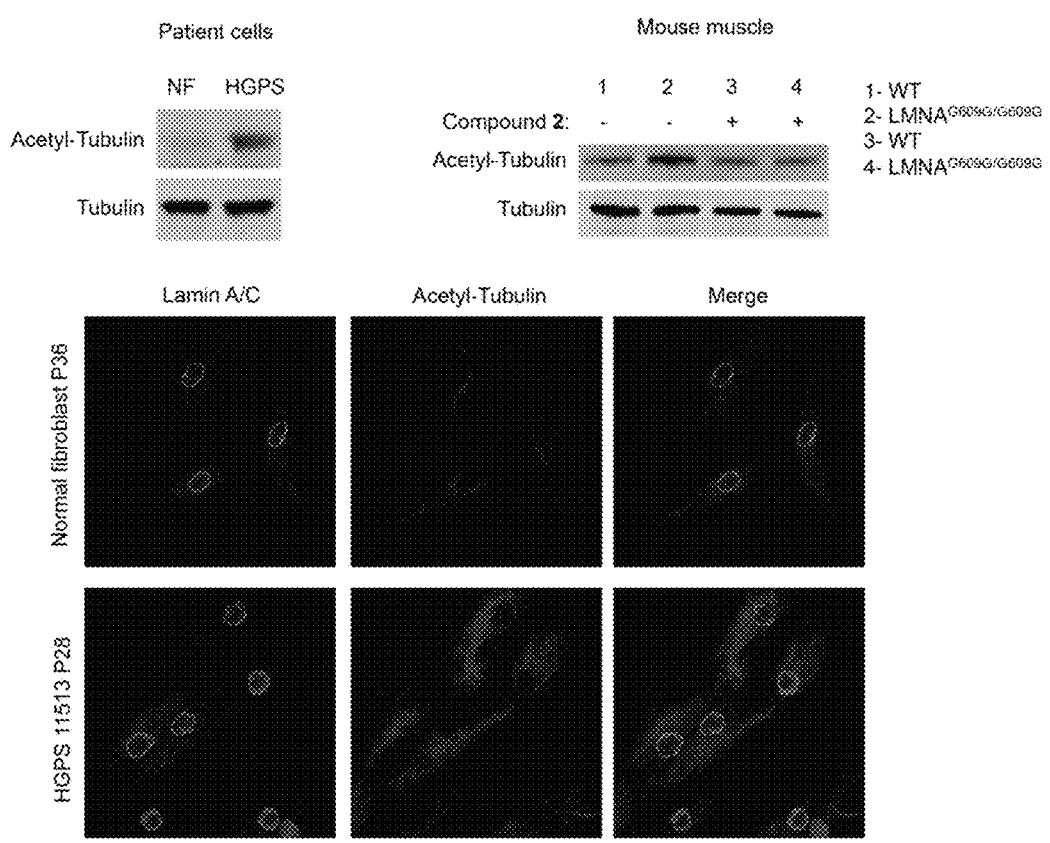
FIG. 27: Assessment of acetyl tubulin as a potential biomarker for NAT10 inhibition. The results of this analysis are described in Example 14.

Example 14: Assessment of Acetyl Tubulin as a Potential Biomarker for NAT10 Inhibition As Tubulin is a direct substrate of NAT10, Tubulin acetylation levels in cells derived from HGPS patients (left and bottom panel of FIG. 27) were assessed as well as in Lmna$^{G609G/G609G}$ mice (right panel of FIG. 27). Tubulin acetylation appears higher in both patient cells and Lmna$^{G609G/G609G}$ mice, suggesting that NAT10 might be hyper-activated. Treated of Lmna$^{G609G/G609G}$ mice with Compound 2 led to a decrease of tubulin acetylation levels (right panel of FIG. 27), suggesting that this acetylation mark could be a good biomarker for NAT10 inhibition in vivo.

Figure 28:
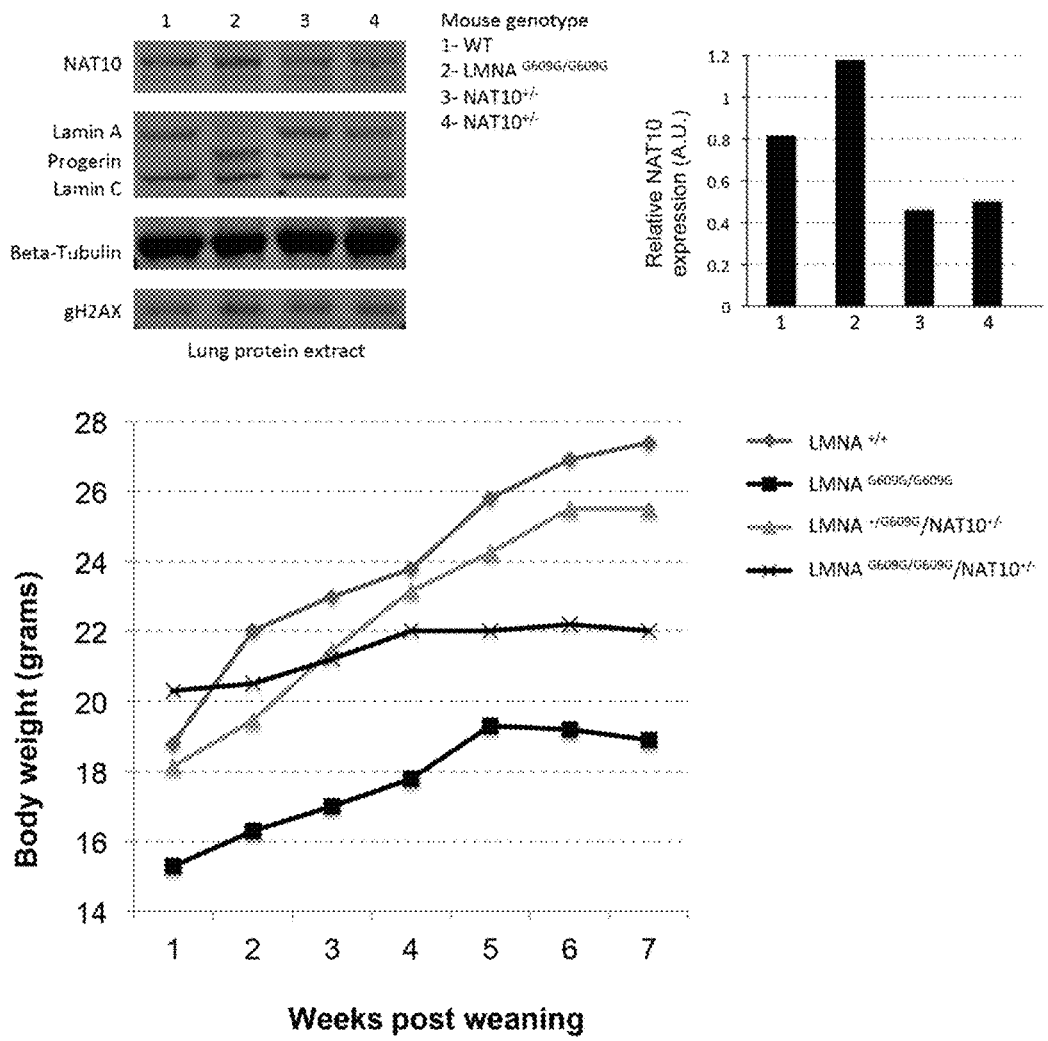
FIG. 28: Engineering a $Lmna^{G609G/G609G}/NAT10^{+/-}$ mouse for genetic validation. The results of this analysis are described in Example 15.

Example 15: Engineering a Lmna$^{G609G/G609G}$/NAT10$^{+/-}$ Mouse for Genetic Validation Top left panel of FIG. 28: Assessment of NAT10 expression level in Lung protein extracts from shows about 50% reduction of NAT10 expression in NAT10$^{+/-}$ mice, compared to WT or Lmna$^{G609G/G609G}$ (top right panel of FIG. 28). Lower panel of FIG. 28: Body weight of the indicated mouse genotypes, showing a strong increase of body weight in Lmna$^{G609G/G609G}$/NAT10$^{+/-}$ mouse, compared to Lmna$^{G609G/G609G}$ mouse and suggesting that 50% reduction of NAT10 is sufficient to rescue, at least partially, the phenotype of Lmna$^{G609G/G609G}$ HGPS mice.

Figure 29:
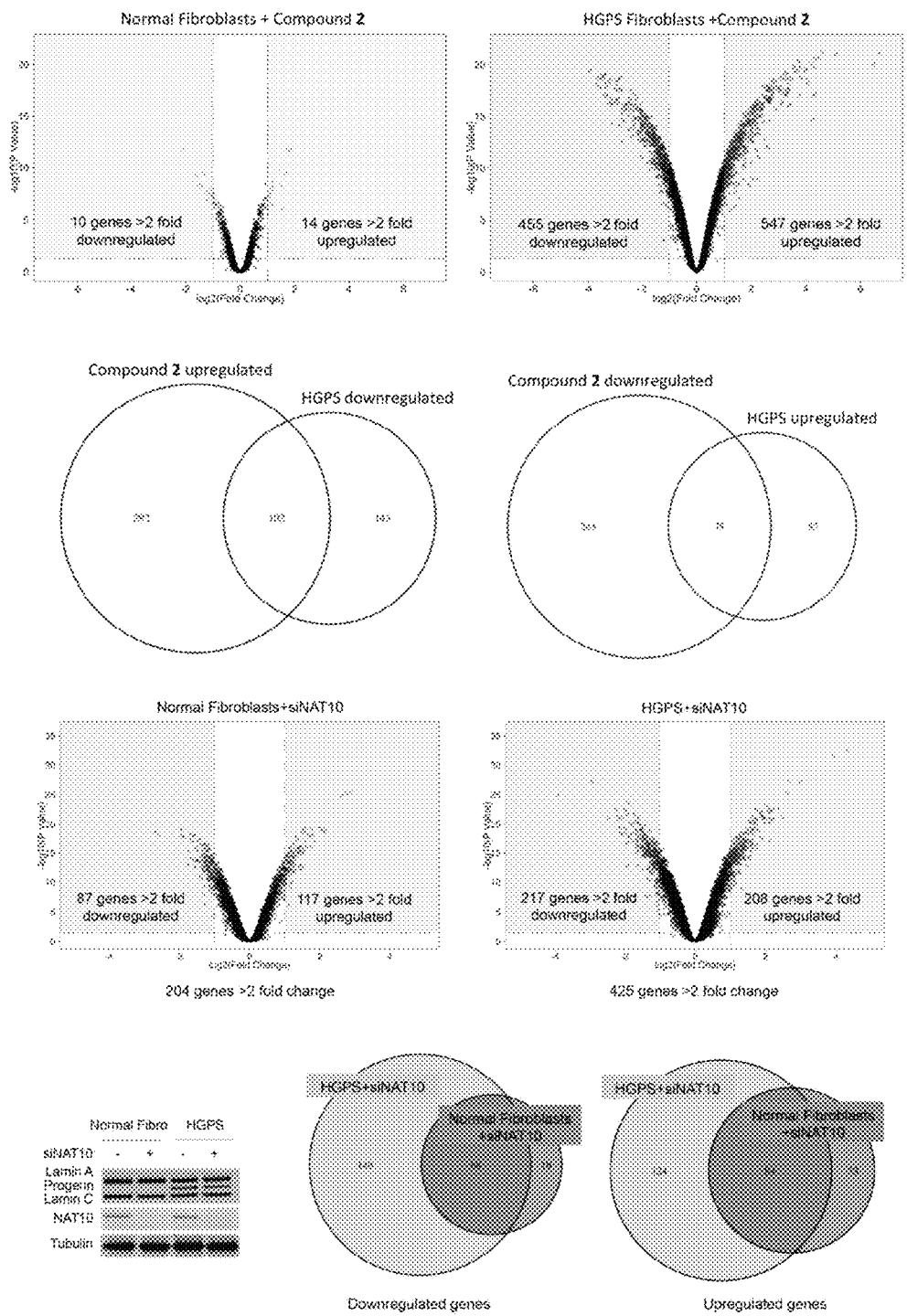
FIG. 29: Microarray analysis shows specificity of Compound 2 towards gene expression regulation in HGPS cells. The results of this analysis are described in Example 16.

Example 16: Microarray Analysis Shows Specificity of Compound 2 Towards Gene Expression Regulation in HGPS Cells Normal fibroblasts or HGPS fibroblasts were kept in culture for 12 population doublings with chronic treatment of 1 μM Compound 2 (top panels of FIG. 29) or transfected with siRNA against NAT10 for 3 days (bottom panels of FIG. 29). RNA was extracted and global gene expression was analysed by microarray. Volcano plots show a very high specificity of Compound 2 towards gene expression regulation of HGPS cells, with about 1000 genes affected more than 2 fold, whereas only 24 genes were affected in normal fibroblasts. Venn diagrams (panel 2 of FIG. 29) show that about half of the genes that are misregulated in HGPS compared to normal fibroblasts are rescued by Compound 2 treatment. Bottom panels of FIG. 29: Volcano plots and Venn diagrams show that NAT10 depletion (see WB below for efficiency of NAT10 depletion) leads to change in the expression of about twice more genes in HGPS cells as compared to normal fibroblasts. About 30% of the genes affected by NAT10 depletion in HGPS cells were also affected by long-term Compound 2 treatment, suggesting that these are the genes regulated by NAT10 acetyl-transferase activity.

In conclusion, the present inventors have identified and characterized the small molecule Remodelin as a new agent that improves nuclear shape and fitness of both progeric and Lamin A/C depleted cells. To their knowledge, Remodelin is the first molecule that also reduces the steady state level of γH2AX in HGPS cells, which is believed to contribute to their premature ageing phenotype. Importantly, by using an unbiased in vivo and in vitro click-chemistry based approach, NAT10 was identified as the cellular target of Remodelin responsible for nuclear morphology rescue, via reorganization of the microtubule network. Thus, "small molecule inhibitors" of NAT10 provide new opportunities to study laminopathy-associated processes with valuable spatial and temporal resolution (T. U. Mayer et al. (1999) *Science* 286, 971), and might in due course yield new classes of drugs for alleviating dystrophic and premature ageing diseases.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

---

The invention claimed is:

1. A compound selected from:

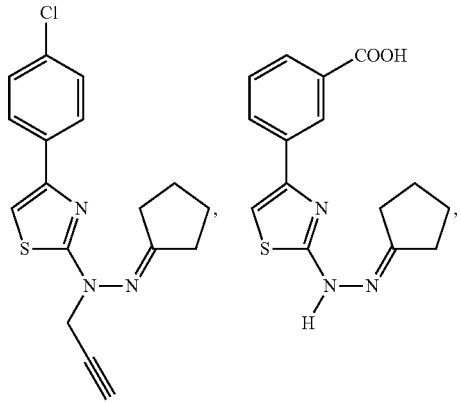

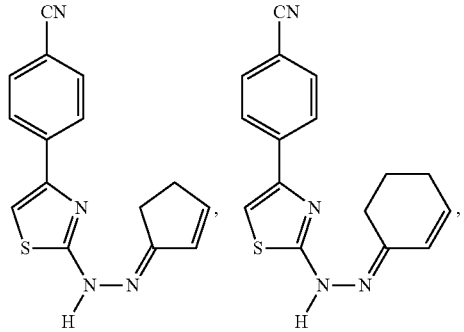

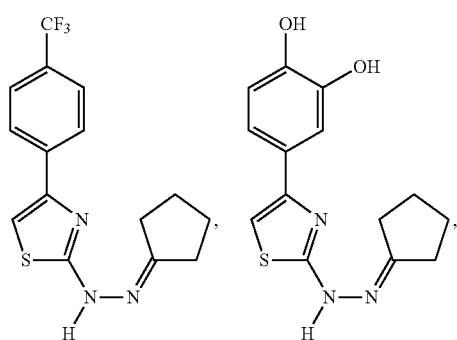

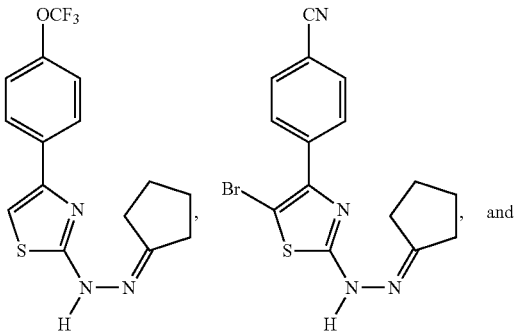

-continued

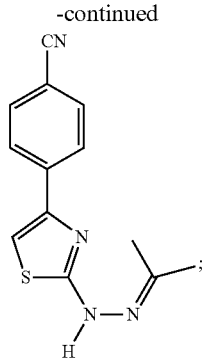

and salts or solvates of any one thereof.

2. A compound according to claim 1, wherein the compound is

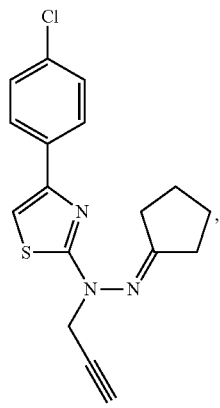 [SMILES: C#CCN(N=C1CCCC1)c1nc(-c2ccc(Cl)cc2)cs1]

or a salt or solvate thereof.

3. A compound according to claim 1, wherein the compound is

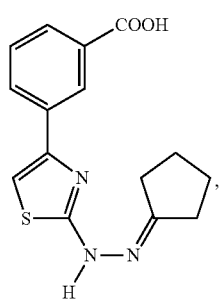 [SMILES: O=C(O)c1cccc(-c2csc(NN=C3CCCC3)n2)c1]

or a salt or solvate thereof.

4. A compound according to claim 1, wherein the compound is

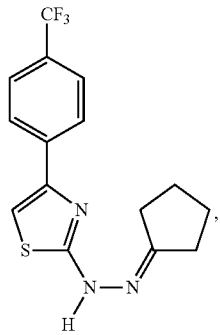

or a salt or solvate thereof.

5. A compound according to claim 1, wherein the compound is

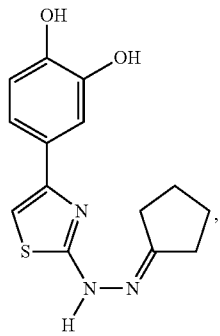 [SMILES: Oc1ccc(-c2csc(NN=C3CCCC3)n2)cc1O]

or a salt or solvate thereof.

6. A compound according to claim 1, wherein the compound is

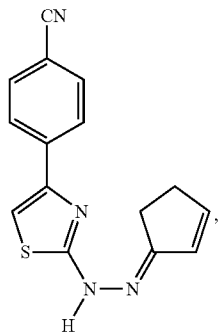 [SMILES: N#Cc1ccc(-c2csc(N/N=C3/C=CCC3)n2)cc1]

or a salt or solvate thereof.

7. A compound according to claim 1, wherein the compound is

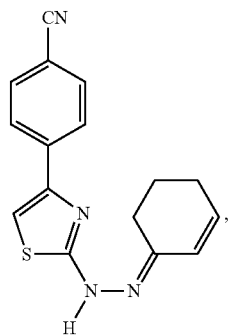 [SMILES: N#Cc1ccc(-c2csc(N/N=C3/C=CCCC3)n2)cc1]

or a salt or solvate thereof.

8. A compound according to claim 1, wherein the compound is

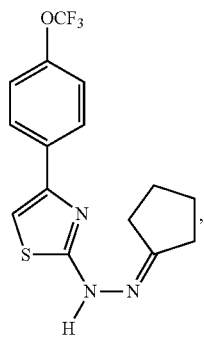 [SMILES: FC(F)(F)Oc1ccc(-c2csc(NN=C3CCCC3)n2)cc1]

or a salt or solvate thereof.

9. A compound according to claim 1, wherein the compound is

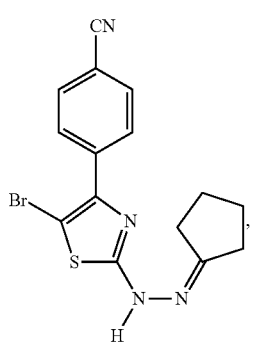 [SMILES: N#Cc1ccc(-c2nc(NN=C3CCCC3)sc2Br)cc1]

or a salt or solvate thereof.

10. A compound according to claim 1, wherein the compound is

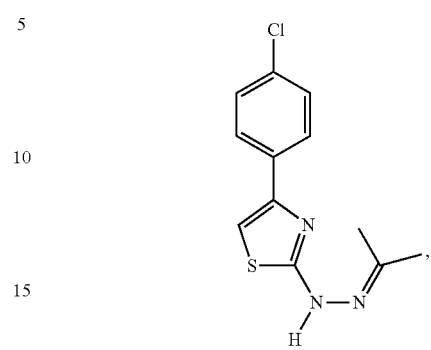

or a salt or solvate thereof.

11. A pharmaceutical composition comprising a compound according to claim 1 and one or more pharmaceutically acceptable carrier(s), diluents(s) and/or excipient(s).

12. A pharmaceutical composition comprising a compound according to claim 2 and one or more pharmaceutically acceptable carrier(s), diluents(s) and/or excipient(s).

13. A pharmaceutical composition comprising a compound according to claim 3 and one or more pharmaceutically acceptable carrier(s), diluents(s) and/or excipient(s).

14. A pharmaceutical composition comprising a compound according to claim 4 and one or more pharmaceutically acceptable carrier(s), diluents(s) and/or excipient(s).

15. A pharmaceutical composition comprising a compound according to claim 5 and one or more pharmaceutically acceptable carrier(s), diluents(s) and/or excipient(s).

16. A pharmaceutical composition comprising a compound according to claim 6 and one or more pharmaceutically acceptable carrier(s), diluents(s) and/or excipient(s).

17. A pharmaceutical composition comprising a compound according to claim 7 and one or more pharmaceutically acceptable carrier(s), diluents(s) and/or excipient(s).

18. A pharmaceutical composition comprising a compound according to claim 8 and one or more pharmaceutically acceptable carrier(s), diluents(s) and/or excipient(s).

19. A pharmaceutical composition comprising a compound according to claim 9 and one or more pharmaceutically acceptable carrier(s), diluents(s) and/or excipient(s).

20. A pharmaceutical composition comprising a compound according to claim 10 and one or more pharmaceutically acceptable carrier(s), diluents(s) and/or excipient(s).

* * * * *